(12) United States Patent
Lantz et al.

(10) Patent No.: US 11,517,300 B2
(45) Date of Patent: *Dec. 6, 2022

(54) METHOD AND APPARATUS FOR RE-ATTACHING THE LABRUM TO THE ACETABULUM, INCLUDING THE PROVISION AND USE OF A NOVEL SUTURE ANCHOR SYSTEM

(71) Applicant: Stryker Puerto Rico, LLC, San Juan, PR (US)

(72) Inventors: Andrew Lantz, Redwood City, CA (US); J. Brook Burley, Mountain View, CA (US); Jeremy Graul, Elk Grove, CA (US); James Flom, Redwood City, CA (US)

(73) Assignee: Stryker Puerto Rico, LLC

( * ) Notice: Subject to any disclaimer, the term of this patent is extended or adjusted under 35 U.S.C. 154(b) by 323 days.

This patent is subject to a terminal disclaimer.

(21) Appl. No.: 16/526,043

(22) Filed: Jul. 30, 2019

(65) Prior Publication Data

US 2020/0022693 A1 Jan. 23, 2020

Related U.S. Application Data

(63) Continuation of application No. 14/823,641, filed on Aug. 11, 2015, now Pat. No. 10,363,025, which is a
(Continued)

(51) Int. Cl.
*A61B 17/04* (2006.01)
*A61B 90/00* (2016.01)
(Continued)

(52) U.S. Cl.
CPC ...... *A61B 17/0401* (2013.01); *A61B 17/0467* (2013.01); *A61B 90/03* (2016.02);
(Continued)

(58) Field of Classification Search
CPC ............ A61B 17/0401; A61B 17/0467; A61B 17/1604; A61B 2017/0409;
(Continued)

(56) References Cited

U.S. PATENT DOCUMENTS 919,138 A 4/1909 Drake et al.
2,416,260 A 2/1947 Karie
(Continued)

FOREIGN PATENT DOCUMENTS

EP 0 232 049 8/1987
EP 0 241 240 10/1987
(Continued)

*Primary Examiner* — Robert A Lynch
(74) *Attorney, Agent, or Firm* — Pandiscio & Pandiscio

(57) ABSTRACT

Apparatus for securing an object to bone, the apparatus including an anchor assembly comprising an anchor and an actuation element extending from the anchor, wherein applying a force to the actuation element when the anchor is disposed in a hole formed in a bone secures the anchor to the bone; and an inserter for deploying the anchor assembly in a hole formed in a bone, the inserter including a shaft for releasably engaging the anchor; and a force delivery mechanism mounted to the shaft and connected to the actuation element, the force delivery mechanism being constructed so as to receive an input force from an external source and to selectively apply an output force to the actuation element, with the force delivery mechanism being constructed so that the magnitude of the output force is limited regardless of the magnitude of the input force.

50 Claims, 73 Drawing Sheets

Related U.S. Application Data continuation of application No. 13/538,378, filed on Jun. 29, 2012, now Pat. No. 9,101,355, which is a continuation-in-part of application No. 12/839,246, filed on Jul. 19, 2010, now Pat. No. 9,179,905, and a continuation-in-part of application No. PCT/US2011/021173, filed on Jan. 13, 2011.

(60) Provisional application No. 61/271,205, filed on Jul. 17, 2009, provisional application No. 61/326,709, filed on Apr. 22, 2010, provisional application No. 61/502,621, filed on Jun. 29, 2011.

(51) Int. Cl.
  A61B 17/16 (2006.01)
  A61B 17/17 (2006.01)

(52) U.S. Cl.
  CPC ....... A61B 17/1604 (2013.01); A61B 17/1666 (2013.01); A61B 17/1746 (2013.01); A61B 2017/0409 (2013.01); A61B 2017/0412 (2013.01); A61B 2017/0414 (2013.01); A61B 2017/0424 (2013.01); A61B 2017/0458 (2013.01); A61B 2017/0496 (2013.01); A61B 2090/037 (2016.02)

(58) Field of Classification Search
  CPC ...... A61B 2017/0412; A61B 2017/042; A61B 2017/0422; A61B 2017/0424; A61B 2017/0446; A61B 2017/0448; A61B 2017/045; A61B 2017/0451; A61B 2017/0458; A61B 2017/0496; A61B 2017/051; A61B 90/03; A61B 2090/037
  See application file for complete search history.

(56) References Cited

U.S. PATENT DOCUMENTS

| | | |
|---|---|---|
| 2,579,192 A | 12/1951 | Kohl |
| 2,808,055 A | 10/1957 | Thayer |
| 3,566,739 A | 3/1971 | Lebar |
| 3,708,883 A | 1/1973 | Flander |
| 4,408,938 A | 10/1983 | Maguire |
| 4,484,570 A | 11/1984 | Sutter et al. |
| 4,492,226 A | 1/1985 | Belykh et al. |
| 4,590,928 A | 5/1986 | Hunt et al. |
| 4,605,414 A | 8/1986 | Czajka |
| 4,632,100 A | 12/1986 | Somers et al. |
| 4,708,132 A | 11/1987 | Silvestrini |
| 4,741,330 A | 5/1988 | Hayhurst |
| 4,778,468 A | 10/1988 | Hunt et al. |
| 4,779,616 A | 10/1988 | Johnson |
| 4,870,957 A | 10/1989 | Goble et al. |
| 4,871,289 A | 10/1989 | Choiniere |
| 4,927,421 A | 5/1990 | Goble et al. |
| 5,037,422 A | 8/1991 | Hayhurst et al. |
| 5,046,513 A | 9/1991 | Gatturna et al. |
| 5,176,682 A | 1/1993 | Chow |
| 5,207,679 A | 5/1993 | Li |
| 5,209,753 A | 5/1993 | Biedermann et al. |
| 5,224,946 A | 7/1993 | Hayhurst et al. |
| 5,226,426 A | 7/1993 | Yoon |
| 5,236,445 A | 8/1993 | Hayhurst et al. |
| 5,268,001 A | 12/1993 | Nicholson et al. |
| 5,324,308 A | 6/1994 | Pierce |
| 5,330,442 A | 7/1994 | Green et al. |
| 5,336,240 A | 8/1994 | Metzler et al. |
| 5,354,298 A | 10/1994 | Lee et al. |
| 5,364,407 A | 11/1994 | Poll |
| 5,383,905 A | 1/1995 | Golds et al. |
| 5,405,352 A | 4/1995 | Weston |
| 5,411,523 A | 5/1995 | Goble |
| 5,417,712 A | 5/1995 | Whittaker et al. |
| 5,423,860 A | 6/1995 | Lizardi et al. |
| 5,464,427 A | 11/1995 | Curtis et al. |
| 5,472,452 A | 12/1995 | Trott |
| 5,480,403 A | 1/1996 | Lee et al. |
| 5,486,197 A | 1/1996 | Le et al. |
| 5,489,210 A | 2/1996 | Hanosh |
| 5,499,991 A | 3/1996 | Garman et al. |
| 5,501,683 A | 3/1996 | Trott |
| 5,501,692 A | 3/1996 | Riza |
| 5,501,695 A | 3/1996 | Anspach, Jr. et al. |
| 5,514,159 A | 5/1996 | Matula et al. |
| 5,522,844 A | 6/1996 | Johnson |
| 5,522,845 A | 6/1996 | Wenstrom, Jr. |
| 5,534,012 A | 7/1996 | Bonutti |
| 5,545,180 A | 8/1996 | Le et al. |
| 5,562,683 A | 10/1996 | Chan |
| 5,562,687 A | 10/1996 | Chan |
| 5,569,306 A | 10/1996 | Thal |
| 5,571,139 A | 11/1996 | Jenkins, Jr. |
| 5,584,835 A | 12/1996 | Greenfield |
| 5,601,557 A | 2/1997 | Hayhurst |
| 5,601,558 A | 2/1997 | Torrie et al. |
| 5,611,515 A | 3/1997 | Benderev et al. |
| 5,630,824 A | 5/1997 | Hart |
| 5,632,748 A | 5/1997 | Beck, Jr. et al. |
| 5,643,292 A | 7/1997 | Hart |
| 5,643,321 A | 7/1997 | McDevitt |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,681,320 A | 10/1997 | McGuire |
| 5,681,333 A | 10/1997 | Burkhart et al. |
| 5,683,419 A | 11/1997 | Thal |
| 5,690,649 A | 11/1997 | Li |
| 5,702,215 A | 12/1997 | Li |
| 5,702,397 A | 12/1997 | Goble et al. |
| 5,702,422 A | 12/1997 | Stone |
| 5,707,395 A | 1/1998 | Li |
| 5,709,708 A | 1/1998 | Thal |
| 5,713,903 A | 2/1998 | Sander et al. |
| 5,716,368 A | 2/1998 | de la Torre et al. |
| 5,720,765 A | 2/1998 | Thal |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,746,752 A | 5/1998 | Burkhart |
| 5,746,753 A | 5/1998 | Sullivan et al. |
| 5,755,728 A | 5/1998 | Maki |
| 5,782,862 A | 7/1998 | Bonutti |
| 5,782,863 A | 7/1998 | Bartlett |
| 5,782,864 A | 7/1998 | Lizardi |
| 5,791,899 A | 8/1998 | Sachdeva et al. |
| 5,797,963 A | 8/1998 | McDevitt |
| 5,814,071 A | 9/1998 | McDevitt et al. |
| 5,814,072 A | 9/1998 | Bonutti |
| 5,814,073 A | 9/1998 | Bonutti |
| 5,843,127 A | 12/1998 | Li |
| 5,845,645 A | 12/1998 | Bonutti |
| 5,849,004 A | 12/1998 | Bramlet |
| 5,891,168 A | 4/1999 | Thal |
| 5,906,624 A | 5/1999 | Wenstrom, Jr. |
| 5,910,148 A | 6/1999 | Reimels et al. |
| 5,911,721 A | 6/1999 | Nicholson et al. |
| 5,928,244 A | 7/1999 | Tovey et al. |
| 5,935,129 A | 8/1999 | McDevitt et al. |
| 5,935,134 A | 8/1999 | Pedlick et al. |
| 5,935,149 A | 8/1999 | Ek |
| 5,948,000 A | 9/1999 | Larsen et al. |
| 5,948,001 A | 9/1999 | Larsen |
| 5,957,953 A | 9/1999 | DiPoto et al. |
| 5,968,044 A | 10/1999 | Nicholson et al. |
| 5,980,558 A | 11/1999 | Wiley |
| 5,980,559 A | 11/1999 | Bonutti |
| 5,993,459 A | 11/1999 | Larsen et al. |
| 6,010,514 A | 1/2000 | Burney et al. |

(56) References Cited

U.S. PATENT DOCUMENTS

| | | |
|---|---|---|
| 6,022,360 A | 2/2000 | Reimels et al. |
| 6,041,485 A | 3/2000 | Pedlick et al. |
| 6,045,573 A | 4/2000 | Wenstrom, Jr. et al. |
| 6,045,574 A | 4/2000 | Thal |
| 6,056,772 A | 5/2000 | Bonutti |
| 6,077,277 A | 6/2000 | Mollenauer et al. |
| 6,086,608 A | 7/2000 | Ek et al. |
| 6,099,538 A | 8/2000 | Moses et al. |
| 6,099,547 A | 8/2000 | Gellman et al. |
| 6,117,144 A | 9/2000 | Nobles et al. |
| 6,143,017 A | 11/2000 | Thal |
| 6,149,669 A | 11/2000 | Li |
| 6,159,234 A | 12/2000 | Bonutti et al. |
| 6,200,329 B1 | 3/2001 | Fung et al. |
| 6,221,107 B1 | 4/2001 | Steiner et al. |
| 6,231,592 B1 | 5/2001 | Bonutti et al. |
| 6,241,732 B1 | 6/2001 | Overaker et al. |
| 6,245,081 B1 | 6/2001 | Bowman et al. |
| 6,245,082 B1 | 6/2001 | Gellman et al. |
| 6,312,448 B1 | 11/2001 | Bonutti |
| 6,319,252 B1 | 11/2001 | McDevitt et al. |
| 6,319,269 B1 | 11/2001 | Li |
| 6,475,230 B1 | 11/2002 | Bonutti et al. |
| RE37,963 E | 1/2003 | Thal |
| 6,506,190 B1 | 1/2003 | Walshe |
| 6,517,579 B1 | 2/2003 | Paulos et al. |
| 6,520,980 B1 | 2/2003 | Foerster |
| 6,524,316 B1 | 2/2003 | Nicholson et al. |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,547,800 B2 | 4/2003 | Foerster et al. |
| 6,547,807 B2 | 4/2003 | Chan et al. |
| 6,562,071 B2 | 5/2003 | Järvinen |
| 6,575,976 B2 | 6/2003 | Grafton |
| 6,575,987 B2 | 6/2003 | Gellman et al. |
| 6,582,453 B1 | 6/2003 | Tran et al. |
| 6,585,730 B1 | 7/2003 | Foerster |
| 6,620,166 B1 | 9/2003 | Wenstrom, Jr. et al. |
| 6,629,984 B1 | 10/2003 | Chan |
| 6,641,596 B1 | 11/2003 | Lizardi |
| 6,641,597 B2 | 11/2003 | Burkhart et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,692,516 B2 | 2/2004 | West, Jr. et al. |
| 6,733,506 B1 | 5/2004 | McDevitt et al. |
| 6,746,457 B2 | 6/2004 | Dana et al. |
| 6,752,814 B2 | 6/2004 | Gellman et al. |
| 6,770,073 B2 | 8/2004 | McDevitt et al. |
| 6,770,076 B2 | 8/2004 | Foerster |
| 6,780,198 B1 | 8/2004 | Gregoire et al. |
| 6,814,741 B2 | 11/2004 | Bowman et al. |
| 6,855,157 B2 | 2/2005 | Foerster et al. |
| 6,887,259 B2 | 5/2005 | Lizardi |
| 6,932,834 B2 | 8/2005 | Lizardi et al. |
| 6,942,666 B2 | 9/2005 | Overaker et al. |
| 6,986,781 B2 | 1/2006 | Smith |
| 6,991,636 B2 | 1/2006 | Rose |
| 7,033,380 B2 | 4/2006 | Schwartz et al. |
| 7,037,324 B2 | 5/2006 | Martinek |
| 7,041,120 B2 | 5/2006 | Li et al. |
| 7,048,755 B2 | 5/2006 | Bonutti et al. |
| 7,074,203 B1 | 7/2006 | Johanson et al. |
| 7,081,126 B2 | 7/2006 | McDevitt et al. |
| 7,083,638 B2 | 8/2006 | Foerster |
| 7,090,690 B2 | 8/2006 | Foerster et al. |
| 7,144,415 B2 | 12/2006 | Del Rio et al. |
| 7,160,314 B2 | 1/2007 | Sgro et al. |
| 7,226,469 B2 | 6/2007 | Benavitz et al. |
| 7,235,100 B2 | 6/2007 | Martinek |
| 7,309,346 B2 | 12/2007 | Martinek |
| 7,329,272 B2 | 2/2008 | Burkhart et al. |
| 7,381,213 B2 | 6/2008 | Lizardi |
| 7,507,200 B2 | 3/2009 | Okada |
| 7,517,357 B2 | 4/2009 | Abrams et al. |
| 7,556,640 B2 | 7/2009 | Foerster |
| 7,637,926 B2 | 12/2009 | Foerster et al. |
| 7,662,171 B2 | 2/2010 | West, Jr. et al. |
| 7,674,274 B2 | 3/2010 | Foerster et al. |
| 7,674,276 B2 | 3/2010 | Stone et al. |
| 7,682,374 B2 | 3/2010 | Foerster et al. |
| 7,695,494 B2 | 4/2010 | Foerster |
| 7,704,262 B2 | 4/2010 | Bellafiore et al. |
| 7,713,286 B2 | 5/2010 | Singhatat |
| 7,780,701 B1 | 8/2010 | Meridew et al. |
| 7,794,484 B2 | 9/2010 | Stone et al. |
| 7,828,820 B2 | 11/2010 | Stone et al. |
| 7,837,710 B2 | 11/2010 | Lombardo et al. |
| 7,842,050 B2 | 11/2010 | Diduch et al. |
| 7,846,167 B2 | 12/2010 | Garcia et al. |
| 7,867,264 B2 | 1/2011 | Mcdevitt et al. |
| 7,896,907 B2 | 3/2011 | McDevitt et al. |
| 7,938,847 B2 | 5/2011 | Fanton et al. |
| 7,963,972 B2 | 6/2011 | Foerster et al. |
| 7,976,565 B1 | 7/2011 | Meridew et al. |
| 7,993,369 B2 | 8/2011 | Dreyfuss |
| 8,029,537 B2 | 10/2011 | West, Jr. et al. |
| 8,057,524 B2 | 11/2011 | Meridew |
| 8,066,718 B2 | 11/2011 | Weisel et al. |
| 8,075,572 B2 | 12/2011 | Stefanchik et al. |
| RE43,143 E | 1/2012 | Hayhurst |
| 8,100,942 B1 | 1/2012 | Green et al. |
| 8,109,969 B1 | 2/2012 | Green et al. |
| 8,118,835 B2 | 2/2012 | Weisel et al. |
| 8,128,641 B2 | 3/2012 | Wardle |
| 8,133,258 B2 | 3/2012 | Foerster et al. |
| 8,137,381 B2 | 3/2012 | Foerster et al. |
| 8,137,383 B2 | 3/2012 | West, Jr. et al. |
| 8,162,978 B2 | 4/2012 | Lombardo et al. |
| 8,298,291 B2 | 10/2012 | Bonutti |
| 8,409,252 B2 | 4/2013 | Lombardo et al. |
| 8,435,264 B2 | 5/2013 | Sojka et al. |
| 8,444,672 B2 | 5/2013 | Foerster |
| 8,444,674 B2 | 5/2013 | Kaplan |
| 8,454,704 B2 | 6/2013 | Frushell et al. |
| 8,460,340 B2 | 6/2013 | Sojka et al. |
| 8,469,998 B2 | 6/2013 | Sojka et al. |
| 8,491,600 B2 | 7/2013 | McDevitt et al. |
| 8,523,902 B2 | 9/2013 | Heaven et al. |
| 8,545,535 B2 | 10/2013 | Hirotsuka et al. |
| 8,545,536 B2 | 10/2013 | Mayer et al. |
| 8,613,756 B2 | 12/2013 | Lizardi et al. |
| 8,632,568 B2 | 1/2014 | Miller et al. |
| 8,834,543 B2 | 9/2014 | McDevitt et al. |
| 8,986,345 B2 | 3/2015 | Denham et al. |
| 2001/0002436 A1 | 5/2001 | Bowman et al. |
| 2001/0049529 A1 | 12/2001 | Cachia et al. |
| 2002/0040241 A1 | 4/2002 | Jarvinen |
| 2002/0095180 A1* | 7/2002 | West, Jr. ............ A61B 17/0401 606/228 |
| 2002/0115999 A1 | 8/2002 | McDevitt et al. |
| 2002/0147456 A1 | 10/2002 | Diduch et al. |
| 2003/0004545 A1 | 1/2003 | Burkhart et al. |
| 2003/0065361 A1 | 4/2003 | Dreyfuss |
| 2003/0139752 A1 | 7/2003 | Pasricha et al. |
| 2003/0195563 A1 | 10/2003 | Foerster |
| 2003/0195564 A1 | 10/2003 | Tran et al. |
| 2004/0093031 A1 | 5/2004 | Burkhart et al. |
| 2004/0138706 A1 | 7/2004 | Abrams et al. |
| 2004/0220573 A1 | 11/2004 | McDevitt et al. |
| 2004/0249393 A1 | 12/2004 | Weisel et al. |
| 2005/0004644 A1 | 1/2005 | Kelsch et al. |
| 2005/0049592 A1 | 3/2005 | Keith et al. |
| 2005/0075668 A1 | 4/2005 | Lizardi |
| 2005/0149122 A1 | 7/2005 | McDevitt et al. |
| 2005/0245932 A1 | 11/2005 | Fanton et al. |
| 2005/0277986 A1 | 12/2005 | Foerster et al. |
| 2005/0283171 A1 | 12/2005 | Bellafiore et al. |
| 2006/0052788 A1 | 3/2006 | Thelen et al. |
| 2006/0079904 A1 | 4/2006 | Thal |
| 2006/0081553 A1 | 4/2006 | Patterson et al. |
| 2006/0106422 A1* | 5/2006 | Del Rio ............... A61F 2/0811 606/232 |

(56) References Cited

U.S. PATENT DOCUMENTS

| | | |
|---|---|---|
| 2006/0106423 A1 | 5/2006 | Weisel et al. |
| 2006/0217762 A1 | 9/2006 | Maahs et al. |
| 2006/0235413 A1 | 10/2006 | Denham et al. |
| 2006/0265010 A1 | 11/2006 | Paraschac et al. |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2007/0005068 A1 | 1/2007 | Sklar |
| 2007/0060922 A1 | 3/2007 | Dreyfuss |
| 2007/0093858 A1 | 4/2007 | Gambale et al. |
| 2007/0142835 A1 | 6/2007 | Green et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0203498 A1 | 8/2007 | Gerber et al. |
| 2007/0219557 A1 | 9/2007 | Bourque et al. |
| 2007/0255317 A1 | 11/2007 | Fanton et al. |
| 2007/0260259 A1 | 11/2007 | Fanton et al. |
| 2007/0270889 A1 | 11/2007 | Conlon et al. |
| 2007/0270907 A1 | 11/2007 | Stokes et al. |
| 2007/0288027 A1 | 12/2007 | Grafton et al. |
| 2008/0033460 A1 | 2/2008 | Ziniti et al. |
| 2008/0086138 A1 | 4/2008 | Stone et al. |
| 2008/0275469 A1 | 11/2008 | Fanton et al. |
| 2008/0294177 A1 | 11/2008 | To et al. |
| 2008/0306510 A1 | 12/2008 | Stchur |
| 2009/0018554 A1 | 1/2009 | Thorne et al. |
| 2009/0082807 A1 | 3/2009 | Miller et al. |
| 2009/0099598 A1 | 4/2009 | McDevitt et al. |
| 2009/0112214 A1 | 4/2009 | Philippon et al. |
| 2009/0192545 A1 | 7/2009 | Workman |
| 2009/0222041 A1 | 9/2009 | Foerster |
| 2009/0248068 A1 | 10/2009 | Lombardo et al. |
| 2009/0292321 A1 | 11/2009 | Collette |
| 2009/0299386 A1 | 12/2009 | Meridew |
| 2009/0306711 A1 | 12/2009 | Stone et al. |
| 2009/0312794 A1 | 12/2009 | Nason et al. |
| 2010/0004683 A1 | 1/2010 | Hoof et al. |
| 2010/0049213 A1 | 2/2010 | Serina et al. |
| 2010/0063542 A1 | 3/2010 | van der Burg et al. |
| 2010/0069925 A1 | 3/2010 | Friedman et al. |
| 2010/0094314 A1 | 4/2010 | Hernlund et al. |
| 2010/0094355 A1 | 4/2010 | Trenhaile |
| 2010/0094425 A1 | 4/2010 | Bentley et al. |
| 2010/0100127 A1 | 4/2010 | Trenhaile |
| 2010/0114162 A1 | 5/2010 | Bojarski et al. |
| 2010/0121348 A1 | 5/2010 | van der Burg et al. |
| 2010/0121349 A1 | 5/2010 | Meier et al. |
| 2010/0191283 A1 | 7/2010 | Foerster et al. |
| 2010/0198258 A1 | 8/2010 | Heaven et al. |
| 2010/0222812 A1 | 9/2010 | Stone et al. |
| 2010/0251861 A1 | 10/2010 | Sixto, Jr. et al. |
| 2010/0292731 A1 | 11/2010 | Gittings et al. |
| 2010/0305576 A1 | 12/2010 | Ferguson et al. |
| 2011/0015674 A1 | 1/2011 | Howard et al. |
| 2011/0046682 A1 | 2/2011 | Stephan et al. |
| 2011/0071545 A1 | 3/2011 | Pamichev et al. |
| 2011/0071549 A1 | 3/2011 | Caborn et al. |
| 2011/0098728 A1 | 4/2011 | McDevitt et al. |
| 2011/0152929 A1 | 6/2011 | McDevitt et al. |
| 2011/0224726 A1 | 9/2011 | Lombardo et al. |
| 2011/0238113 A1 | 9/2011 | Fanton et al. |
| 2011/0264140 A1 | 10/2011 | Lizardi et al. |
| 2011/0295279 A1 | 12/2011 | Stone et al. |
| 2011/0301621 A1 | 12/2011 | Oren et al. |
| 2011/0301622 A1 | 12/2011 | Oren et al. |
| 2012/0041485 A1 | 2/2012 | Kaiser et al. |
| 2012/0053629 A1 | 3/2012 | Reiser et al. |
| 2012/0059417 A1 | 3/2012 | Norton et al. |
| 2012/0143221 A1 | 6/2012 | Weisel et al. |
| 2012/0150223 A1 | 6/2012 | Manos et al. |
| 2013/0006276 A1 | 1/2013 | Lantz et al. |
| 2013/0023930 A1 | 1/2013 | Stone et al. |
| 2013/0096611 A1 | 4/2013 | Sullivan |
| 2013/0103083 A1 | 4/2013 | Baird |
| 2013/0103084 A1 | 4/2013 | Pamichev et al. |
| 2013/0138152 A1 | 5/2013 | Stone et al. |
| 2013/0144334 A1 | 6/2013 | Bouduban et al. |
| 2013/0144338 A1 | 6/2013 | Stone et al. |
| 2013/0184748 A1 | 7/2013 | Sojka et al. |
| 2013/0204298 A1 | 8/2013 | Graul et al. |
| 2013/0267998 A1 | 10/2013 | Vijay et al. |
| 2013/0296931 A1 | 11/2013 | Sengun |
| 2014/0249579 A1 | 9/2014 | Heaven et al. |
| 2014/0257382 A1 | 9/2014 | McCartney |
| 2014/0316460 A1 | 10/2014 | Graul et al. |
| 2015/0100087 A1 | 4/2015 | Graul et al. |

FOREIGN PATENT DOCUMENTS

| | | |
|---|---|---|
| EP | 0 251 583 | 1/1988 |
| EP | 0 270 704 | 6/1988 |
| EP | 0 318 426 | 5/1989 |
| EP | 0 574 707 | 12/1993 |
| EP | 0 673 624 | 9/1995 |
| EP | 0 834 281 | 4/1998 |
| EP | 1 016 377 | 7/2000 |
| EP | 1 568 327 | 8/2005 |
| EP | 1 762 187 | 3/2007 |
| EP | 1 825 817 | 8/2007 |
| EP | 2 335 603 | 6/2011 |
| WO | WO 92/04874 | 4/1992 |
| WO | WO 95/15726 | 6/1995 |
| WO | WO 97/03615 | 2/1997 |
| WO | WO 97/30649 | 8/1997 |
| WO | WO 98/38938 | 9/1998 |
| WO | WO 2008/063915 | 5/2008 |
| WO | WO 2011/060022 | 5/2011 |
| WO | WO 2012/034131 | 3/2012 |

\* cited by examiner

CAM-TYPE FEMOROACETABULAR IMPINGEMENT (FAI)
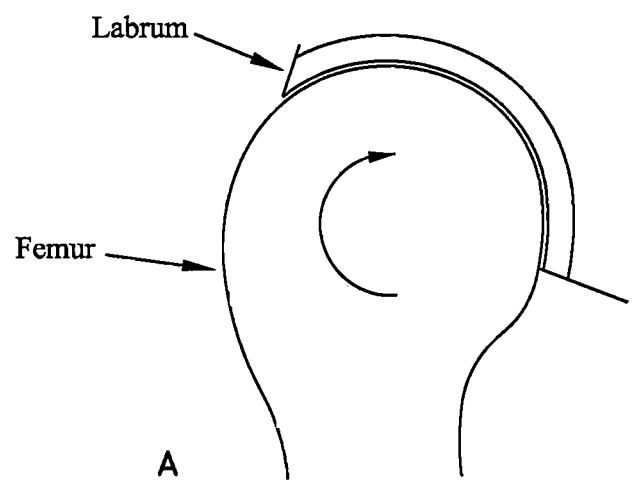
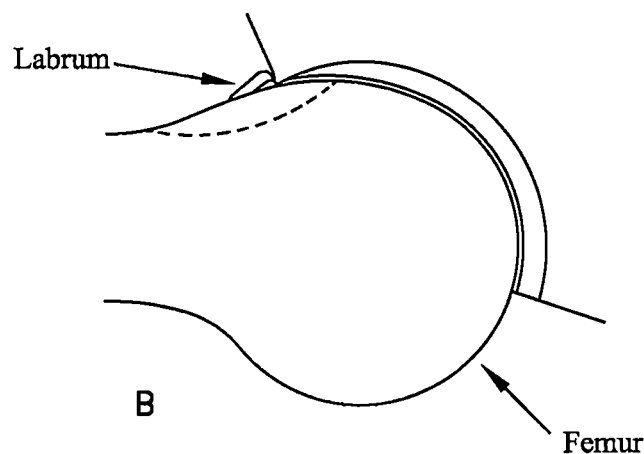
FIG. 13

PINCER-TYPE FEMOROACETABULAR IMPINGEMENT (FAI)
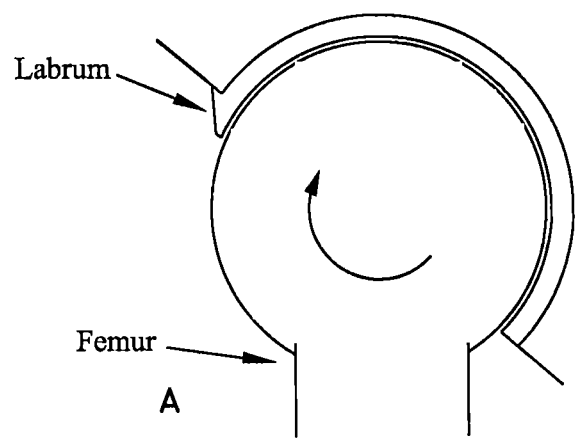
PINCER INJURY TO THE LABRUM
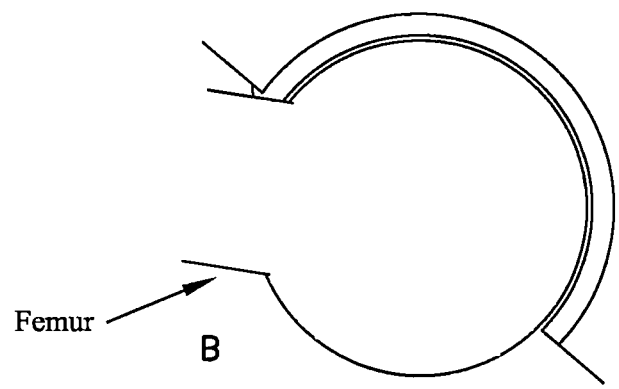
FIG. 14

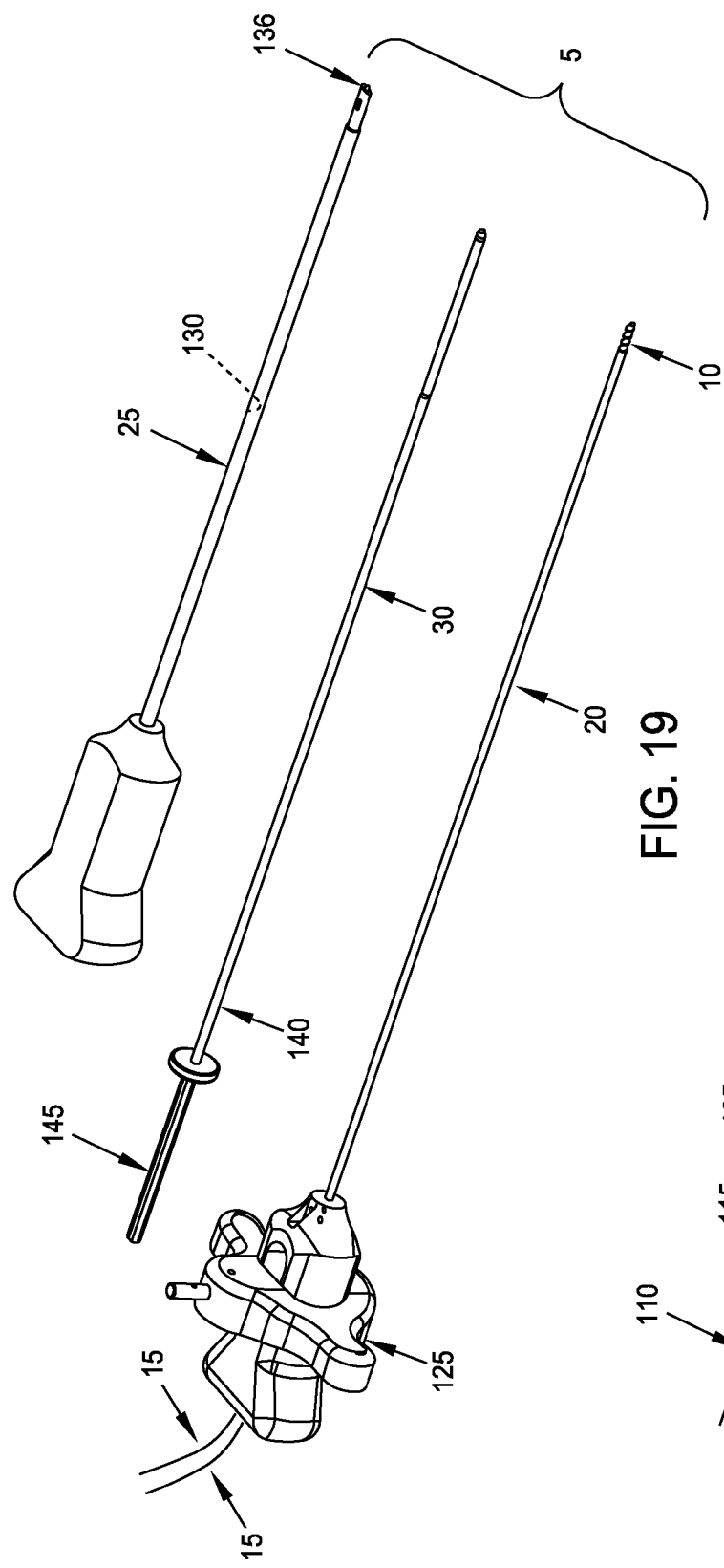
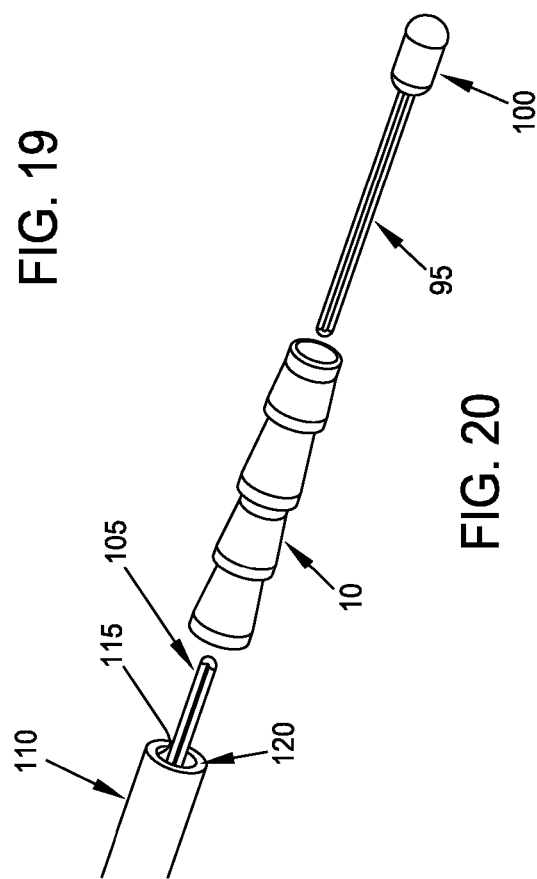
FIG. 19
FIG. 20

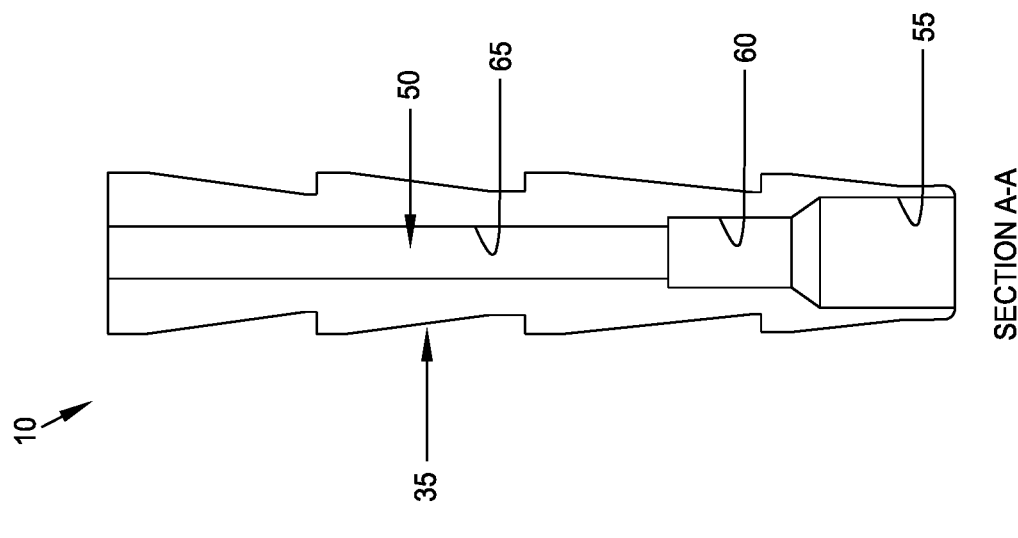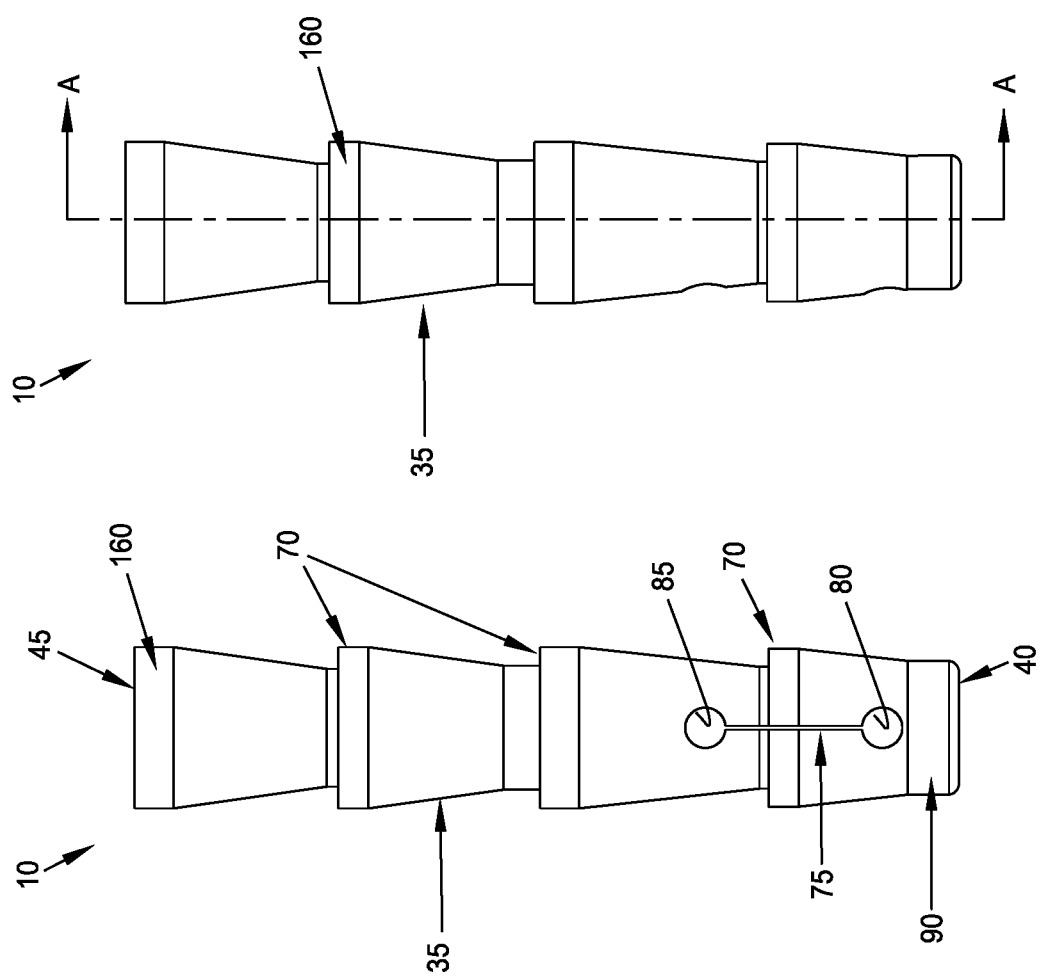

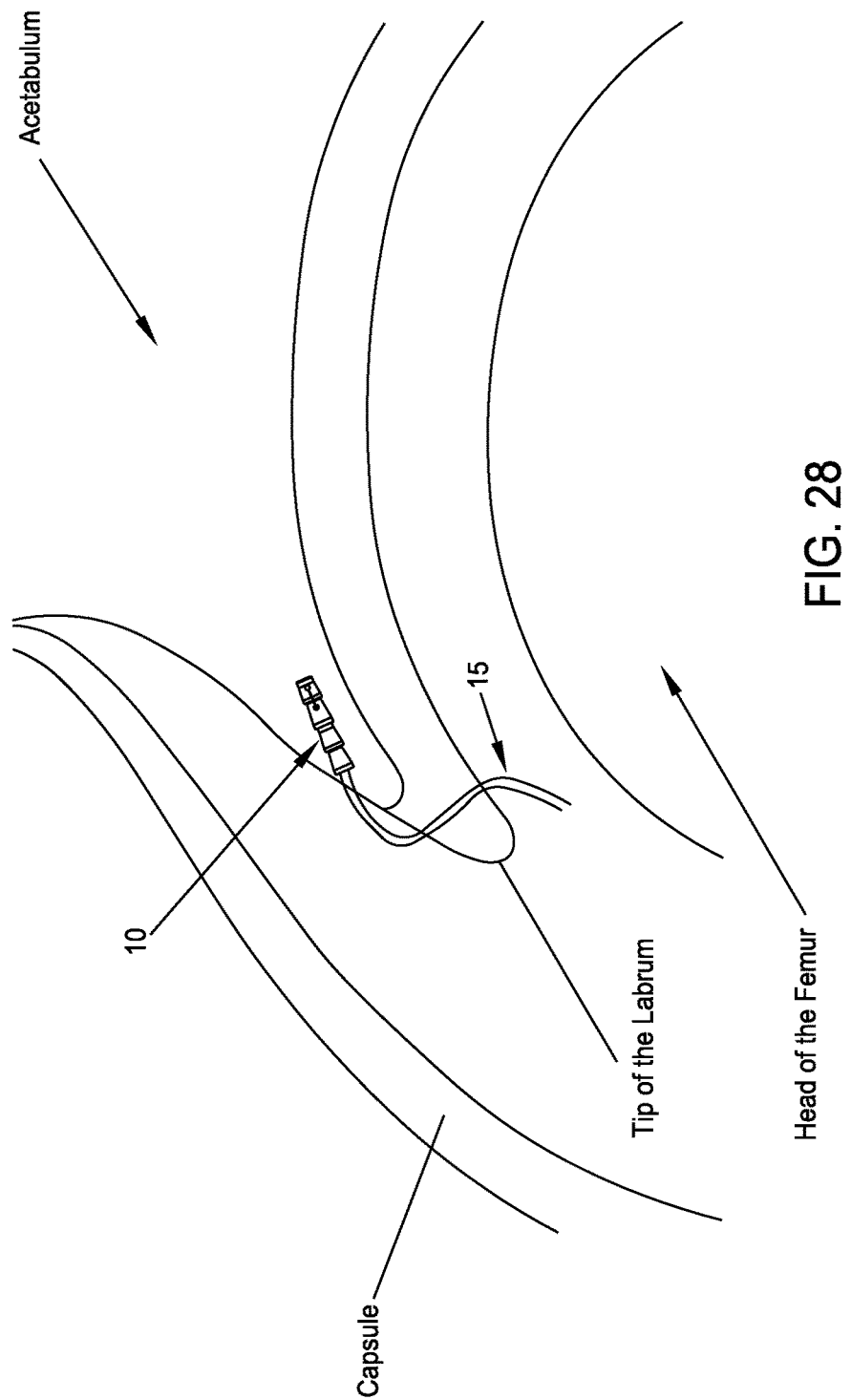

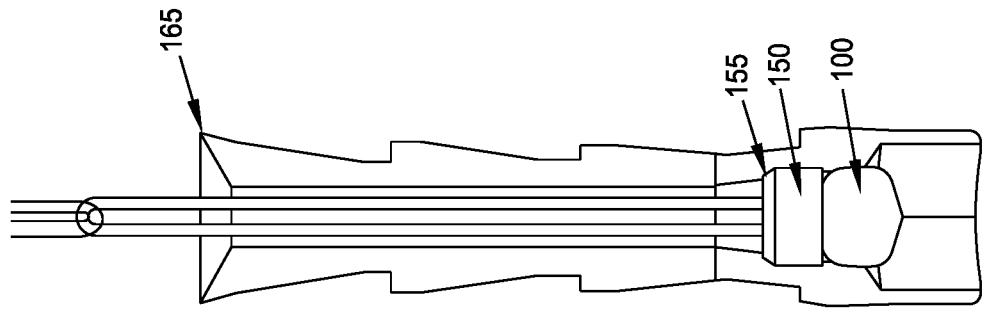
FIG. 29 ANCHOR WITH DEPLOYMENT CYLINDER
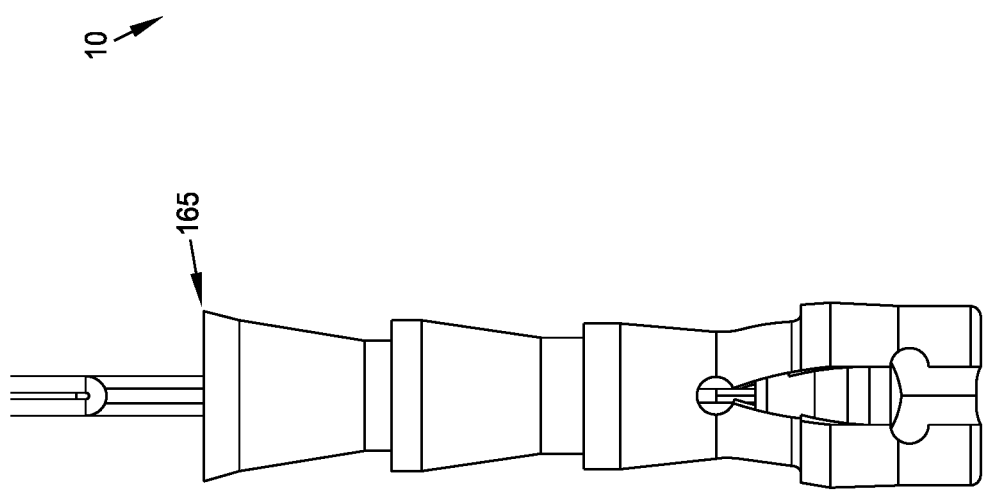
FIG. 30
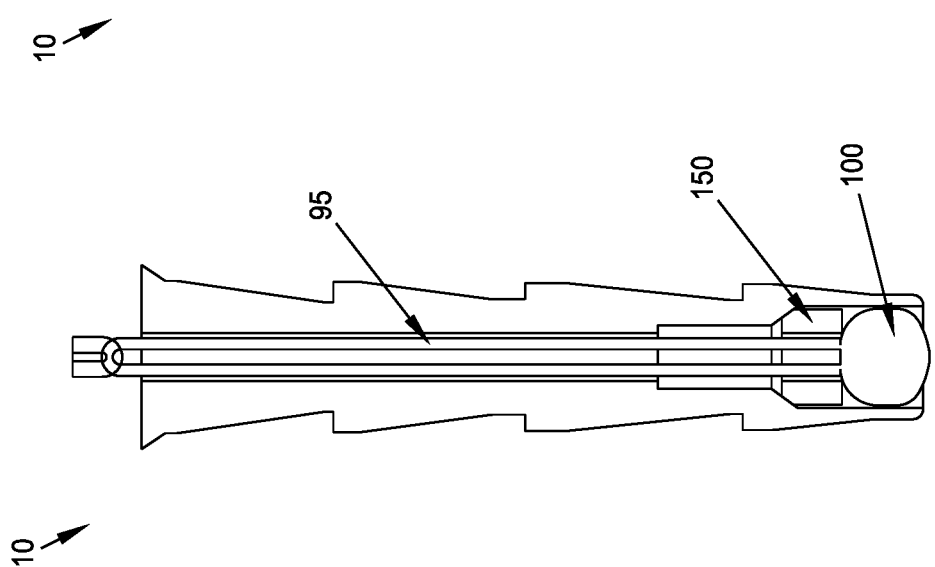
FIG. 31

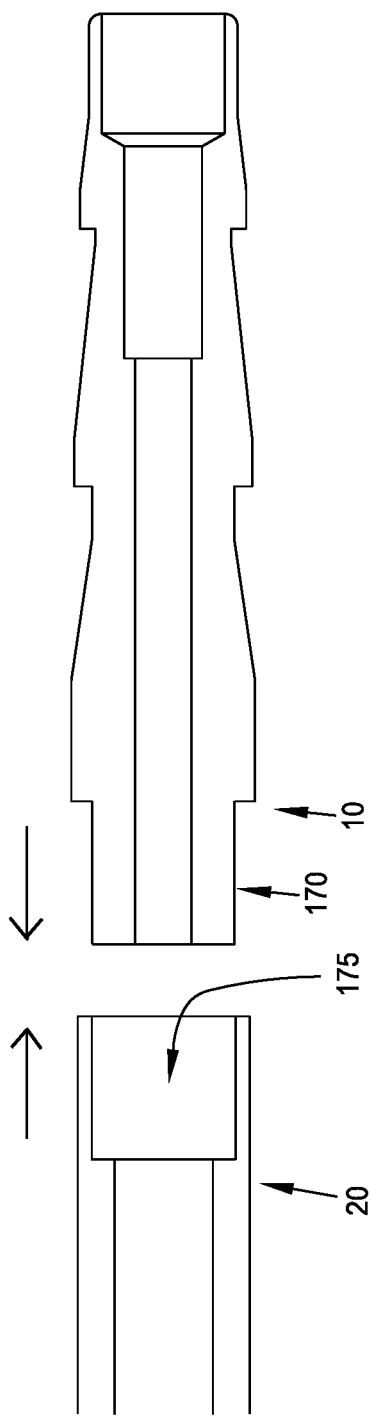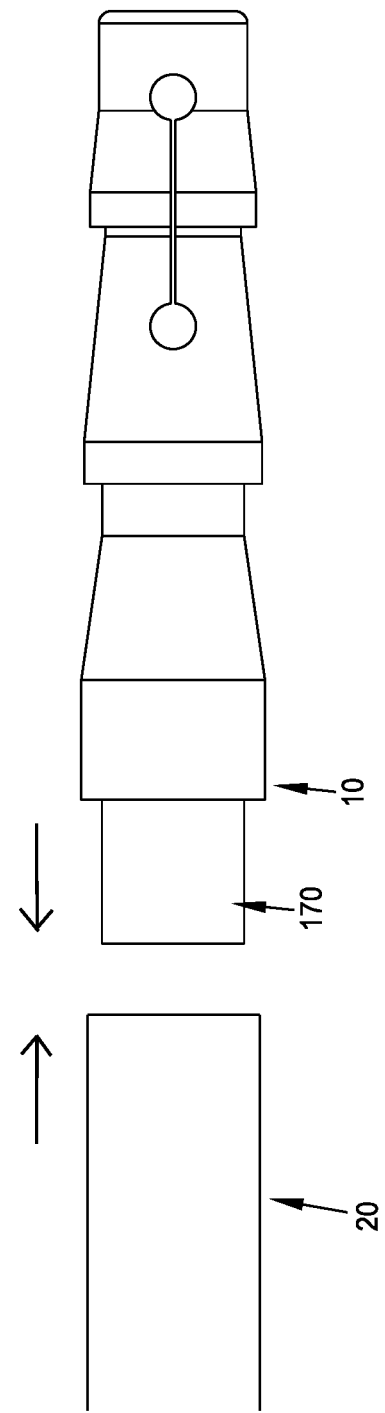
FIG. 33
FIG. 34
CAPTURE COUPLING FOR INSERTION

T-NOTCH COUPLING FOR INSERTION

BALL AND SOCKET COUPLING FOR INSERTION (ESPECIALLY HELPS WITH CURVED SYSTEM)

SECTION A-A

SUTURE (NOT SHOWN) PASSES OUTSIDE OF
THE PROXIMAL SECTION OF THE ANCHOR

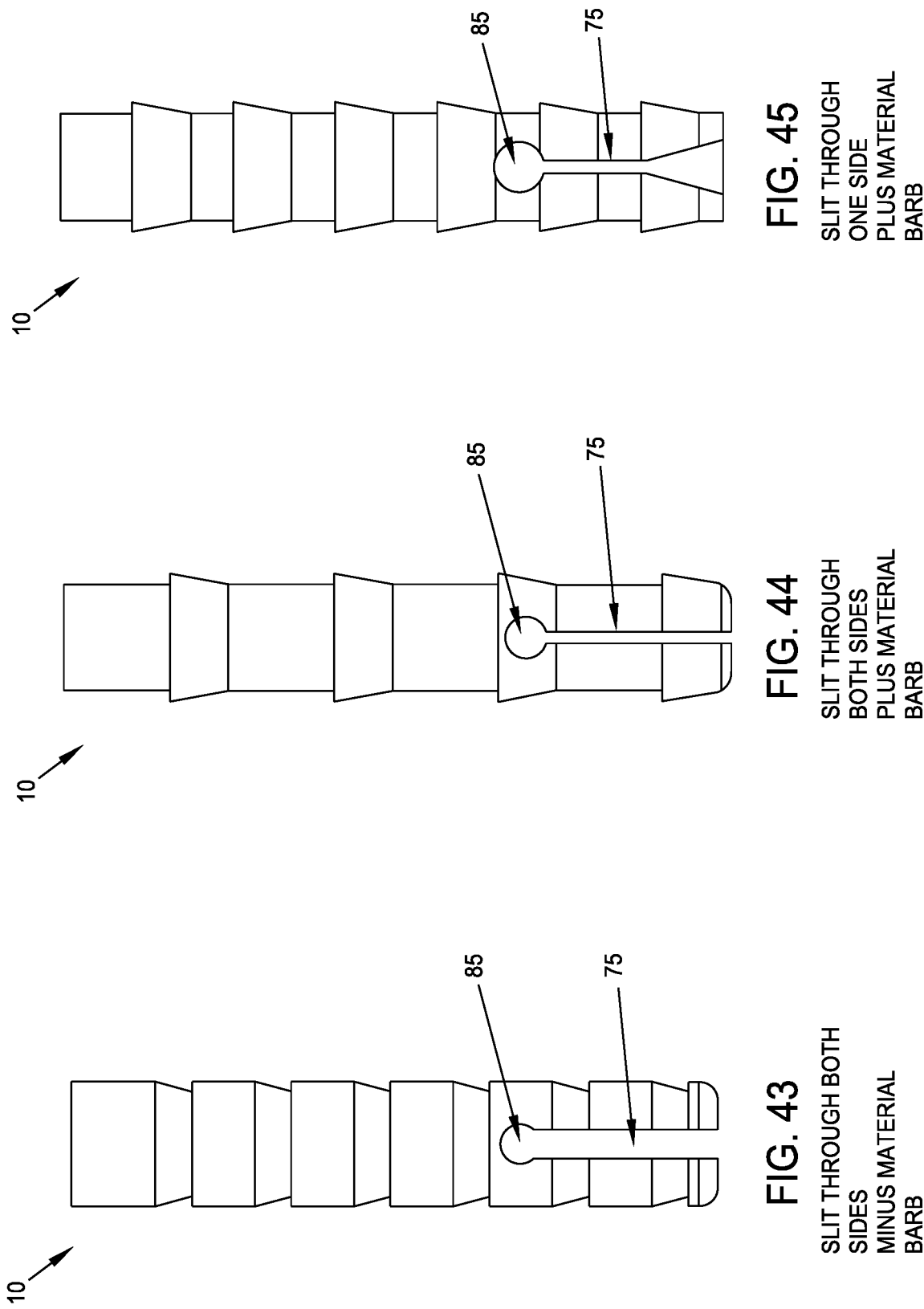

NON-CONCENTRIC THROUGH HOLE

ANGLED THROUGH HOLE

NO SLIT
PLUS MATERIAL
BARB

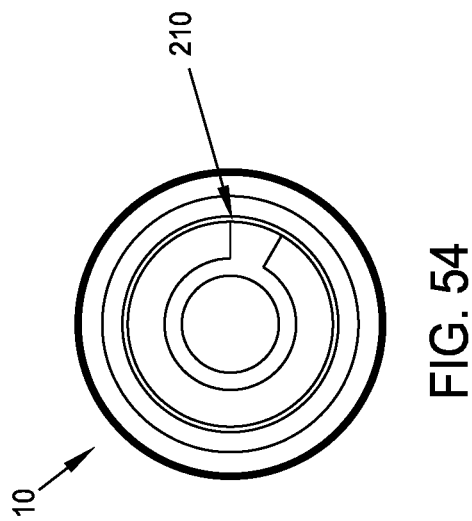
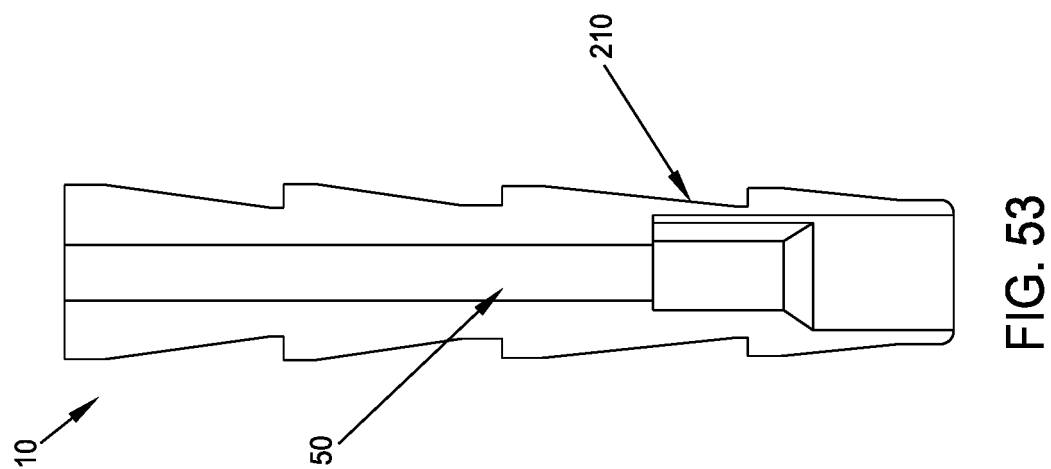
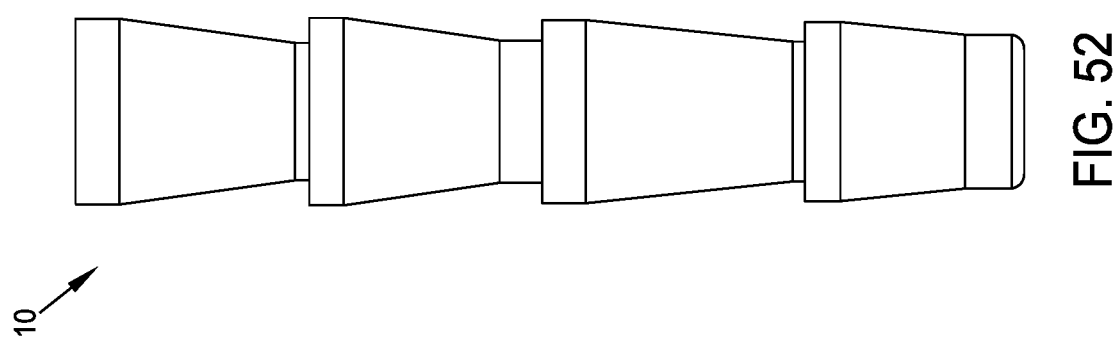

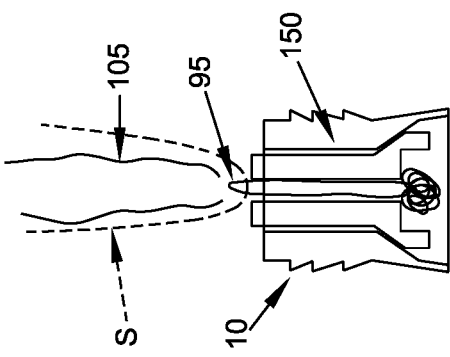
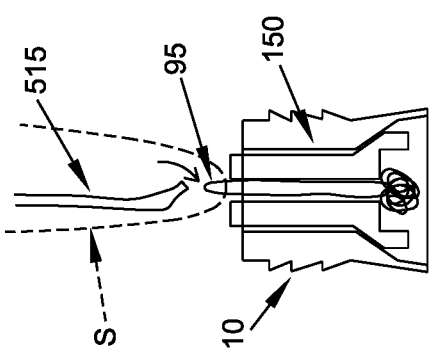

METHOD AND APPARATUS FOR RE-ATTACHING THE LABRUM TO THE ACETABULUM, INCLUDING THE PROVISION AND USE OF A NOVEL SUTURE ANCHOR SYSTEM

REFERENCE TO PENDING PRIOR PATENT APPLICATIONS

This patent application:

(i) is a continuation-in-part of pending prior U.S. patent application Ser. No. 12/839,246, filed Jul. 19, 2010 by Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM (Attorney's Docket No. FIAN-4655), which in turn claims benefit of (1) prior U.S. Provisional Patent Application Ser. No. 61/271,205, filed Jul. 17, 2009 by Chris Pamichev et al. for METHOD AND APPARATUS FOR RE-SECURING THE LABRUM TO THE ACETABULUM, INCLUDING THE PROVISION AND USE OF A NOVEL NANO TACK SYSTEM (Attorney's Docket No. FIAN-46 PROV), and (2) pending prior U.S. Provisional Patent Application Ser. No. 61/326,709, filed Apr. 22, 2010 by Chris Pamichev et al. for METHOD AND APPARATUS FOR RE-SECURING THE LABRUM TO THE ACETABULUM, INCLUDING THE PROVISION AND USE OF A NOVEL SUTURE ANCHOR SYSTEM (Attorney's Docket No. FIAN-55 PROV);

(ii) is a continuation-in-part of pending prior International (PCT) Patent Application No. PCT/US2011/021173, filed 13 Jan. 2011 by Pivot Medical, Inc. and Chris Pamichev et al. for METHOD AND APPARATUS FOR RE-ATTACHING THE LABRUM TO THE ACETABULUM, INCLUDING THE PROVISION AND USE OF A NOVEL SUTURE ANCHOR SYSTEM (Attorney's Docket No. FIAN-70 PCT); and (iii) claims benefit of pending prior U.S. Provisional Patent Application Ser. No. 61/502,621, filed Jun. 29, 2011 by Andrew Lantz et al. for FORCE-LIMITING (FORCE-CONTROLLING) DELIVERY MECHANISMS FOR THE CONTROLLED DELIVERY OF THE SUTURE ANCHOR (Attorney's Docket The five (5) above-identified patent applications are hereby incorporated herein by reference.

FIELD OF THE INVENTION

This invention relates to surgical methods and apparatus in general, and more particularly to surgical methods and apparatus for treating a hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the torso. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require large incisions into the interior of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Re-Attaching the Labrum of the Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted (i) when the labrum has been damaged but is still sufficiently healthy and intact as to be capable of repair and/or re-attachment, and (ii) when the labrum has been deliberately detached (e.g., so as to allow for acetabular rim trimming to treat a pathology such as a pincer-type FAI) and needs to be subsequently re-attached. See, for example, FIG. 16, which shows a normal labrum which has its base securely attached to the acetabulum, and FIG. 17, which shows a portion of the labrum (in this case the tip) detached from the acetabulum. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically repairing (e.g., re-attaching) the labrum are somewhat problematic. The present invention is intended to improve upon the current approaches for labrum repair.

More particularly, current approaches for arthroscopically repairing the labrum typically use apparatus originally designed for use in re-attaching ligaments to bone. For example, one such approach utilizes a screw-type bone anchor, with two sutures extending therefrom, and involves deploying the bone anchor in the acetabulum above the labrum re-attachment site. A first one of the sutures is passed either through the detached labrum or, alternatively, around the detached labrum. Then the first suture is tied to the second suture so as to support the labrum against the acetabular rim. See FIG. 18.

Unfortunately, bone anchors of the sort described above are traditionally used for re-attaching ligaments to bone and, as a result, tend to be relatively large, since they must carry the substantial pull-out forces normally associated with ligament reconstruction. However, this large anchor size is generally unnecessary for labrum re-attachment, since the labrum is not subjected to substantial pull-out forces, and the large anchor size typically causes unnecessary trauma to the patient.

Furthermore, the large size of traditional bone anchors can be problematic when the anchors are used for labrum re-attachment, since the bone anchors generally require a substantial bone mass for secure anchoring, and such a large bone mass is generally available only a substantial distance up the acetabular shelf. In addition, the large size of the bone anchors generally makes it necessary to set the bone anchor a substantial distance up the acetabular shelf, in order to ensure that the distal tip of the bone anchor does not inadvertently break through the acetabular shelf and contact the articulating surfaces of the joint. However, labral re-attachment utilizing a bone anchor set high up into the acetabular shelf creates a suture path, and hence a labral draw force, which is not directly aligned with the portion of the acetabular rim where the labrum is to be re-attached. As a result, an "indirect" draw force (also known as eversion) is typically applied to the labrum, i.e., the labrum is drawn around the rim of the acetabulum rather than directly into the acetabulum. See FIG. 18. This can sometimes result in a problematic labral re-attachment and, ultimately, can lead to a loss of the suction seal between the labrum and femoral head, which is a desired outcome of the labral re-attachment procedure.

Alternatively, the suture path can also surround the labrum, thus placing a suture on both sides of the labrum, including the articular side of the labrum, and thus exposing the articular surface of the femur to a foreign body, which could in turn cause damage to the articular surface (i.e., the articular cartilage) of the femur.

Accordingly, a new approach is needed for arthroscopically re-attaching the labrum to the acetabulum.

SUMMARY OF THE INVENTION

The present invention provides a novel method and apparatus for re-attaching the labrum to the acetabulum. Among other things, the present invention comprises the provision and use of a novel suture anchor system.

In one form of the invention, there is provided an inserter for deploying an anchor assembly in bone, wherein the anchor assembly comprises an anchor and an actuation element extending from the anchor, and further wherein deploying the anchor assembly in bone comprises positioning the anchor assembly in a hole formed in the bone and applying a force to the actuation element so as to secure the anchor to the bone, the inserter comprising:

a shaft for releasably engaging the anchor; and a force delivery mechanism mounted to the shaft and connected to the actuation element, the force delivery mechanism being constructed so as to receive an input force from an external source and to selectively apply an output force to the actuation element, with the force delivery mechanism being constructed so that the magnitude of the output force is limited regardless of the magnitude of the input force.

In another form of the invention, there is provided apparatus for securing an object to bone, the apparatus comprising:

an anchor assembly comprising an anchor and an actuation element extending from the anchor, wherein applying a force to the actuation element when the anchor is disposed in a hole formed in a bone secures the anchor to the bone; and an inserter for deploying the anchor assembly in a hole formed in a bone, the inserter comprising:

a shaft for releasably engaging the anchor; and a force delivery mechanism mounted to the shaft and connected to the actuation element, the force delivery mechanism being constructed so as to receive an input force from an external source and to selectively apply an output force to the actuation element, with the force delivery mechanism being constructed so that the magnitude of the output force is limited regardless of the magnitude of the input force.

In another form of the invention, there is provided a method for securing an object to bone, the method comprising:

using an inserter to position an anchor in a hole formed in a bone; and applying an input force to the inserter from an external source so as to selectively apply an output force to the anchor whereby to secure the anchor to the bone, with the inserter being constructed so that the magnitude of the output force applied to the anchor is limited regardless of the magnitude of the input force.

In another form of the invention, there is provided a method for securing an object to bone, the method comprising:

providing (i) an anchor assembly comprising an anchor and an actuation element extending from the anchor, and (ii) an inserter comprising a shaft for releasably engaging the anchor and a force delivery mechanism mounted to the shaft and connected to the actuation element, the force delivery mechanism being constructed so as to receive an input force from an external source and to selectively apply an output force to the actuation element, with the force delivery mechanism being constructed so that the magnitude of the output force is limited regardless of the magnitude of the input force;

using the inserter to position the anchor inside a hole formed in a bone; and using the force delivery mechanism to apply an output force to the actuation element, whereby to secure the anchor to the bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (i.e., cam-type FAI);

FIG. 14 is a schematic view showing pincer-type femoroacetabular impingement (i.e., pincer-type FAI);

FIGS. 19-27 are schematic views showing a novel suture anchor system for use in arthroscopically re-attaching a detached labrum to the acetabulum;

FIGS. 28 and 28A are schematic views showing the suture anchor system of FIGS. 19-27 being used to re-attach the labrum to the acetabulum;

FIGS. 29-31 are schematic views showing an alternative form of the suture anchor system of the present invention;

FIGS. 33-38 are schematic views showing alternative arrangements for coupling the anchor of the suture anchor system of FIGS. 19-27 to the inserter of the suture anchor system of FIGS. 19-27;

FIGS. 43-45 are schematic views showing another alternative form of the suture anchor system of the present invention;

FIGS. 52-54 are schematic views showing still another alternative form of the suture anchor system of the present invention;

FIGS. 87-100 are schematic views showing still other forms of the present invention, wherein the force delivery mechanism comprises a "controlled component failure" design (note that in FIGS. 87-100, the inserter is omitted from the figures for clarity of illustration).

DETAILED DESCRIPTION OF THE INVENTION

Figure 1A:
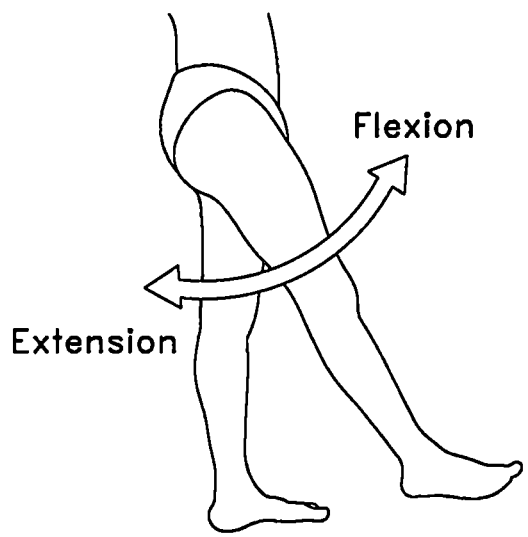
FIGS. 1A-1D are schematic views showing various aspects of hip motion.
Figure 1B:
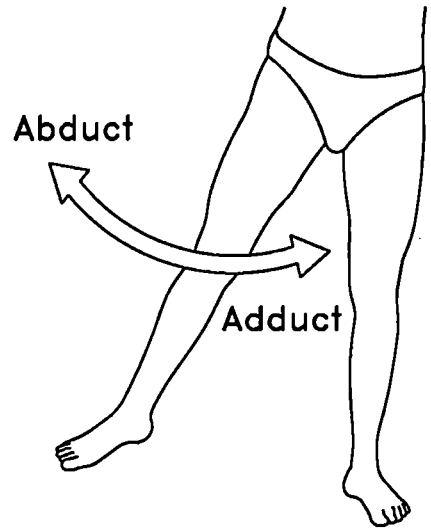
Figure 1C:
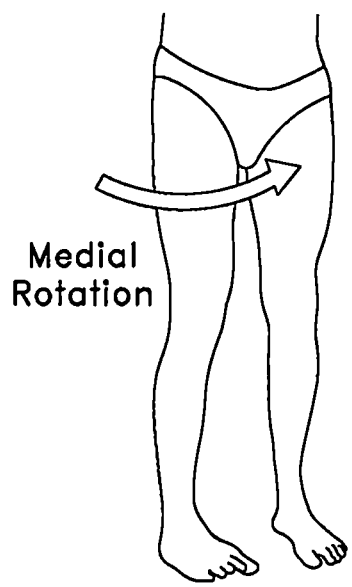
Figure 1D:
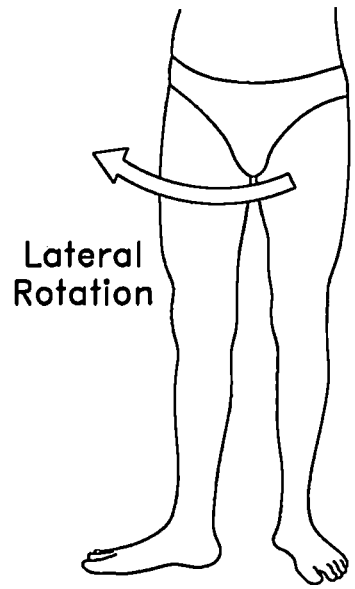
Figure 2:
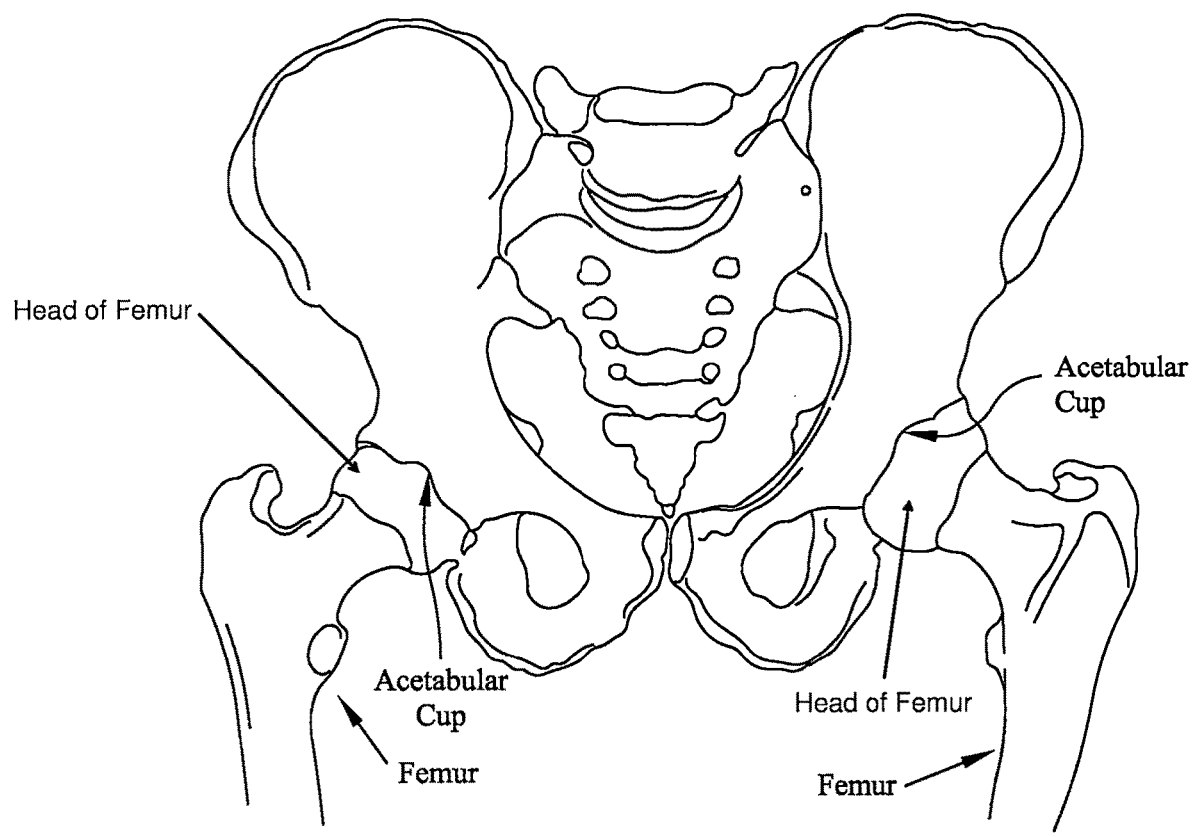
FIG. 2 is a schematic view showing bone structures in the region of the hip joint.
Figure 3:
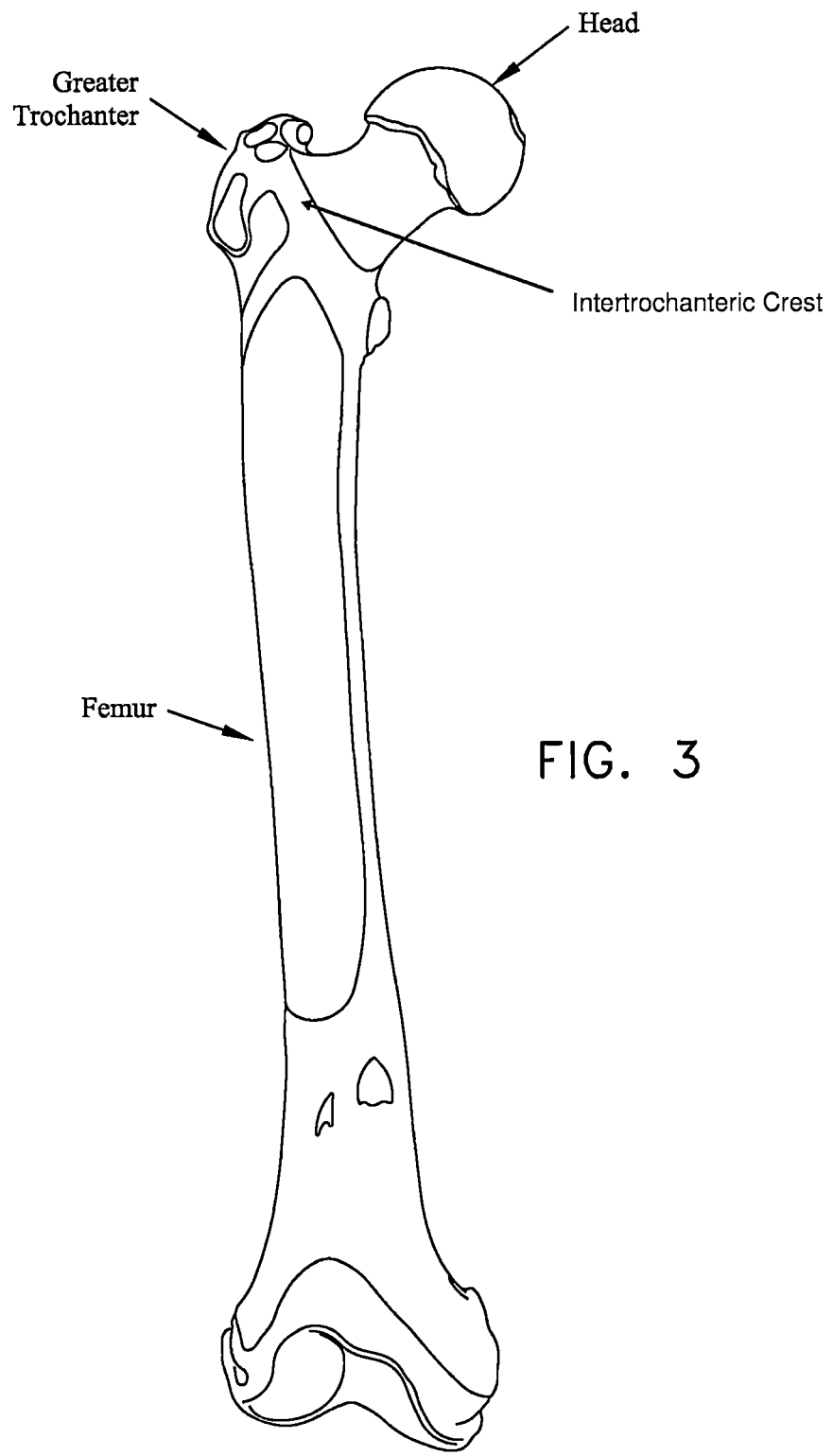
FIG. 3 is a schematic anterior view of the femur.
Figure 4:
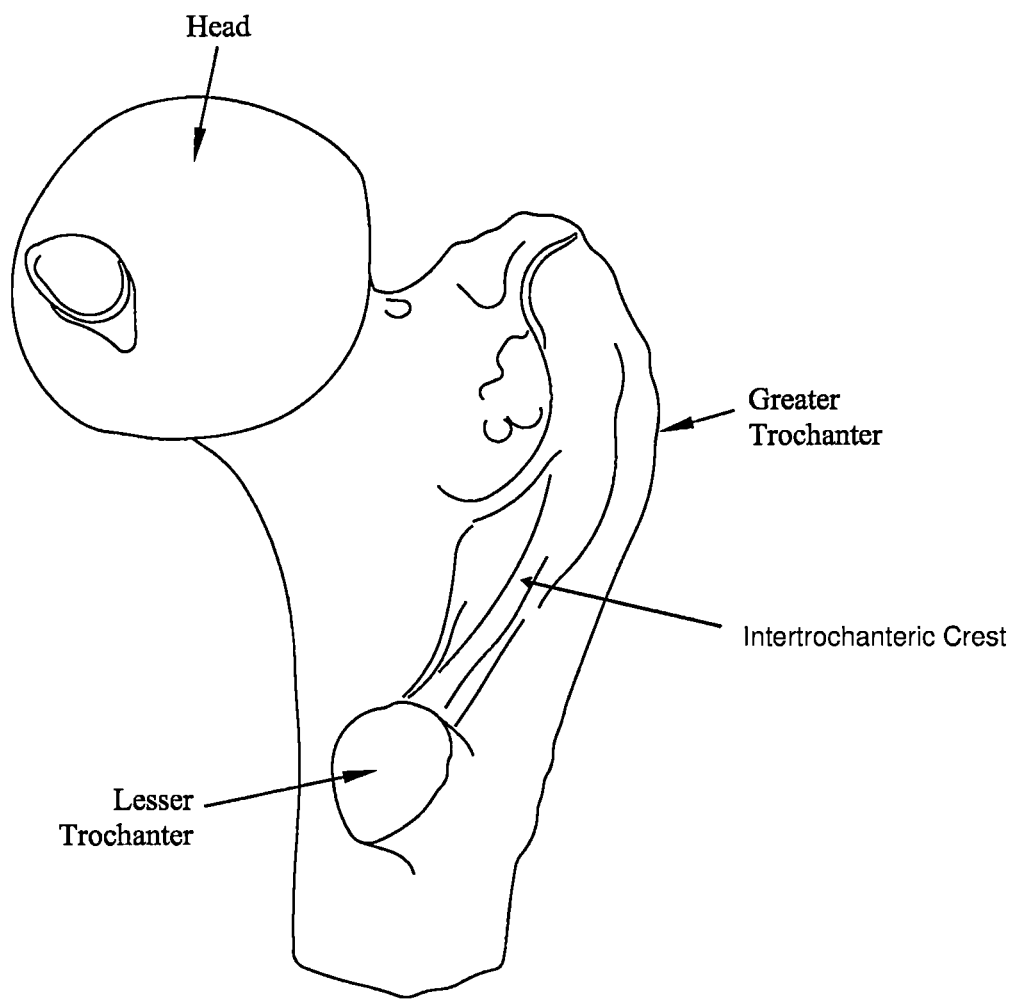
FIG. 4 is a schematic posterior view of the top end of the femur.
Figure 5:
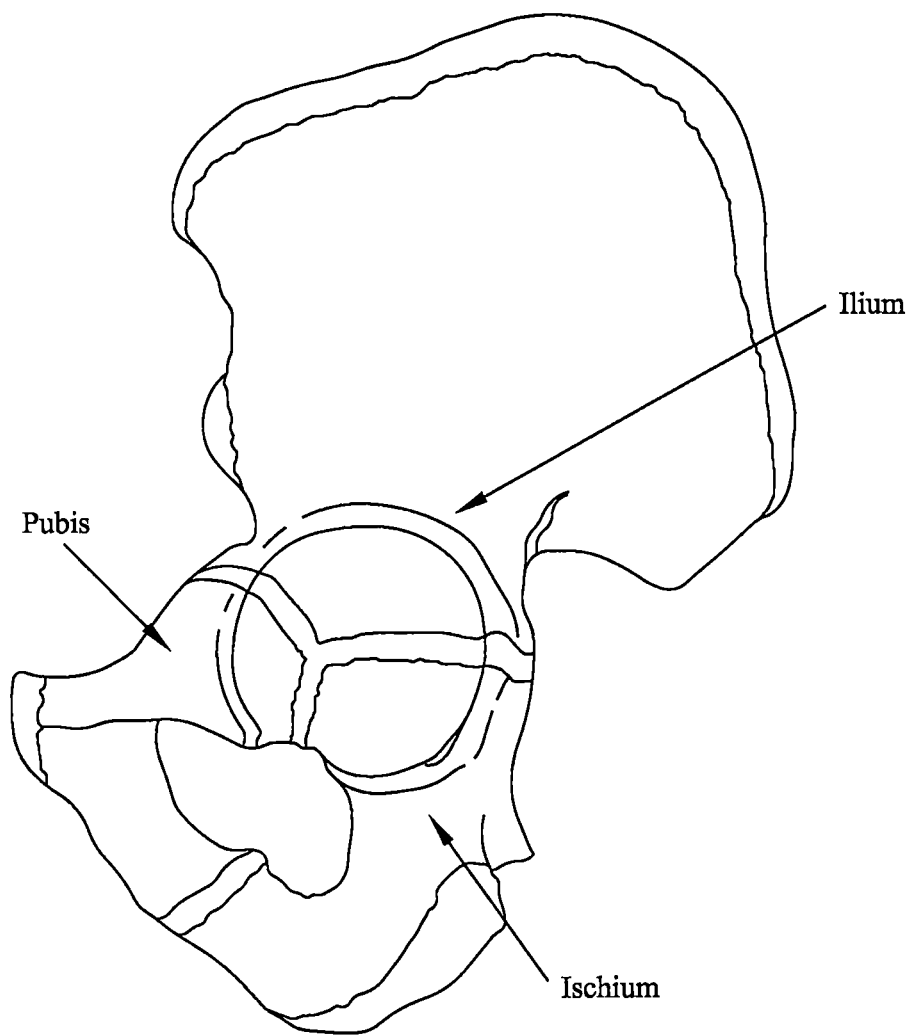
FIG. 5 is a schematic view of the pelvis.
Figure 6:
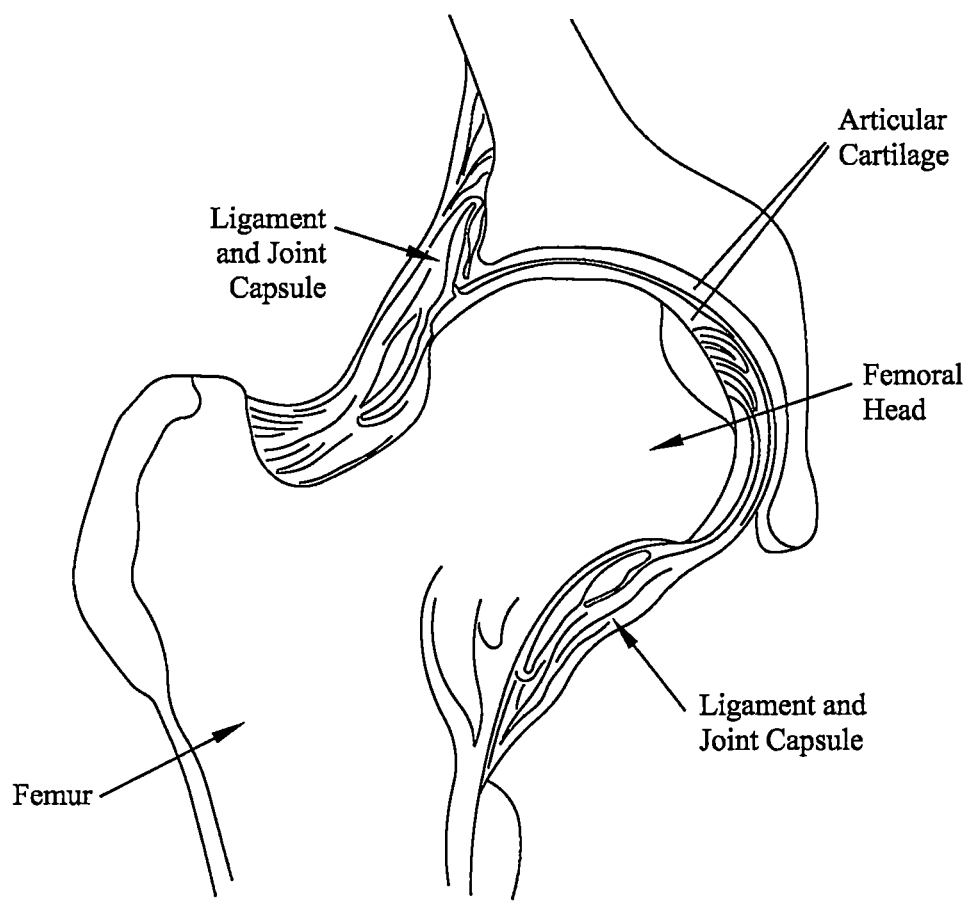
FIGS. 6-12 are schematic views showing bone and soft tissue structures in the region of the hip joint.
Figure 7:
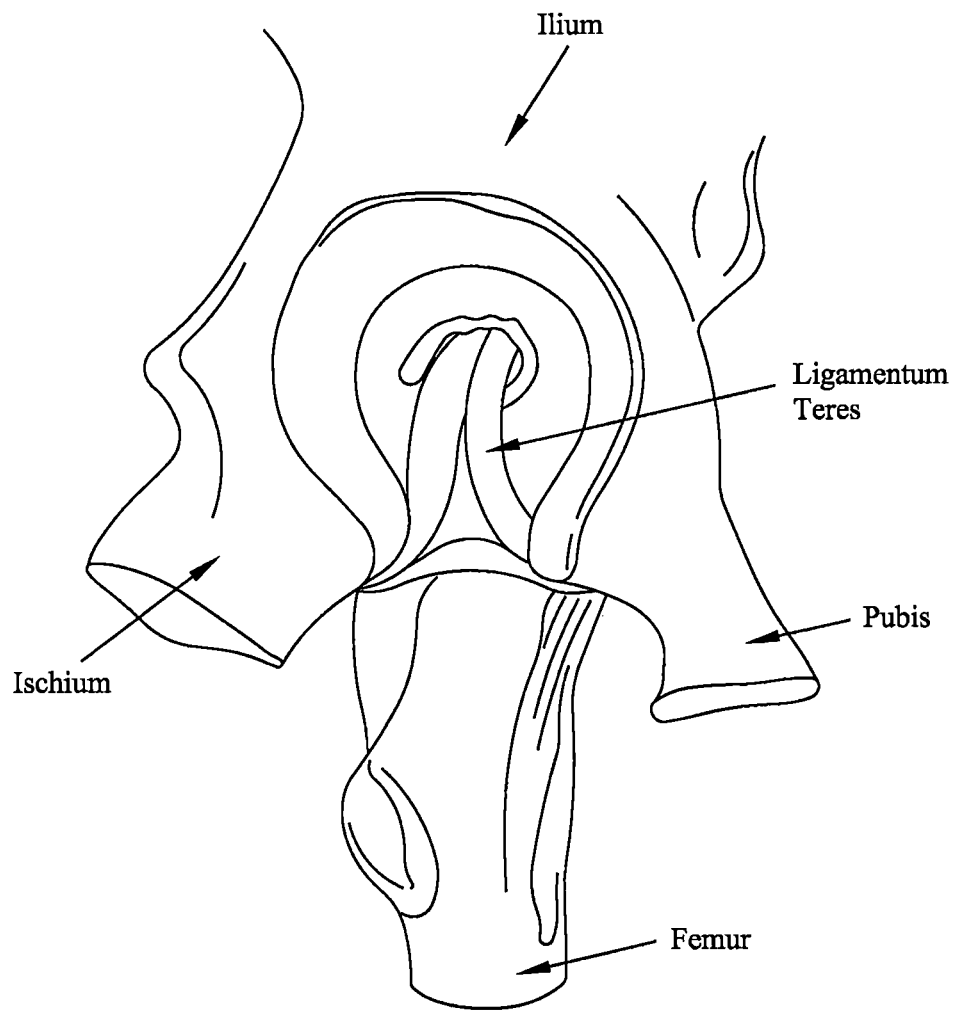

The Novel Suture Anchor System of the Present Invention in General

The present invention provides a novel method and apparatus for arthroscopically re-attaching the labrum to the acetabulum. Among other things, the present invention comprises the provision and use of a novel suture anchor system.

More particularly, and looking now at FIG. 19, there is shown a novel suture anchor system 5 for use in arthroscopically re-attaching a detached labrum to the acetabulum. Suture anchor system 5 generally comprises an anchor 10, a suture 15 secured to anchor 10, and an inserter 20 for delivering anchor 10 into the acetabulum, whereby suture 15 may be used to secure a detached labrum to the acetabular rim as will hereinafter be discussed in further detail. Suture anchor system 5 preferably also comprises a hollow guide 25 for delivering components from outside of the body to the acetabulum, and a punch (or drill) 30 which may be used to prepare a seat for anchor 10 in the acetabulum.

Looking next at FIGS. 19-23, anchor 10 comprises a generally cylindrical body 35 having a distal end 40, a proximal end 45, and a lumen 50 extending between distal end 40 and proximal end 45. In one preferred form of the present invention, lumen 50 comprises a distal end reservoir 55, a short intermediate portion 60, and an elongated proximal portion 65. As seen in FIG. 23, distal end reservoir 55 has a diameter which is greater than the diameter of short intermediate portion 60, and short intermediate portion 60 has a diameter which is greater than the diameter of elongated proximal portion 65. And in one preferred form of the present invention, the outer surface of generally cylindrical body 35 comprises a plurality of ribs 70 spaced along the length of generally cylindrical body 35, so as to enhance the "holding power" of anchor 10 in bone. In one particularly preferred form of the present invention, ribs 70 sub-divide the length of generally cylindrical body 35 into a plurality of segments, with each segment having a generally frusto-conical configuration (FIGS. 21 and 22).

Near (but spaced from) the distal end 40 of generally cylindrical body 35, there is provided a longitudinally-extending slit 75 which extends completely through one side wall (but not the other) of generally cylindrical body 35. Thus, longitudinally-extending slit 75 communicates with lumen 50 of anchor 10. The distal end of longitudinally-extending slit 75 terminates in a distal relief hole 80, and the proximal end of longitudinally-extending slit 75 terminates in a proximal relief hole 85. It will be appreciated that distal relief hole 80 is spaced from distal end 40 of generally cylindrical body 35, so that a solid distal ring 90 is located at the distal end of generally cylindrical body 35, whereby to provide the distal end of generally cylindrical body 35 with a degree of structural integrity.

Looking now at FIGS. 20 and 24-26, suture 15 generally comprises a distal loop 95 terminating in an enlargement 100 at its distal end and connected to a proximal open loop 105 at its proximal end. More particularly, distal loop 95 extends through short intermediate portion 60 and elongated proximal portion 65 of lumen 50. Enlargement 100 may comprise a solid member (e.g., cylindrical, conical, etc.) attached to the distal end of distal loop 95, or it may comprise a suture knot formed by knotting off the distal ends of distal loop 95 of suture 15, etc. Where enlargement 100 comprises a suture knot, this suture knot may or may not be hardened, shaped or stabilized with cement, heat, etc. For purposes of illustration, enlargement 100 is shown in the drawings schematically, i.e., as a generally cylindrical structure, but it should be appreciated that this is being done solely for clarity of illustration, and enlargement 100 may assume any other shapes and/or configurations (including that of a suture knot) consistent with the present invention. Enlargement 100 is sized so that it is small enough to be seated in distal end reservoir 55 of generally cylindrical body 35 (see, for example, FIGS. 24 and 25), but large enough so that it may not enter short intermediate portion 60 of generally cylindrical body 35 without causing radial expansion of generally cylindrical body 35 (see, for example, FIG. 26). Proximal open loop 105 extends back through the interior of inserter 20 (FIGS. 19 and 20) and provides a pair of free suture ends emanating from the proximal end of inserter 20 (FIG. 19), as will hereinafter be discussed.

Looking now at FIGS. 19 and 20, inserter 20 generally comprises a hollow push tube 110 having a lumen 115 extending therethrough. Inserter 20 terminates at its distal end in a drive surface 120 for engaging the proximal end 45 of anchor 10, and terminates at its proximal end in a handle 125. Handle 125 may include features to secure the free ends of suture 15, e.g., one or more suture cleats, suture slots, suture clamps, etc. Where such features are provided, and where appropriate, handle 125 may also include one or more release mechanisms to release the free ends of suture 15. Handle 125 may also have one or more mechanisms to apply tension to the secured free ends of suture 15. Suture 15 (i.e., proximal open loop 105 of suture 15) extends through lumen 115 of hollow push tube 110. By maintaining a slight proximally-directed tension on the proximal end of suture 15 (e.g., by maintaining a slight proximally-directed tension on the free suture ends of proximal open loop 105), anchor 10 can be held against the drive surface 120 of hollow push tube 110, thereby providing a degree of control for maneuvering the anchor.

Preferably anchor 10, suture 15 and inserter 20 are pre-assembled into a single unit, with suture 15 extending back through lumen 115 of inserter 20 with a slight proximal tension so as to hold anchor 10 on the distal end of inserter 20.

Suture anchor system 5 preferably also comprises a hollow guide 25 for guiding components from outside of the body to the acetabulum. More particularly, hollow guide 25 generally comprises a lumen 130 for slidably receiving anchor 10 and inserter 20 therein, as will hereinafter be discussed. The internal diameter of hollow guide 25 is preferably approximately equal to the largest external feature of anchor 10 (e.g., one or more of the barbs 70), so that anchor 10 can make a close sliding fit within the interior of hollow guide 25. Alternatively, the internal diameter of hollow guide 25 may be slightly smaller or larger than the largest external feature of anchor 10 if desired. Where suture anchor system 5 also comprises a punch (or drill) 30, lumen 130 of hollow guide is preferably sized to slidably receive punch (or drill) 30, as will hereinafter be discussed. The distal end of hollow guide 25 preferably includes a sharp tip/edge for penetrating the labrum and engaging the acetabulum, as will hereinafter be discussed.

Figure 27:
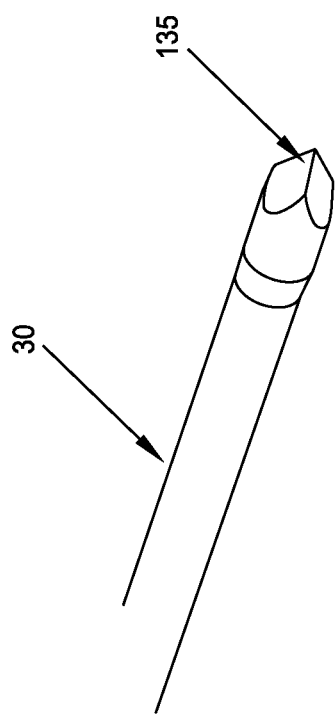

If desired, and looking now at FIGS. 19 and 27, suture anchor system 5 may also comprise a punch (or drill) 30 having a sharp distal end 135 and a proximal end 140 having a handle 145 mounted thereto. Where element 30 is a drill, handle 145 could comprise a mount for the drill so as to facilitate turning the drill with a powered driver, etc. Again, the sharp distal end 135 of punch (or drill) 30 is adapted to penetrate the acetabulum, as will hereinafter be discussed.

Method for Arthroscopically Re-Attaching the Labrum to the Acetabulum Using the Novel Suture Anchor System of the Present Invention Suture anchor system 5 is preferably used as follows to secure a detached labrum to the acetabulum.

First, the sharp distal end 136 of hollow guide 25 is passed through the labrum and positioned against the acetabulum at the location where anchor 10 is to be deployed. Preferably the sharp distal end of hollow guide 25 penetrates through the labrum and a short distance into the acetabulum so as to stabilize the hollow guide vis-à-vis the acetabulum. A stylet (e.g., an obturator) may be used to fill the hollow guide 25 during such insertion and thus prevent tissue coring of the labrum during insertion. The distal portion of the punch (or drill) 30 may also be used to fill the hollow tip of the hollow guide 25 during such insertion.

Next, if desired, punch (or drill) 30 may be used to prepare a seat in the acetabulum to receive anchor 10. More particularly, if punch (or drill) 30 is used, the sharp distal end 135 of punch (or drill) 30 is passed through hollow guide 25 (thereby also passing through the labrum) and advanced into the acetabulum so as to form an opening (i.e., a seat) in the bone to receive anchor 10. Then, while hollow guide 25 remains stationary, punch (or drill) 30 is removed from hollow guide 25.

Next, inserter 20, carrying anchor 10 thereon, is passed through hollow guide 25 (thereby also passing through the labrum) and into the seat formed in the acetabulum. As anchor 10 is advanced into the bone, the body of anchor 10 (e.g., ribs 70) makes an interference fit with the surrounding bone, whereby to initially bind the anchor to the bone. At the same time, the solid distal ring 90 located at the distal end of the anchor provides the structural integrity needed to keep the anchor intact while it penetrates into the bone. When anchor 10 has been advanced an appropriate distance into the acetabulum, the proximal end of suture 15 (i.e., proximal open loop 105) is pulled proximally while the distal end of inserter 20 is held in position, thereby causing enlargement 100 to move proximally relative to the generally cylindrical body 35, forcing the distal end of generally cylindrical body 35 to split and expand, in the manner shown in FIG. 26, whereby to further bind anchor 10, and hence suture 15, to the bone. In one preferred form of the present invention, expansion of generally cylindrical body 35 occurs along some or all of the circumference of the generally cylindrical body, and there may be variations in the amount of expansion about the circumference of the generally cylindrical body, e.g., with the construction shown in FIG. 26, there may be greater expansion in a direction perpendicular to the direction of longitudinally-extending slits 75 (for example, in the direction of the arrows shown in FIG. 26). It will be appreciated that the location and magnitude of expansion of generally cylindrical body 35 can be controlled by the number and location of longitudinally-extending slits 75, the configuration of enlargement 100, the configuration of generally cylindrical body 35 (e.g., its lumen 50 and the associated side wall of the cylindrical body 35 adjacent the lumen), etc. In one preferred form of the present invention, expansion of generally cylindrical body 35 occurs at the zone where distal end reservoir 55 meets short intermediate portion 60, with expansion occurring as enlargement 100 moves out of the comparatively larger diameter distal end reservoir 55 and into the comparatively smaller diameter intermediate portion 60.

Figure 28A:
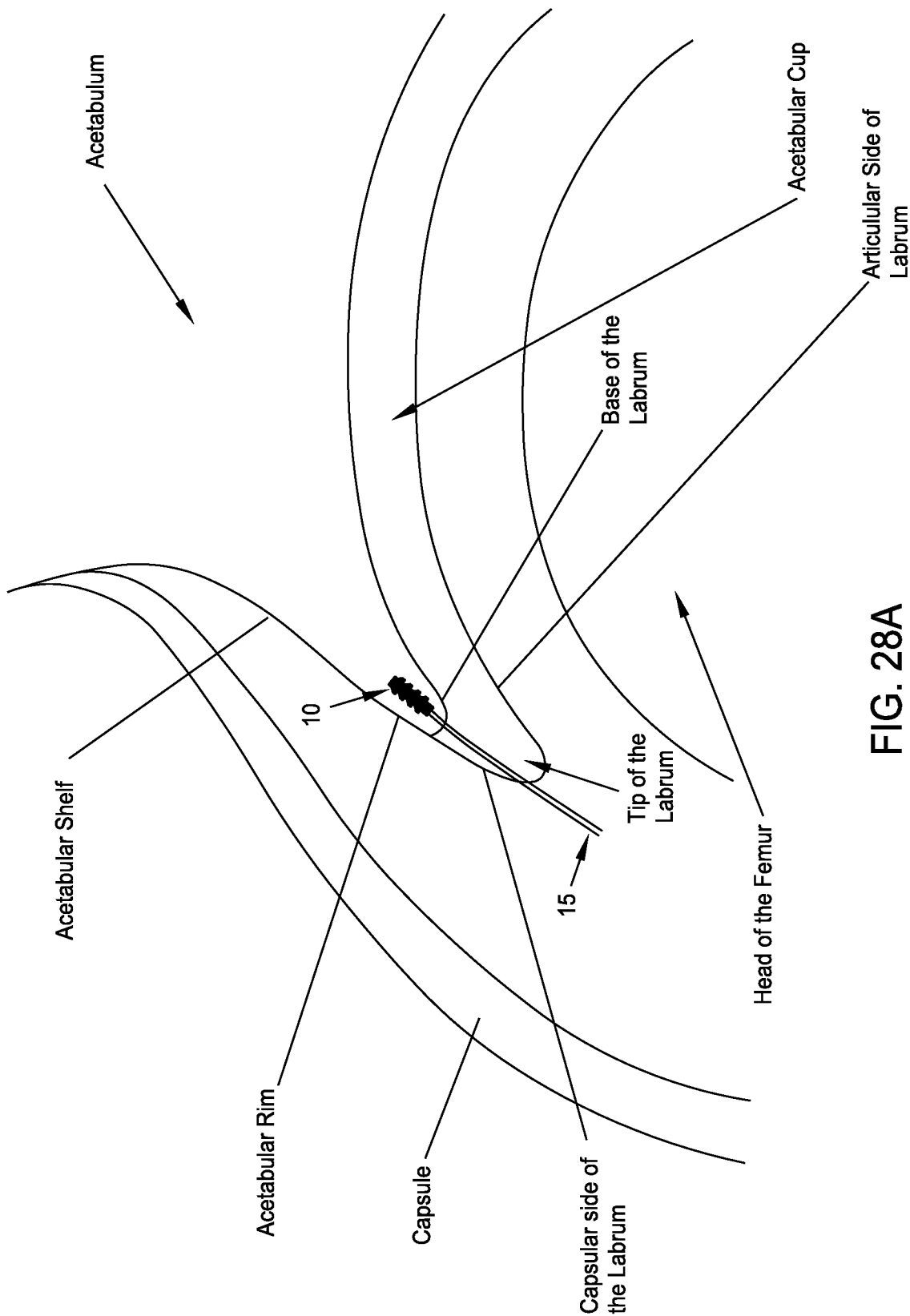

Significantly, in view of the modest holding power required to secure the labrum in place, anchor 10 can have a very small size, much smaller than a typical bone anchor of the sort used to hold a ligament in place. By way of example but not limitation, anchor 10 may have a length of 0.325 inches, an outer diameter (unexpanded) of 0.063 inches, and an outer diameter (expanded) of 0.080 inches. This small size enables a minimal puncture to be made in the labrum (and hence a minimal hole to be made in the labrum), thus reducing potential damage to the labral tissue and enabling a more accurate puncture location through the labrum. The small size of anchor 10 also allows the anchor to be placed closer to, or directly into, the rim of the acetabular cup, without fear of the anchor penetrating into the articulating surfaces of the joint. See, for example, FIG. 28, which shows anchor 10 placed close to the rim of the acetabular cup, and FIG. 28A, which shows anchor 10 placed directly into the rim of the acetabular cup. This significantly reduces, or entirely eliminates, the labrum eversion problems discussed above. Furthermore, the small size of the anchor significantly reduces trauma to the tissue of the patient.

Once anchor 10 has been set in the acetabulum, guide 25 is removed from the surgical site, leaving anchor 10 deployed in the acetabulum and suture 15 extending out through the labrum.

This process may then be repeated as desired so as to deploy additional anchors through the labrum and into the acetabulum, with each anchor having a pair of associated free suture ends extending out through the labrum.

Finally, the labrum may be secured to the acetabular cup by tying the labrum down to the acetabulum using the free suture ends emanating from the one or more anchors.

Some Alternative Constructions for the Novel Suture Anchor System of the Present Invention If desired, and looking now at FIGS. 29-31, a deployment cylinder 150 may be disposed on distal loop 95 of suture 15 just proximal to enlargement 100.

Deployment cylinder 150 can be advantageous where enlargement 100 comprises a suture knot, since the deployment cylinder can ensure the uniform application of a radial expansion force to the wall of the anchor body even where the suture knot has a non-uniform configuration. Deployment cylinder 150 may have a beveled proximal end 155 to facilitate expansion of anchor 10 when suture 15 is pulled proximally. FIG. 29 depicts anchor 10 in an unexpanded state, while FIGS. 30-31 depict the anchor 10 in an expanded state.

Furthermore, one or more of the ribs 70 may utilize a different construction than that shown in FIGS. 21-23. More particularly, in FIGS. 21-23, each of the ribs 70 comprises a proximal portion which comprises a cylindrical surface 160. Such a cylindrical surface provides increased surface area contact for engaging the adjacent bone when anchor 10 is disposed in the acetabulum. However, if desired, one or more of the ribs 70 may terminate in a sharp proximal rim 165 (FIGS. 29-31) for biting into adjacent bone when suture 15 is pulled proximally.

Figure 32:
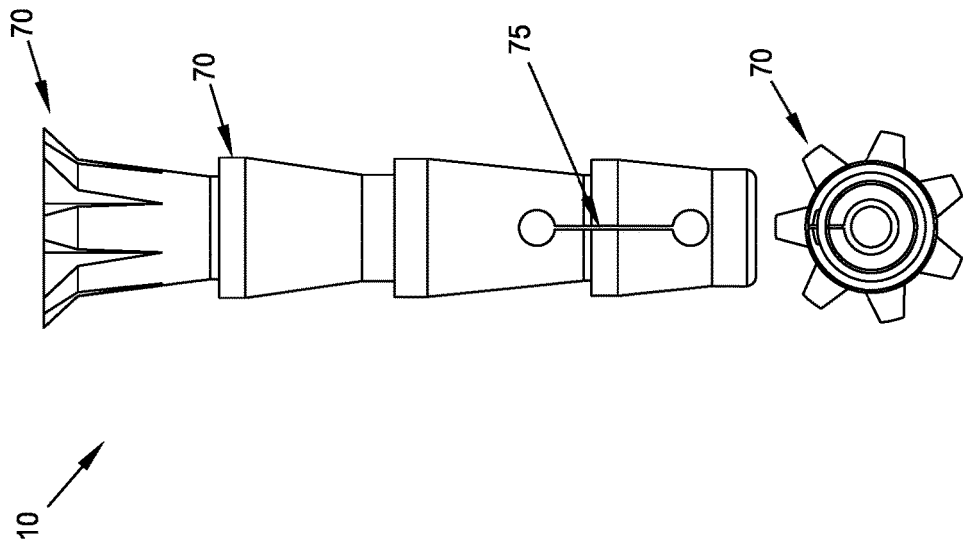
FIG. 32 is a schematic view showing another alternative form of the suture anchor system of the present invention.

Or one or more of the ribs 70 may be slotted as shown in FIG. 32 so as to provide a rib with increased flexibility. Such a construction can be useful since it allows the slotted rib 70 to be radially compressed so as to fit within inserter 20 and then radially expanded, in a spring-like manner, when deployed in the acetabulum.

Figure 35:
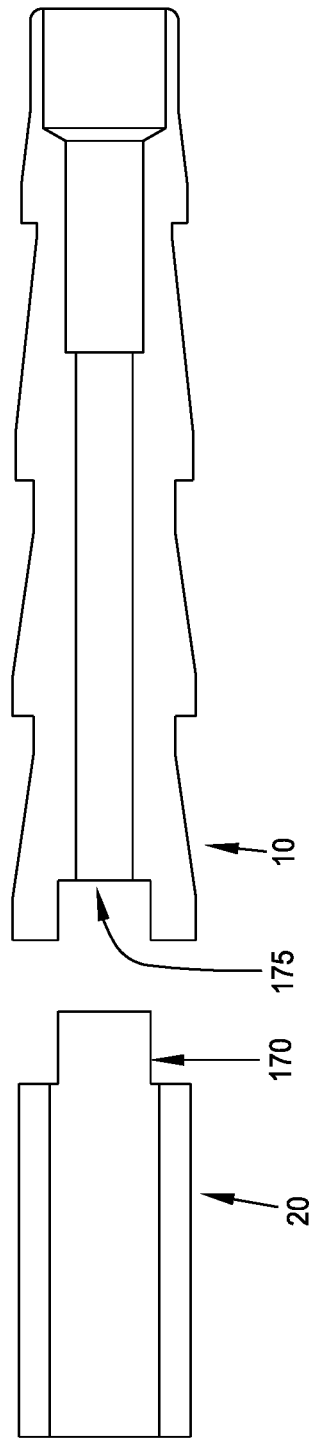
Figure 36:
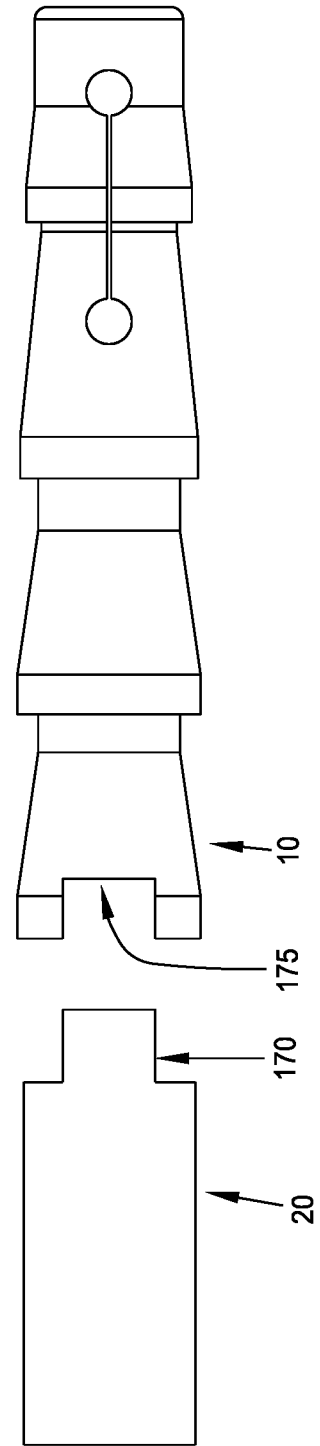
Figure 37:
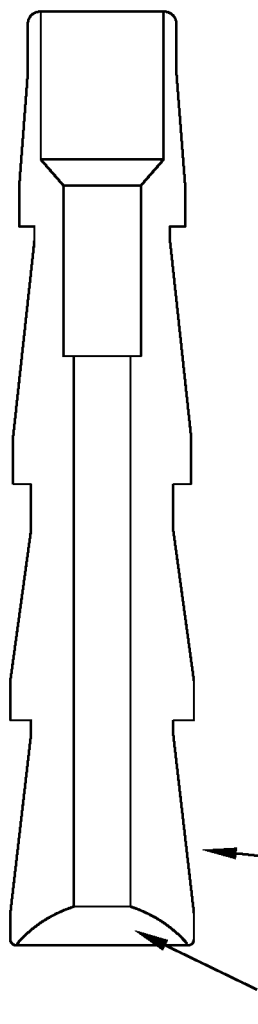
Figure 38:
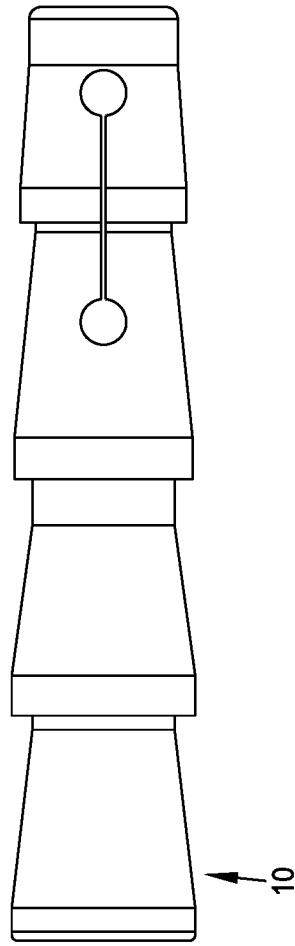

If desired, alternative arrangements can be provided for coupling anchor 10 to the distal end of inserter 20. More particularly, in FIGS. 33 and 34, a male-female connection is used to couple anchor 10 to inserter 20, with anchor 10 having a male projection 170 and inserter 20 having a corresponding female recess 175. In FIGS. 35 and 36, inserter 20 includes the male projection 170 and anchor 10 has the corresponding female recess 175. In FIGS. 37 and 38, inserter 20 has a convex surface 180 and anchor 10 has a corresponding concave surface 185. Still other constructions of this type will be apparent to those skilled in the art in view of the present disclosure.

Figure 41:
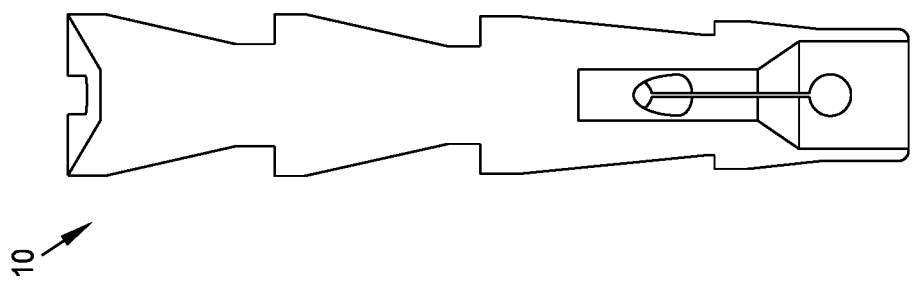
FIGS. 39-41 are schematic views showing still another alternative form of the suture anchor system of the present invention.
Figure 40:
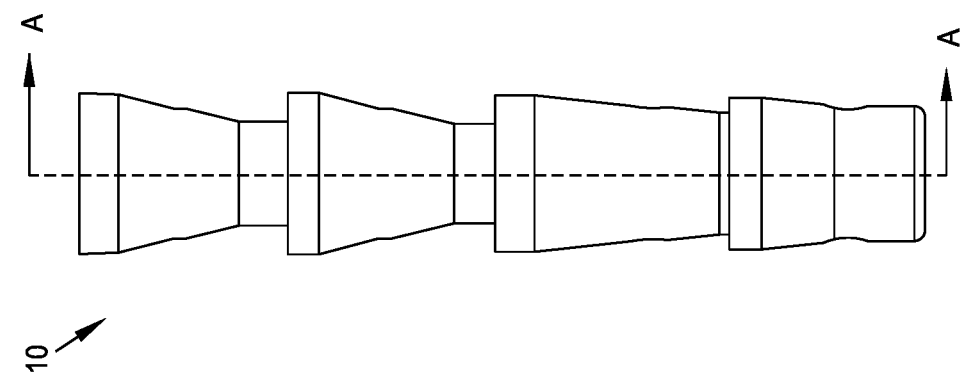
Figure 39:
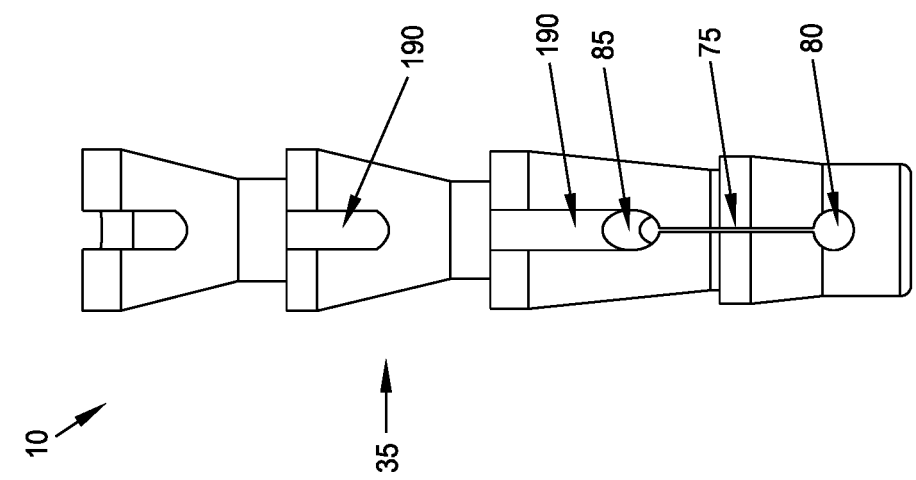

Looking next at FIGS. 39-41, in another form of present invention, suture 15 is intended to exit anchor 10 at proximal relief hole 85 and extend along the exterior of the generally cylindrical body 35. If desired, slots 190 may be provided in ribs 70 so as to accommodate suture 15 therein.

Figure 42:
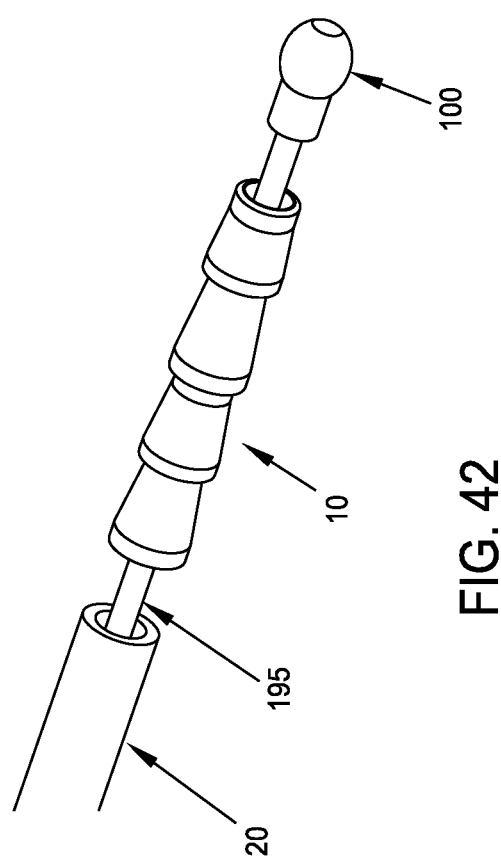
FIG. 42 is a schematic view showing yet another alternative form of the suture anchor system of the present invention.

In another form of the present invention, and looking now at FIG. 42, suture 15 can be replaced by a solid shaft 195. More particularly, solid shaft 195 extends through lumen 50 of anchor 10 and lumen 115 of inserter 20, and has enlargement 100 formed on its distal end. Proximal movement of solid shaft 195 causes enlargement 100 to expand the distal end of anchor 10 so as to cause anchor 10 to grip adjacent bone.

If desired, one or both of distal relief hole 80 and proximal relief hole 85 may be omitted, with longitudinally-extending slit 75 terminating in a blind surface at one or both ends.

Furthermore, if desired more than one longitudinally-extending slit 75 may be provided in anchor 10, e.g., two diametrically-opposed longitudinally-extending slits 75 may be provided.

Additionally, if desired, longitudinally-extending slit 75 may extend all the way to the distal end of the anchor body, rather than stopping short of the distal end of the anchor body. See, for example, FIGS. 43 and 44, which show two diametrically-opposed, longitudinally-extending slits 75, wherein the slits extend all the way to the distal end of anchor 10, and with the two figures showing exemplary rib configurations. See also FIG. 45, which shows an anchor 10 having a single longitudinally-extending slit 75, wherein the slit extends all the way to the distal end of the anchor.

Figure 48:
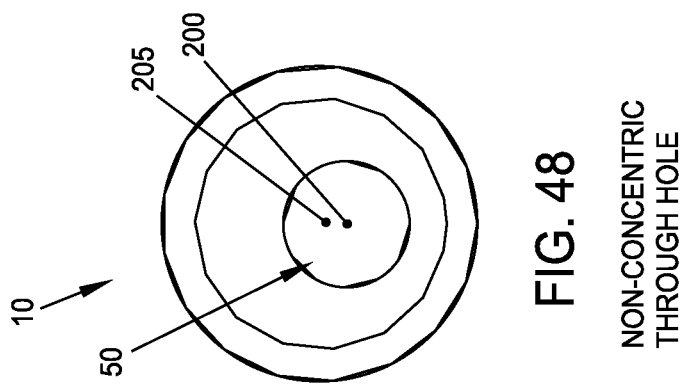
FIGS. 46-48 are schematic views showing still another alternative form of the suture anchor system of the present invention.
Figure 47:
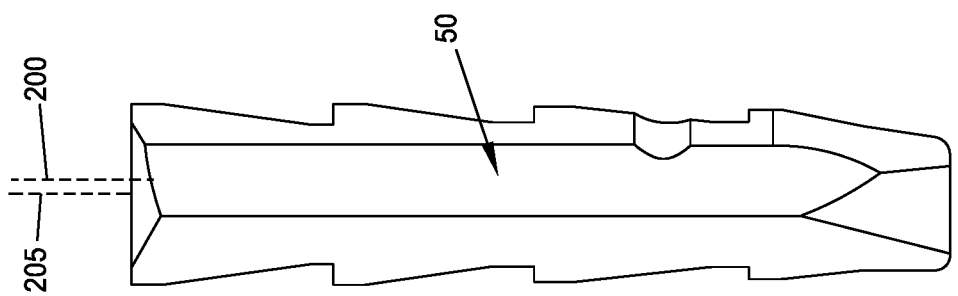
Figure 46:
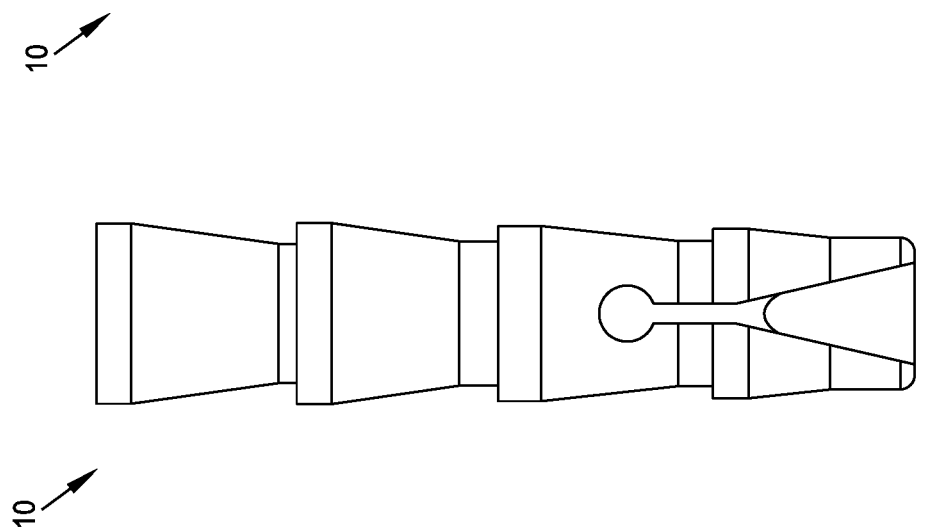

If desired, and looking now at FIGS. 46-48, lumen 50 may extend along a longitudinal axis 200 which is eccentric to the longitudinal axis 205 of generally cylindrical body 35. Such an eccentric construction can provide a thinner side wall on one side of the anchor and a thicker side wall on another side of the anchor, so as to create preferential body expansion.

Figure 49:
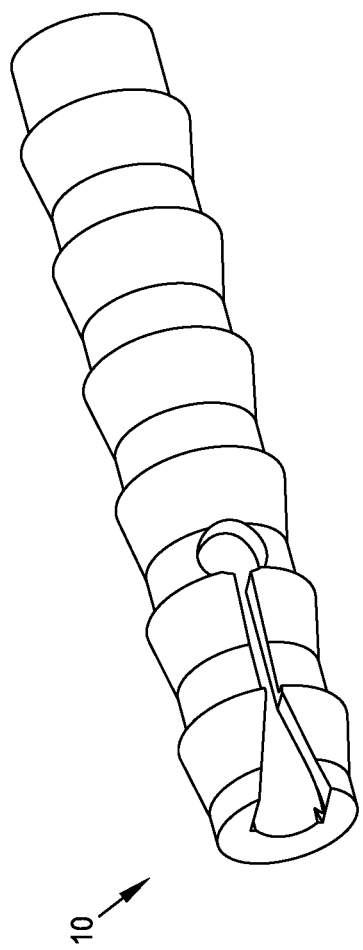
FIGS. 49-50 are schematic views showing yet another alternative form of the suture anchor system of the present invention.
Figure 50:
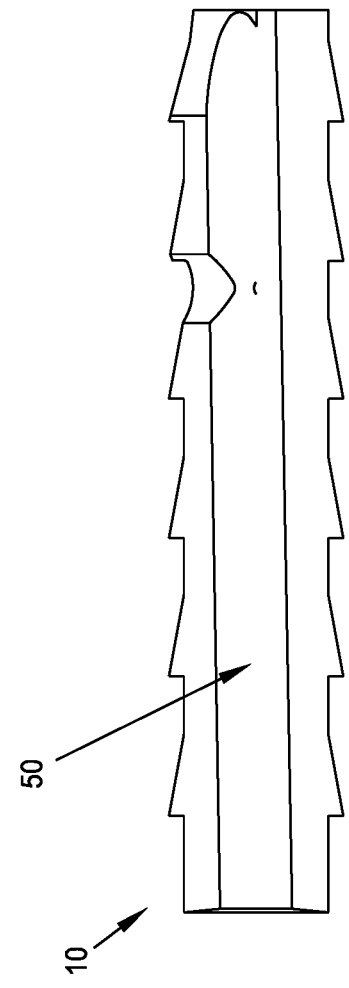

Or anchor 10 may be provided with an angled through-hole to create varying wall thicknesses and non-symmetric effects as shown in FIGS. 49 and 50.

Figure 51:
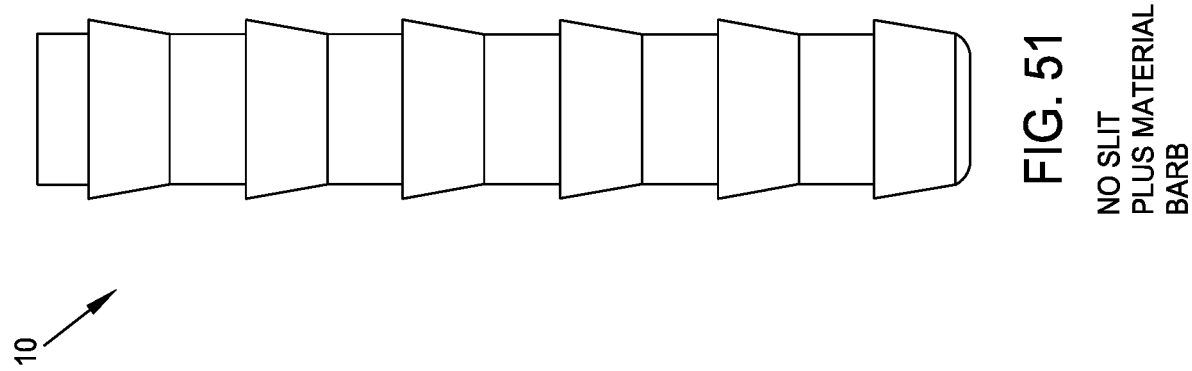
FIG. 51 is a schematic view showing another alternative form of the suture anchor system of the present invention.
Figure 55:
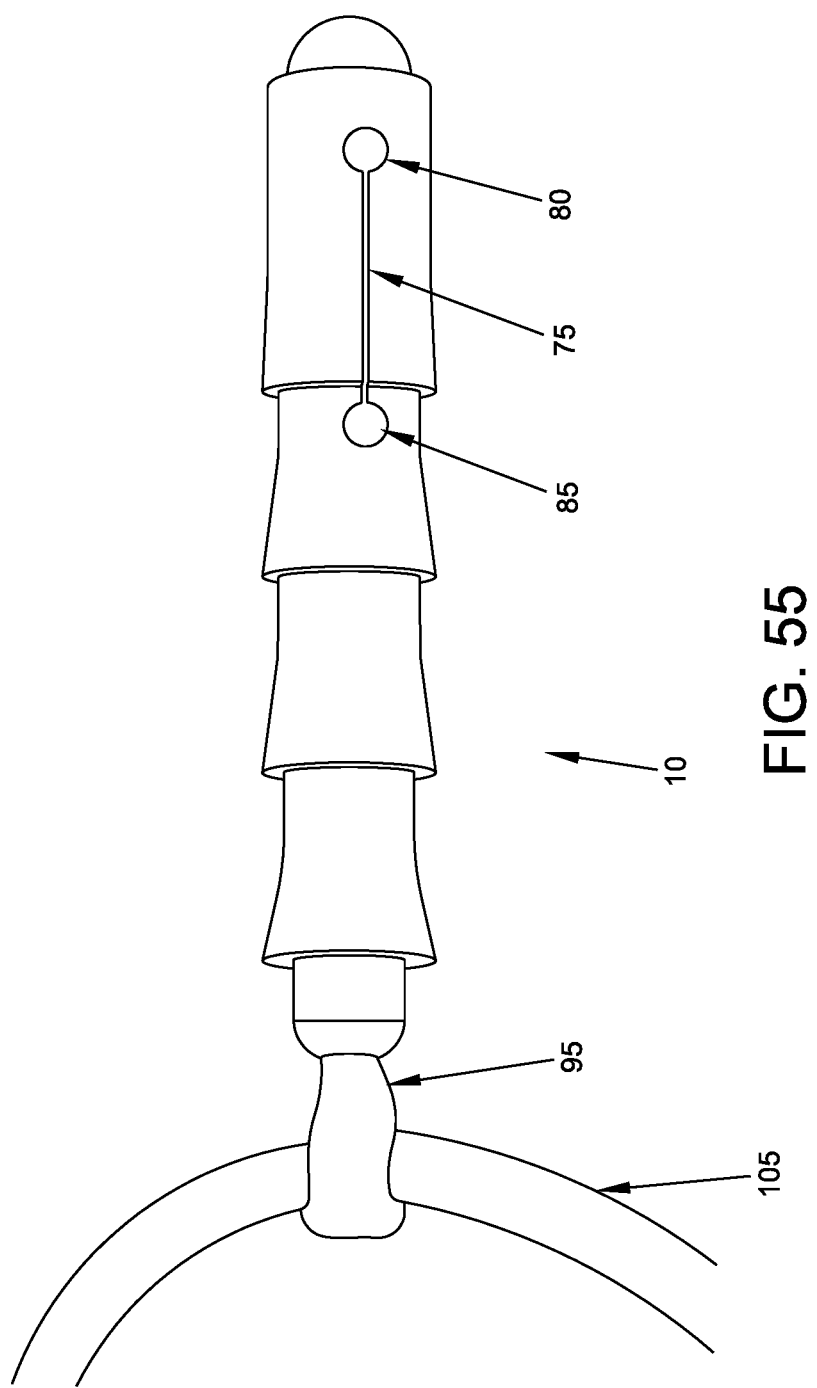
FIGS. 55-60 are schematic views showing yet another alternative form of the present invention.
Figure 56:
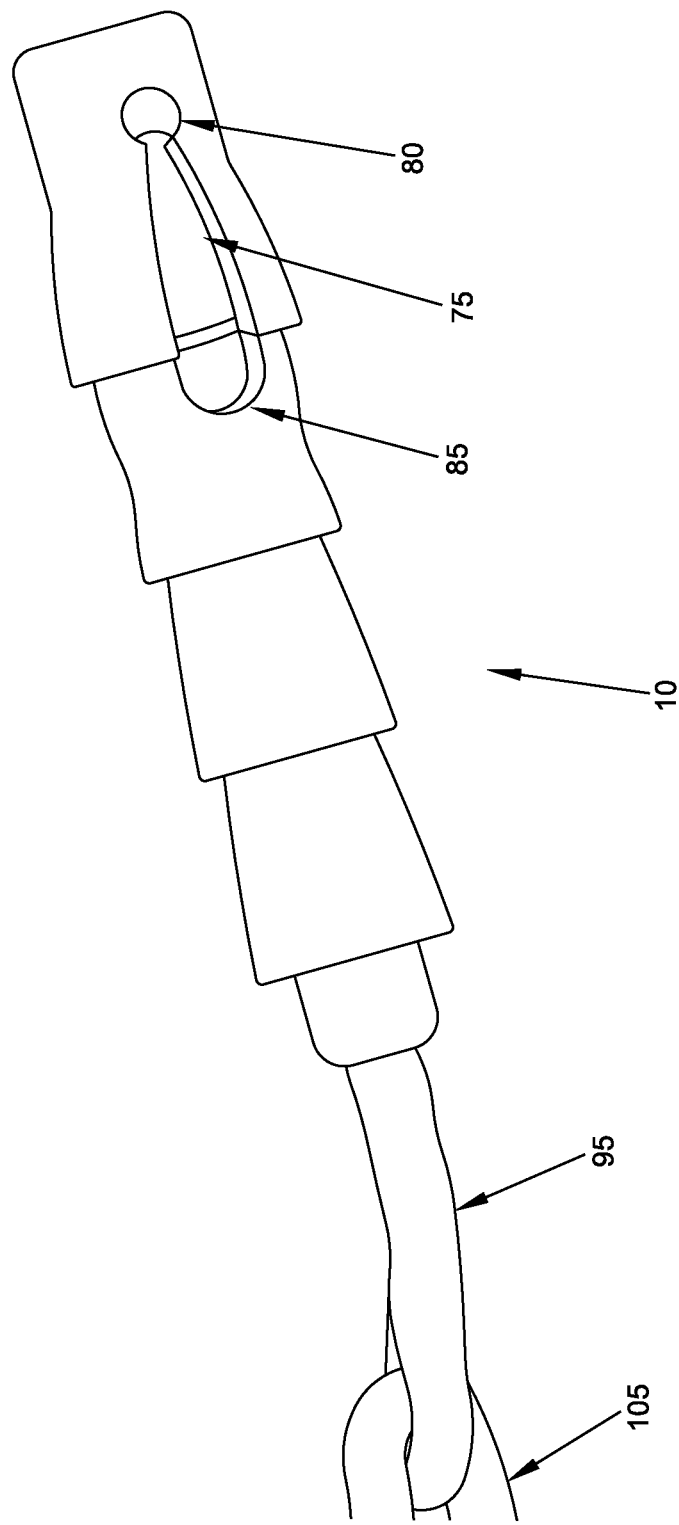
Figure 57:
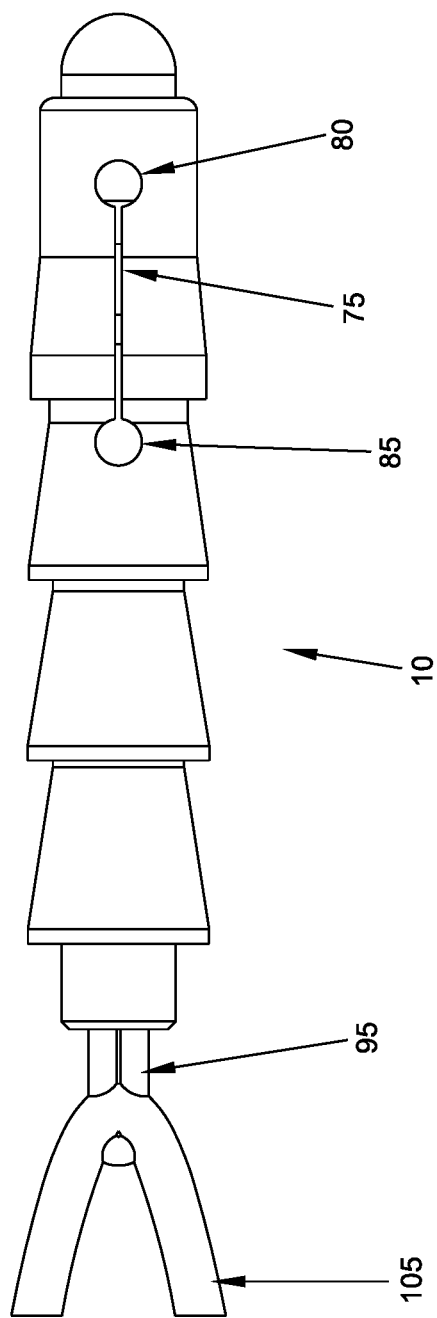
Figure 58:
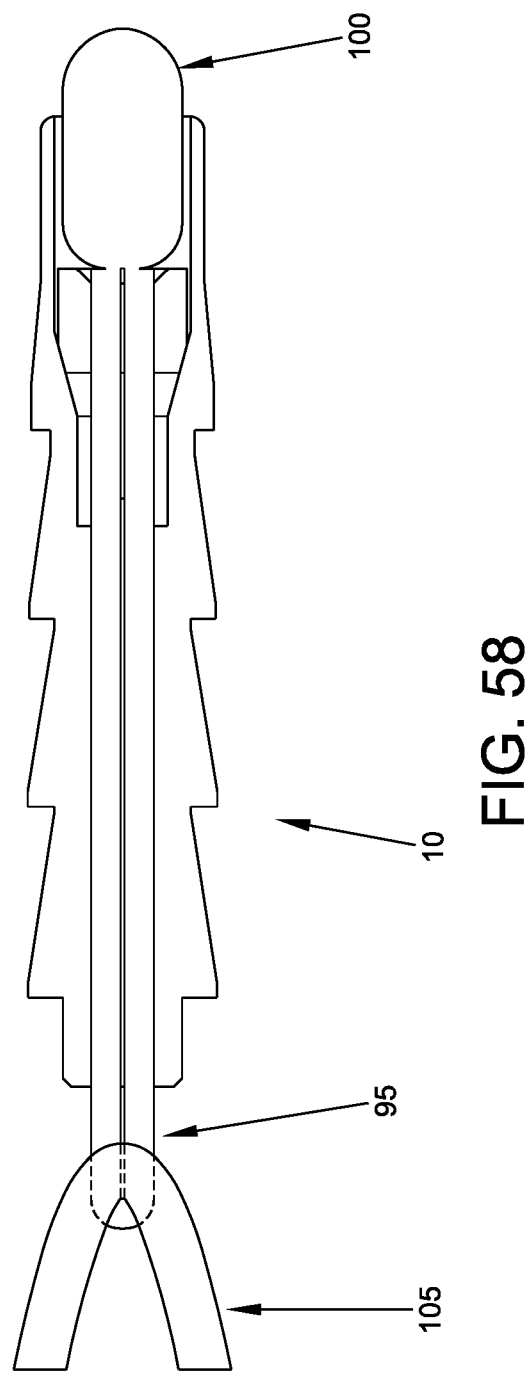
Figure 59:
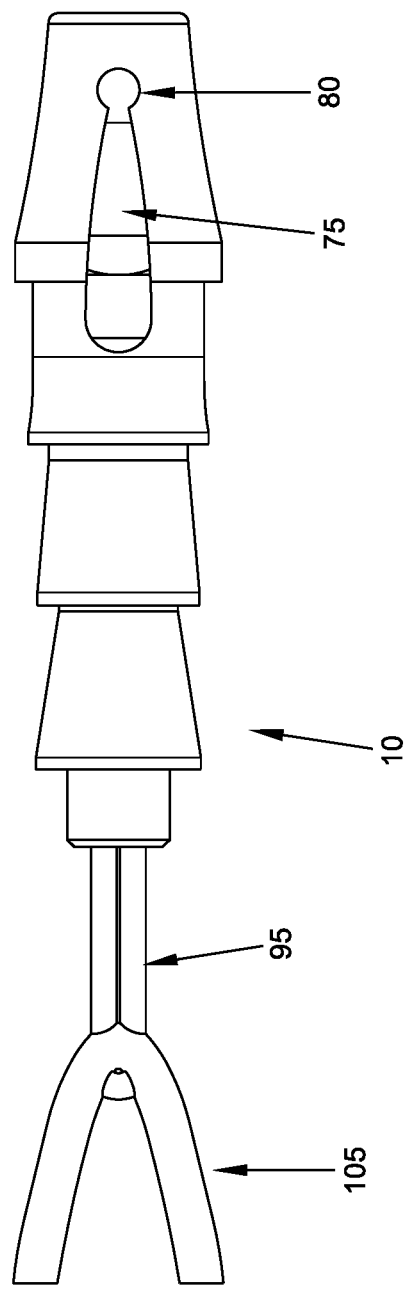
Figure 60:
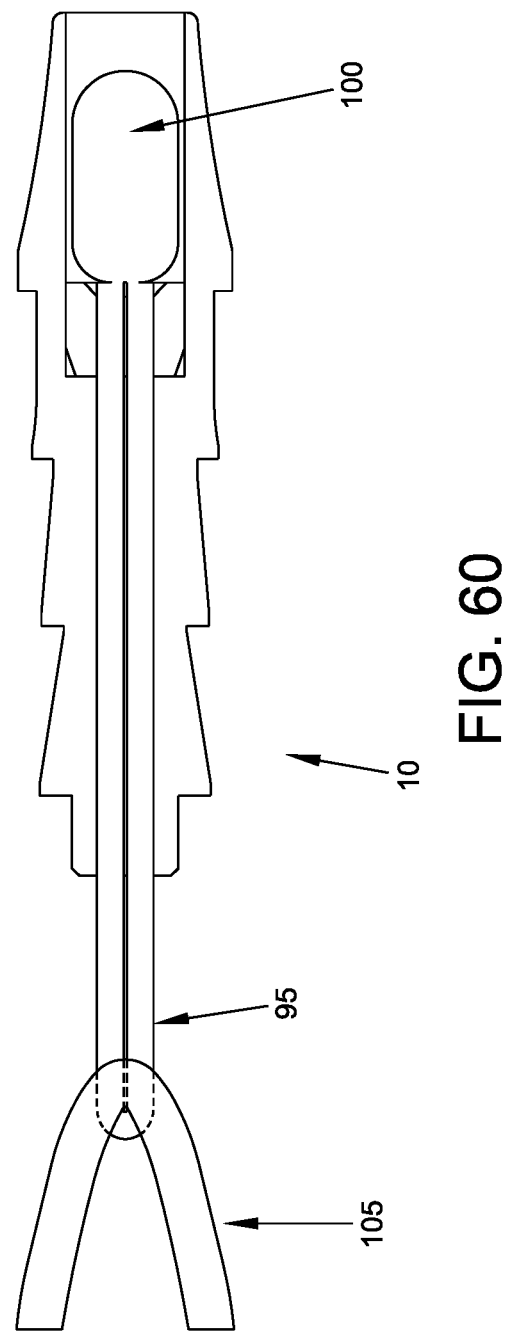
Figure 61:
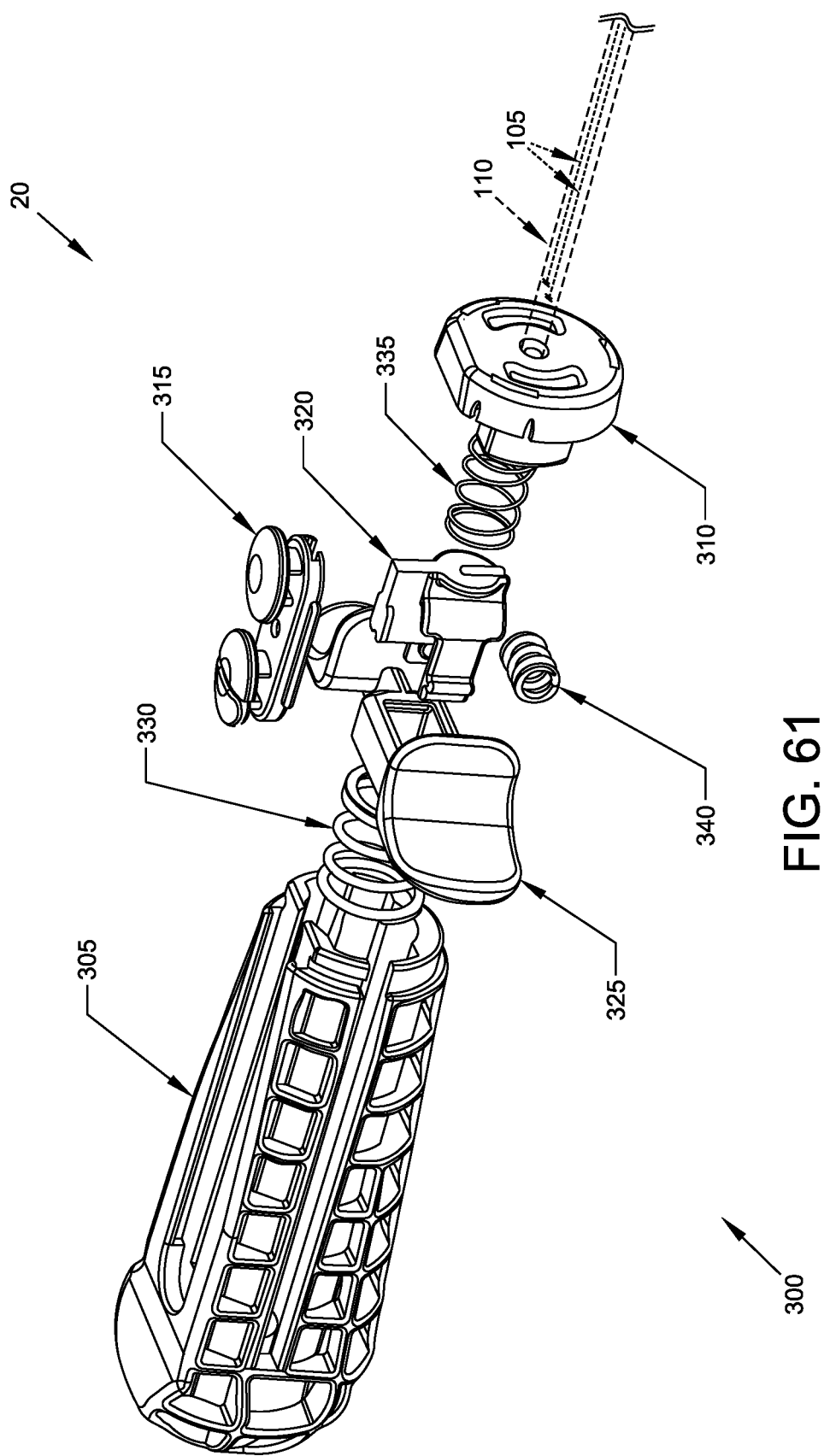
FIGS. 61-68 are schematic views showing another form of the present invention, wherein the inserter comprises a force delivery mechanism which is force-limiting so as to provide for the controlled delivery of an actuation force to the anchor, and further wherein the force delivery mechanism comprises a wishbone force delivery mechanism (note that in FIGS. 62-64 and 67, only one suture strand is shown for clarity of illustration)

If desired, and looking now at FIG. 51, anchor 10 can be constructed so that longitudinally-extending slit 75 is omitted entirely. In this form of the invention, anchor 10 is preferably formed with one or more thin-walled sections 210 (FIGS. 52-54) which fracture when enlargement 100 is forced proximally.

Alternatively, in another form of the invention, anchor 10 is constructed so that its generally cylindrical body 35 expands radially when enlargement 100 moves proximally, but the distal end of the anchor does not split open. See FIGS. 55-60. Again, the direction and extent of the expansion of cylindrical body 35 may be controlled by the number and location of the longitudinally-extending slits 75, the configuration of enlargement 100, the configuration of generally cylindrical body 35 (e.g., its lumen 50 and the associated side wall of the cylindrical body 35 adjacent the lumen), etc.

Additional Construction Details

Anchor 10 can be made out of any material consistent with the present invention, e.g., anchor 10 can be made out of a biocompatible plastic (such as PEEK), an absorbable polymer (such as poly-L-lactic acid, PLLA), bio-active materials such as hydrogels, or metal (such as stainless steel or titanium).

Suture 15 can be made out of any material consistent with the present invention, e.g., common surgical suture materials. One such material is woven polymer such as PE or UHMWPE. Another material is a co-polymer material such as UHMWPE/polyester. Yet another material is an absorbable polymer such as polyglycolic acid, polylactic acid, polydioxanone, or caprolactone. Proximal loop 105 is preferably a #1 suture size; alternatively, it is a #2 suture size, a #0 suture size, or a #2-0 suture size. Distal loop 95 is preferably a #2-0 suture size; alternatively, it is a #2 suture size, a #1 suture size, or a #0 suture size.

Figure 8:
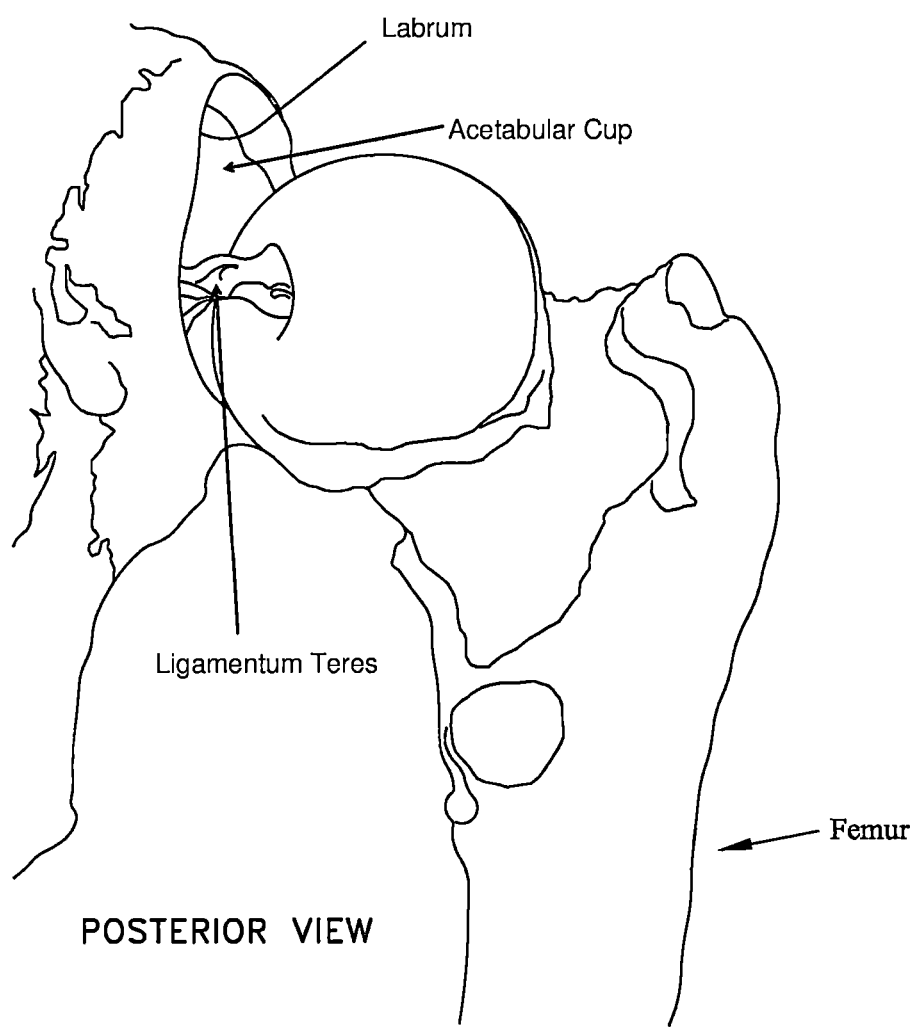
Figure 9:
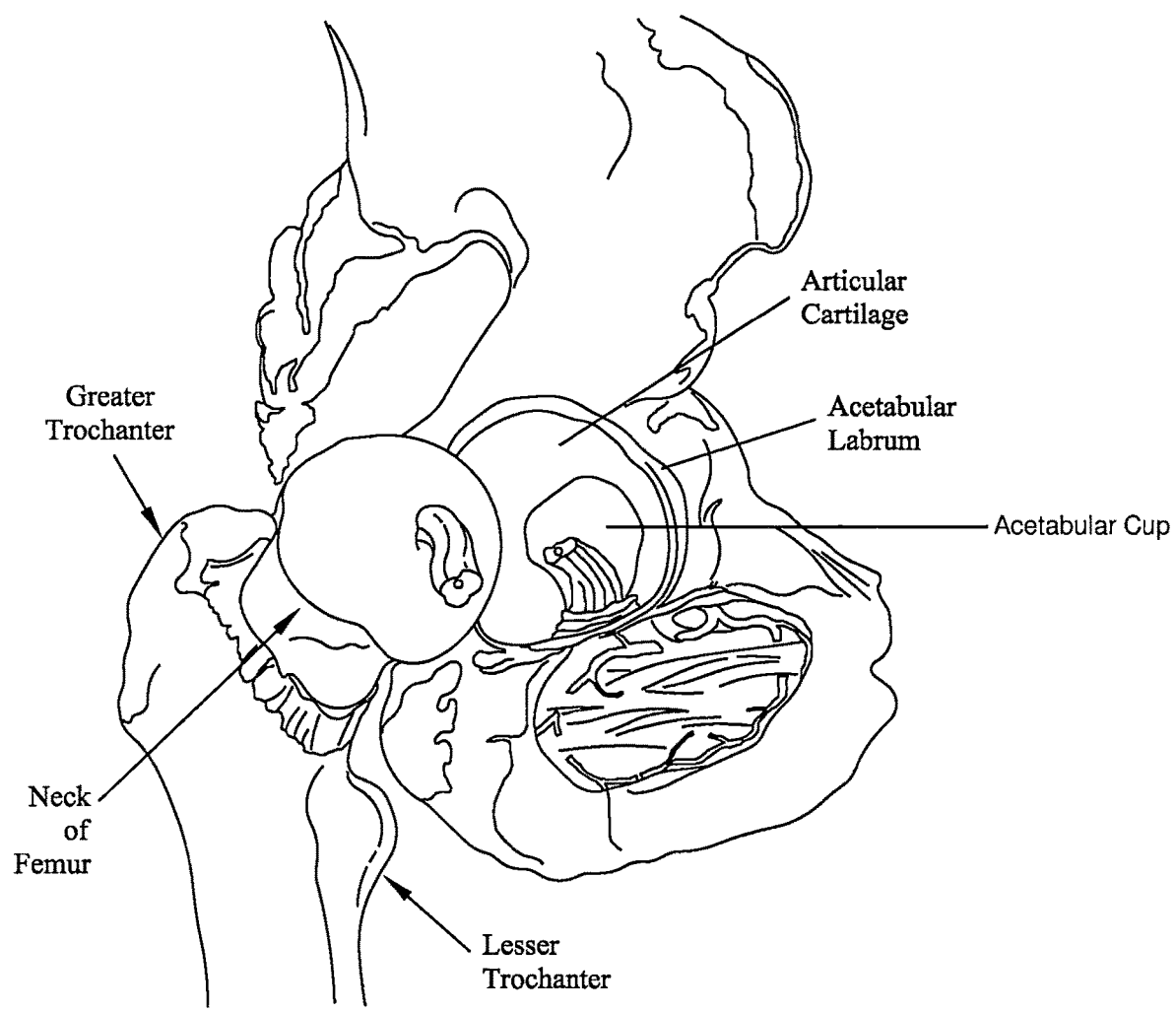
Figure 10:
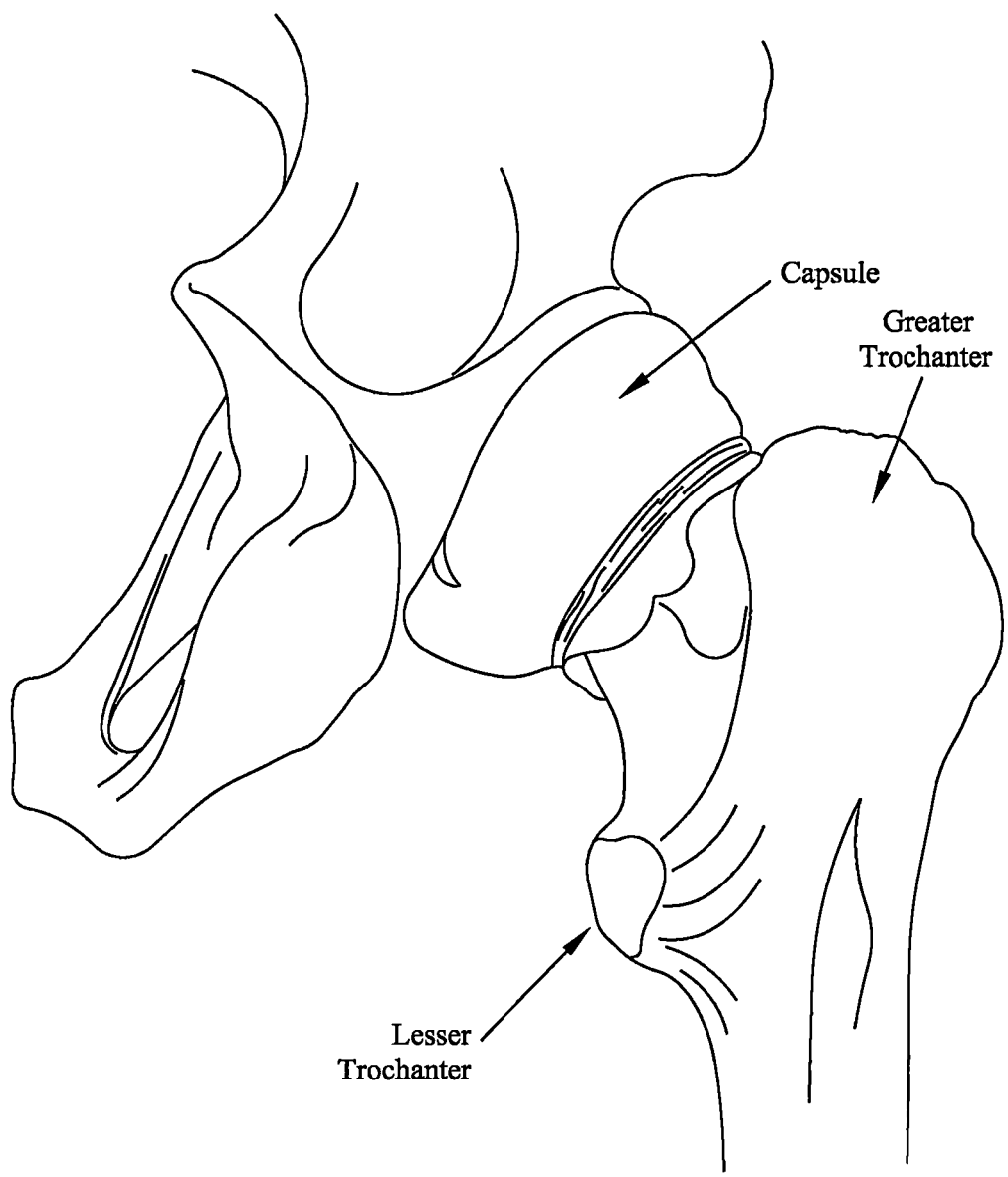
Figure 11:
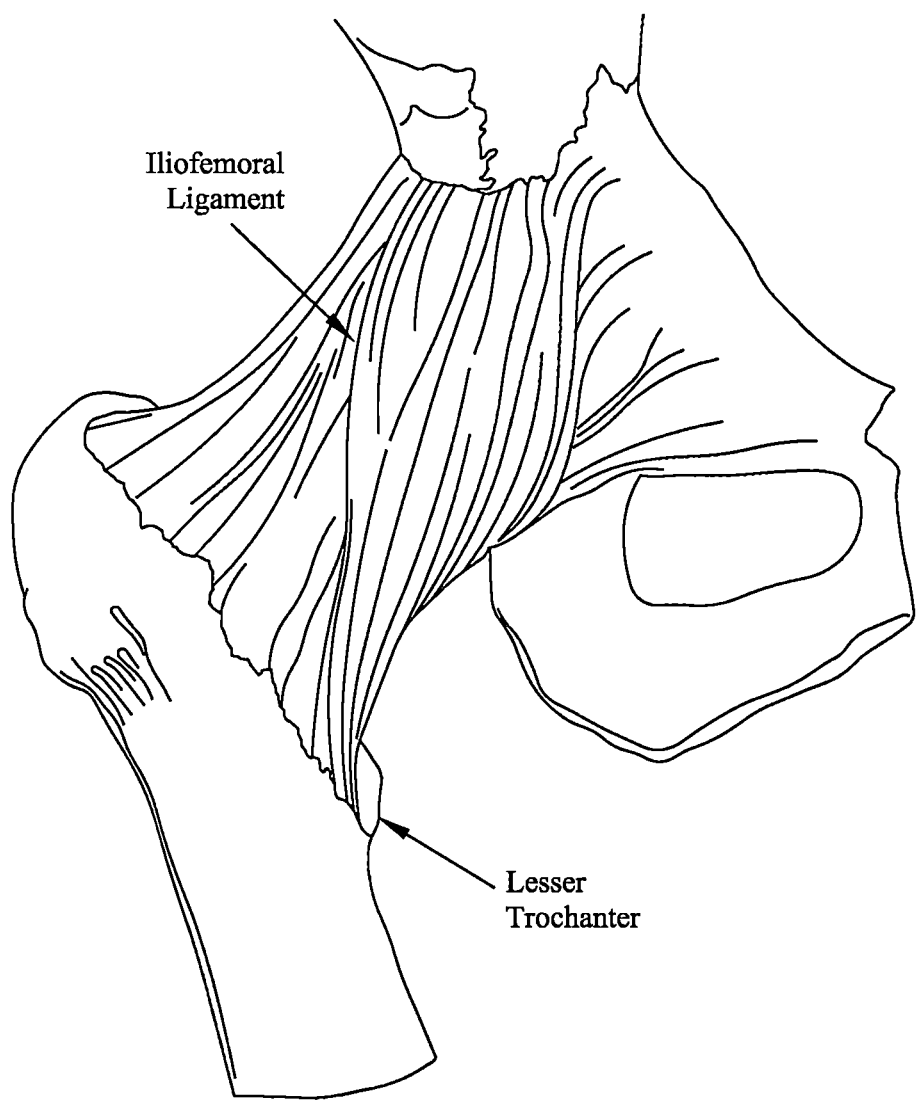
Figure 12:
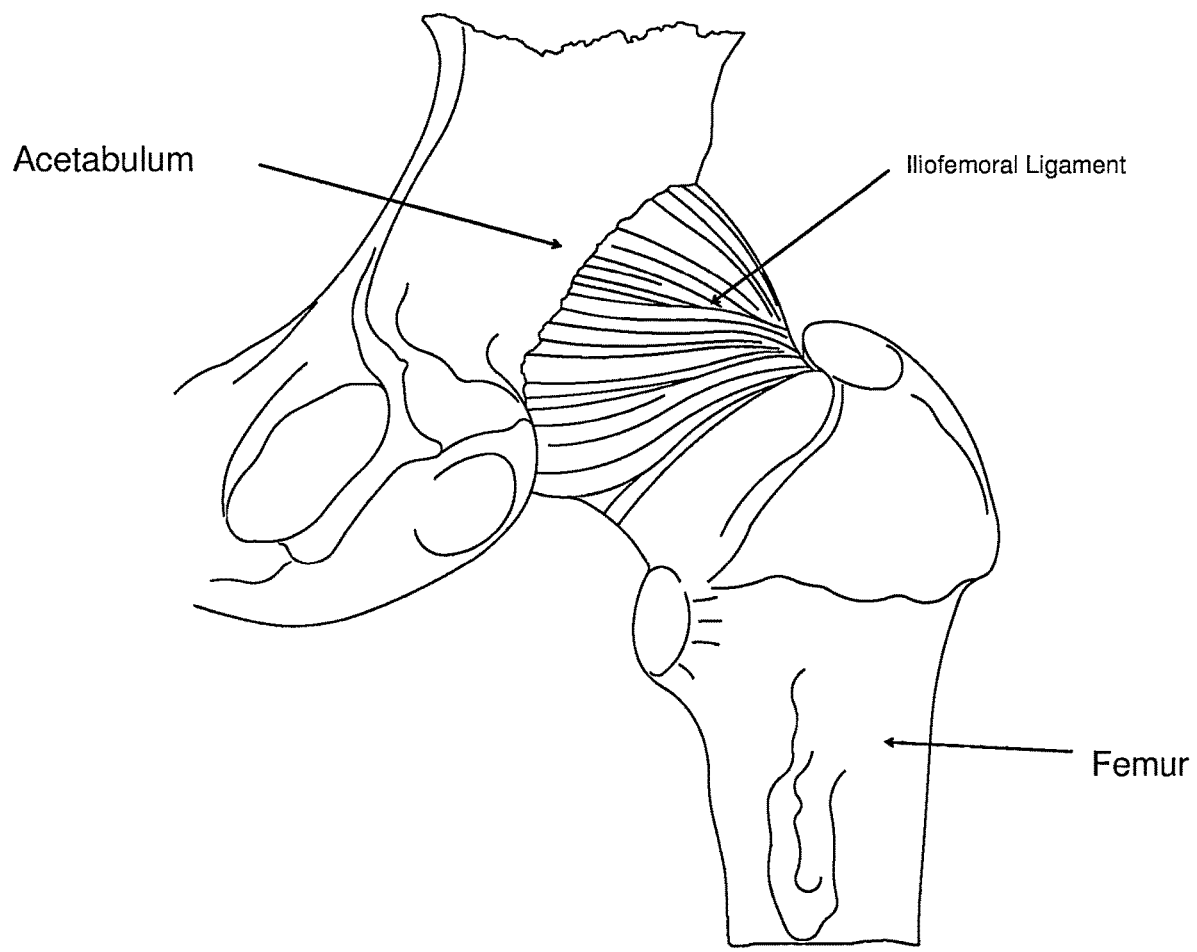
Figure 15:
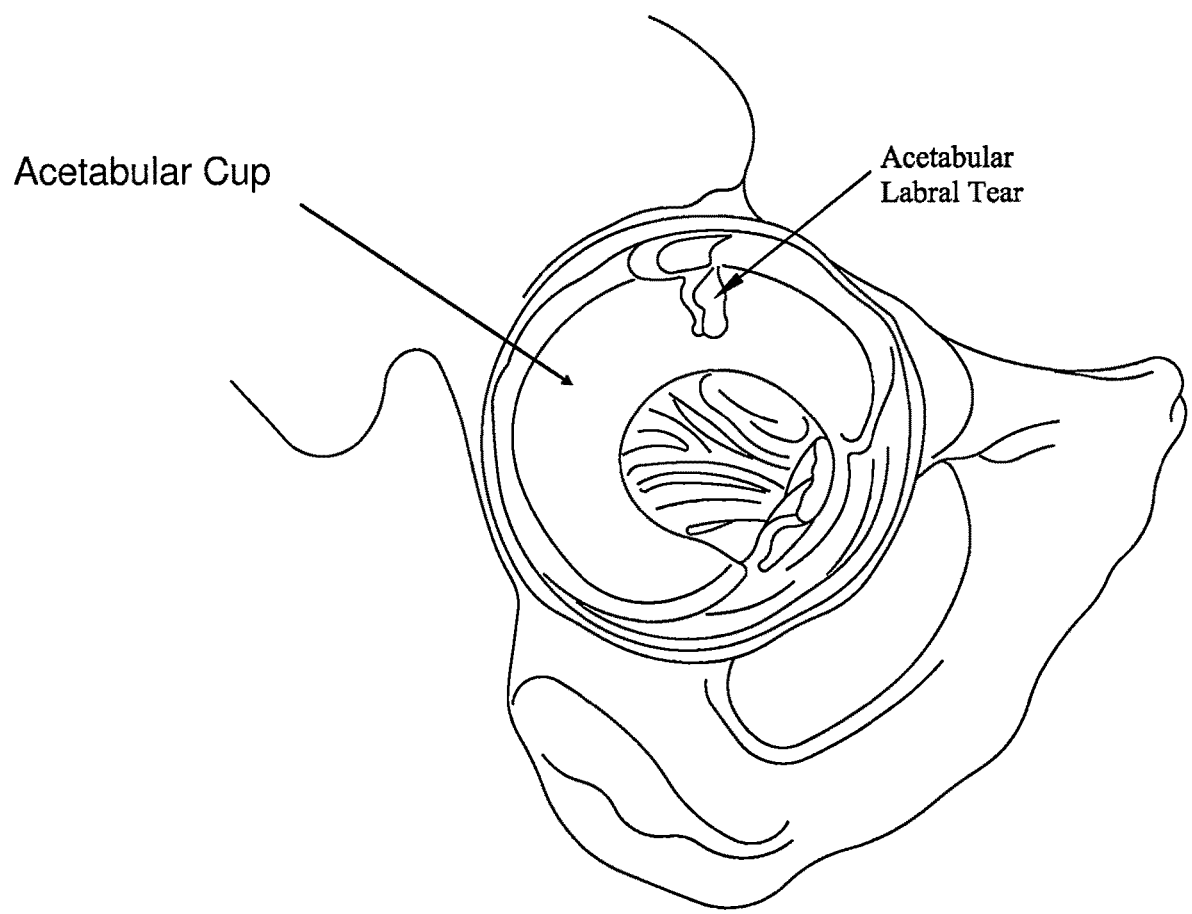
FIG. 15 is a schematic view showing a labral tear.
Figure 16:
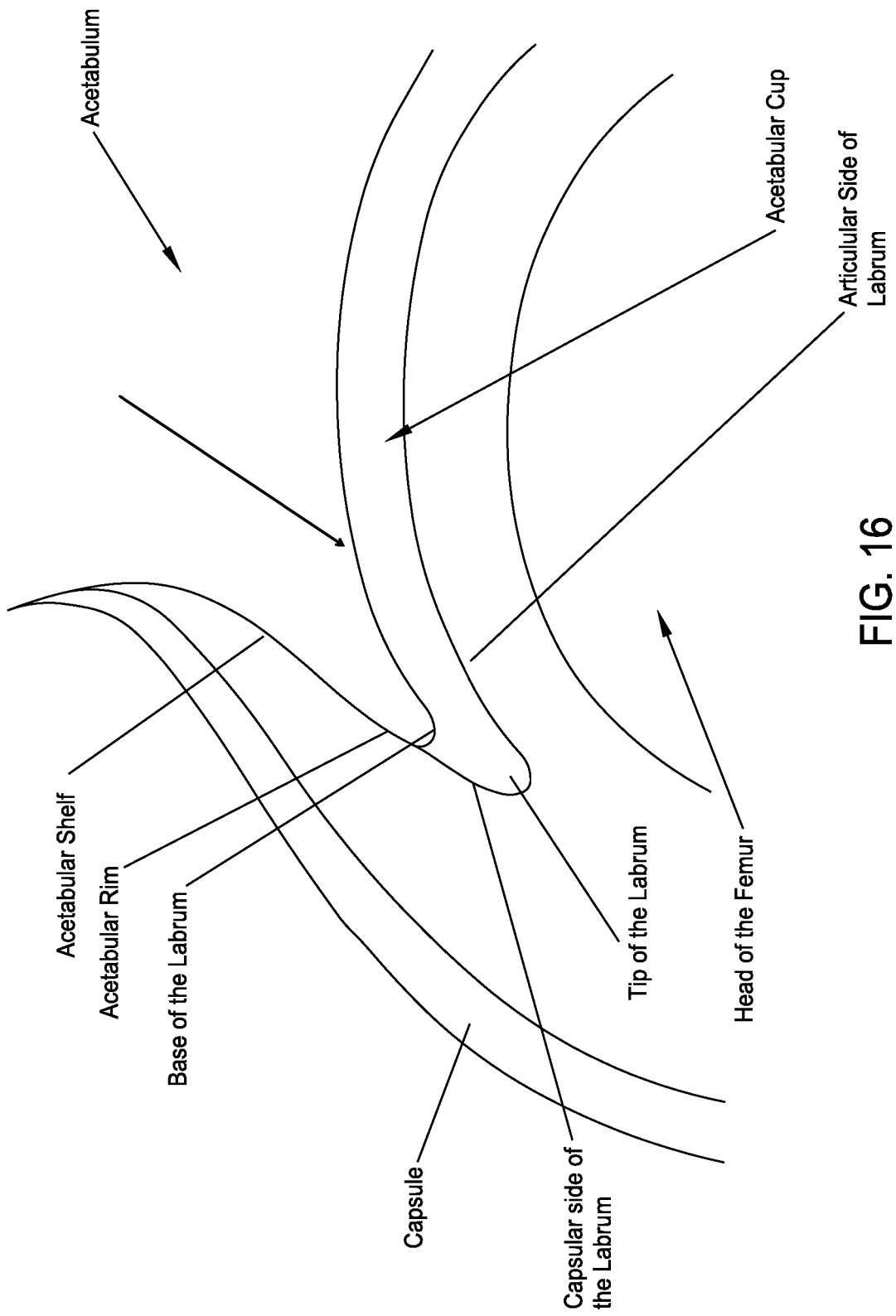
FIG. 16 is a schematic view showing a normal labrum which has its base securely attached to the acetabulum.
Figure 17:
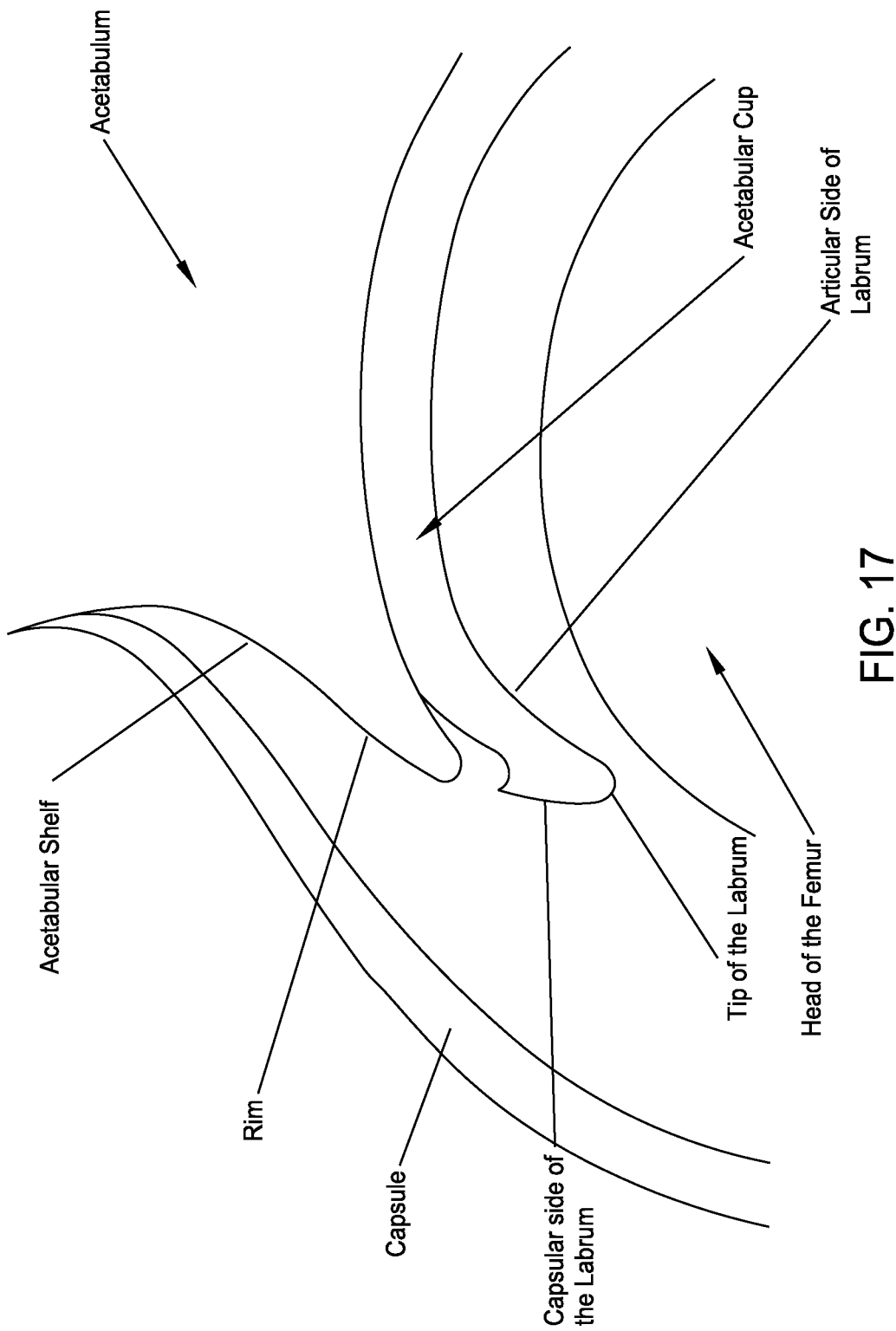
FIG. 17 is a schematic view showing a portion of the labrum detached from the acetabulum.
Figure 18:
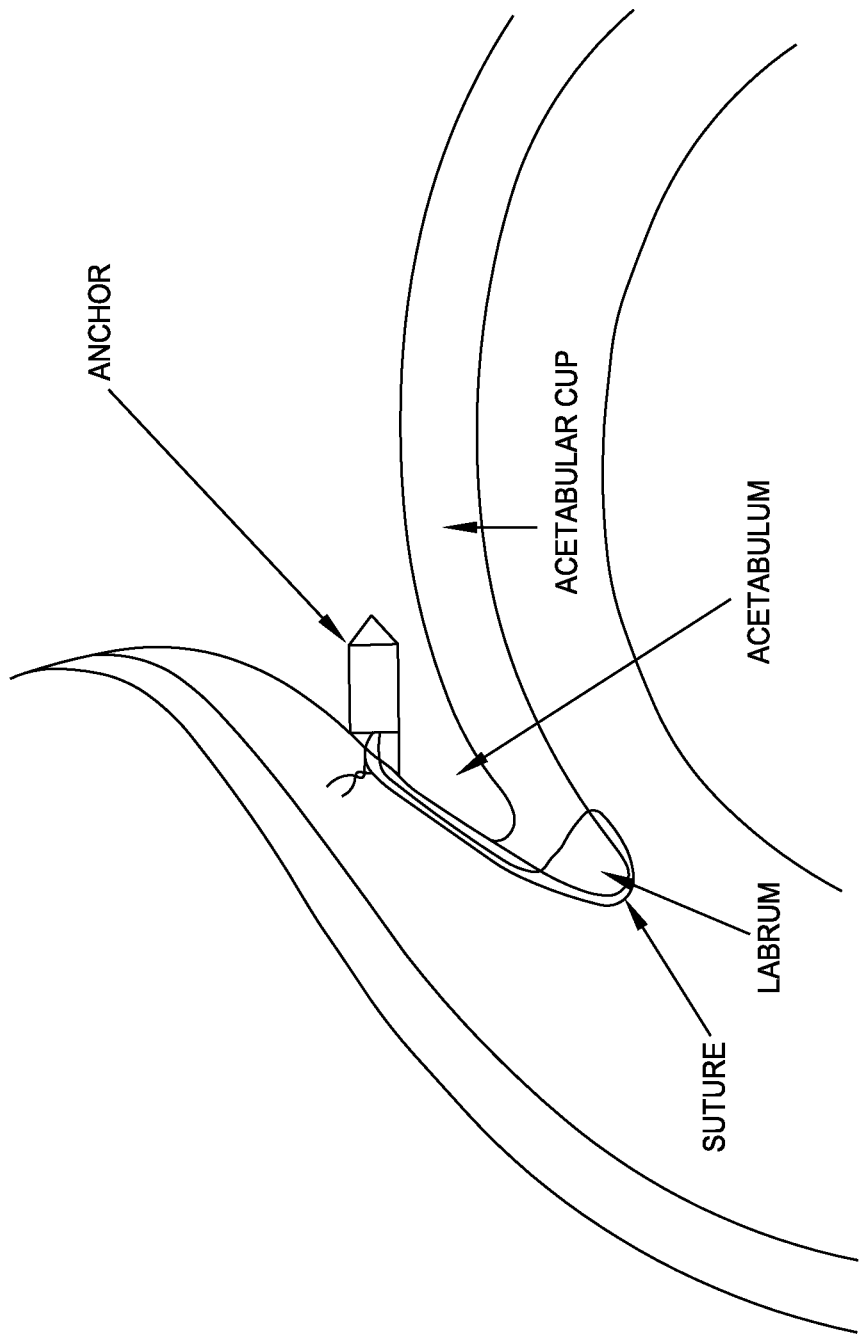
FIG. 18 is a schematic view showing a bone anchor being used to re-attach the labrum to the acetabulum.
Figure 26:
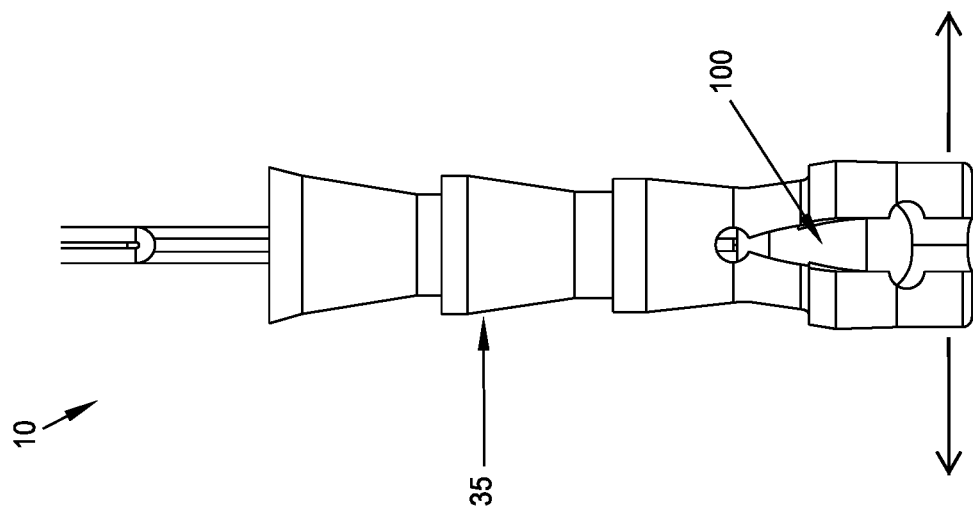
Figure 25:
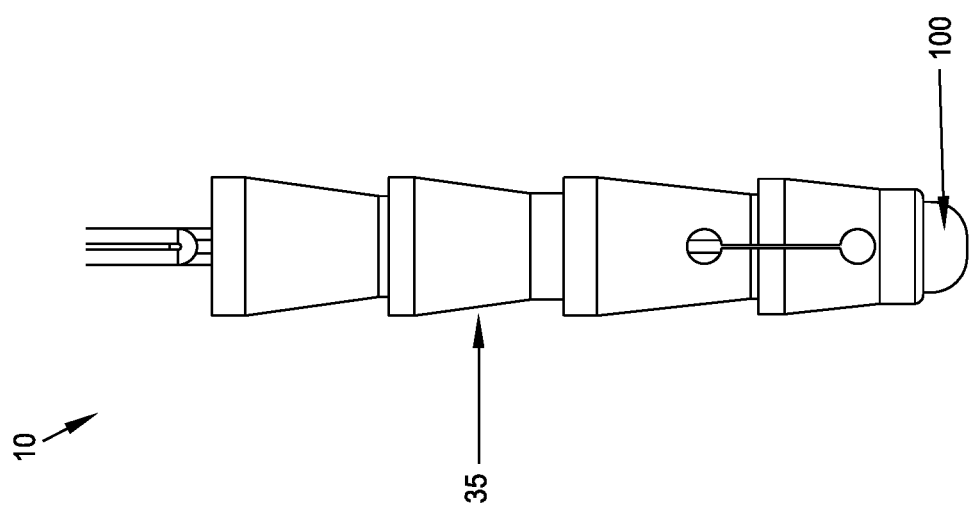
Figure 24:
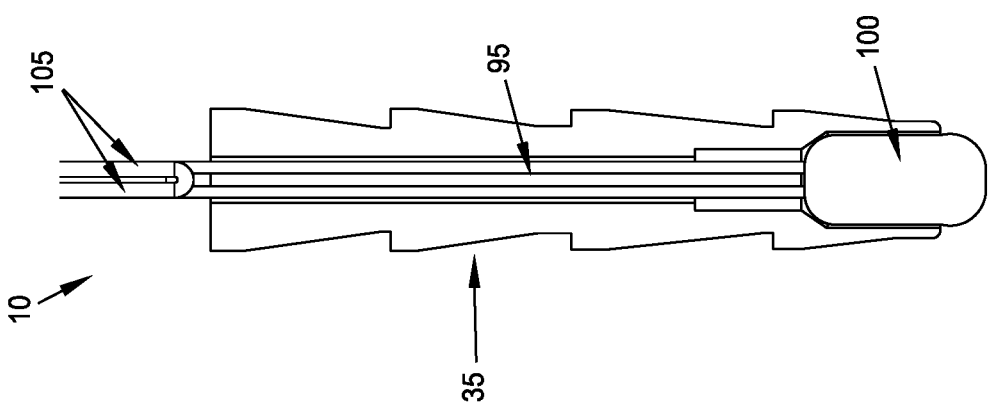

As noted above, enlargement 100 may comprise a solid member attached to the distal end of distal loop 95, or it may comprise a suture knot formed by knotting off the distal ends of distal loop 95 of suture 15. In this latter construction, enlargement 100 can be formed out of a single knot or multiple knots. It can be an overhand knot or other knot such as a "FIG. 8" knot. Suture 15 can also be heat formed so as to create the enlargement 100. This will create a more rigid feature that better enables movement of enlargement 100 from its distal position to its more proximal position. Such heat forming could also be done on a knot or to seal the suture ends distal to the knot.

Force Delivery Mechanisms which are Force-Limiting so as to Provide for the Controlled Delivery of an Actuation Force to the Anchor In the preceding sections, there was disclosed a novel suture anchor system 5 which may be used for, among other things, arthroscopically re-attaching a detached labrum to the acetabulum. As discussed above, novel suture anchor system 5 generally comprises an anchor 10, a suture 15 secured to anchor 10, and an inserter 20 for delivering anchor 10 into the acetabulum. As also discussed above, novel suture anchor system 5 is constructed so that after inserter 20 has delivered anchor 10 into the acetabulum, tensioning of suture 15 causes the body of anchor 10 to expand laterally so that the anchor is secured to the bone, whereby to secure suture 15 to the bone.

In one preferred form of the present invention, suture 15 may comprise a pair of sutures, e.g., a thinner distal suture 95 extending through anchor 10 and a thicker proximal suture 105 extending from thinner distal suture 95 to the proximal end of inserter 20 (e.g., to the handle of inserter 20), such that thicker proximal suture 105 can be used to actuate the anchor by pulling proximally on thinner distal suture 95 and to secure an object (e.g., the labrum) to the bone in which anchor 10 is deployed, e.g., the acetabulum.

And in one preferred form of the present invention, novel suture anchor system 5 is intended to be constructed on a very small scale, e.g., so that anchor 10 has a diameter on the order of 1.5 mm, thinner distal suture 95 is a "Size 2-0 suture" with a diameter of approximately 0.3 mm, and thicker proximal suture 105 is a "Size 1 suture" with a diameter of approximately 0.4 mm.

In view of this unusually small construction, it can be extremely important to limit the magnitude of the tension applied to the suture, since applying too much tension to the suture can result in unintentional damage to the body of anchor 10 and/or in breakage of the suture (particularly the thinner distal suture 95). At the same time, however, it is also important that an adequate amount of force be applied to the anchor in order to ensure proper actuation of the anchor.

In the following sections of this document, there is disclosed force delivery mechanisms which are force-limiting so as to provide for the controlled delivery of an actuation force to anchor 10.

In accordance with the present invention, there is disclosed apparatus that may be used to deliver an anchor into bone and to actuate that anchor (i.e., by pulling proximally on an element) while the anchor is disposed in the bone, so as to set the anchor in the bone. In one preferred form of the present invention, the anchor is an expandable anchor that requires the application of a force at the anchor (preferably by tensioning a suture) in order to expand and/or deform the anchor (either a section of the anchor or the entire body of the anchor). In accordance with the present invention, the apparatus for actuating the anchor (e.g., for tensioning the suture) comprises a force delivery mechanism which is force-limiting in the sense that the mechanism allows the user to manually apply force to the anchor (e.g., by tensioning a suture) up to a specific, desired force limit, whereupon the mechanism automatically disengages and the force thereafter applied to the anchor (e.g., by tensioning the suture) drops to zero (or substantially zero). The disengagement and force-limiting aspect of the force delivery mechanism is automatic and does not require any additional action by the user. In other words, the force delivery mechanism is configured so that when the magnitude of the tension applied to the anchor (e.g., to the suture connected to the anchor) exceeds a certain, pre-determined limit, the force delivery mechanism automatically disengages and no further tension is applied to the anchor.

The alternative to such a force-limiting mechanism is a mechanism that either (i) applies a variable force over a fixed distance of travel, or (ii) a mechanism that requires the user to actively control the delivery of the activation force to the anchor. Neither approach is preferable to a force-limiting mechanism of the sort provided by the present invention. Significantly, a force-limiting mechanism is independent of device variables such as suture stretch, anchor material properties and required actuation travel, and anatomical variables such as bone type and bone quality. For example, in equivalent bone quality, a device that has greater suture stretch may only see partial actuation at the anchor; however, a force-limiting mechanism is independent of suture stretch and hence will actuate the anchor to a consistent, specific force. By way of example but not limitation, the amount of stretch in a suture may significantly exceed the actuation travel required by an anchor, e.g., the suture might stretch 10 mm-15 mm along the length of an inserter when the suture is tensioned, whereas the anchor may only require an actuation travel of 1 mm. In this situation, suture stretch can make it virtually impossible to reliably apply the desired actuation force to the anchor. Furthermore, dense bone will resist the lateral expansion of an anchor more than soft bone will resist the lateral expansion of the anchor. So where the bone is dense, the force applied to the actuation suture may be taken up (i.e., absorbed) by the suture and hence incomplete anchor expansion may occur. Additionally, a device which requires the user to actively control the delivery of the actuation force to the anchor introduces the possibility of user error and unnecessary complications to the device function.

On account of the foregoing, the present invention provides a force delivery mechanism which is force-limiting so as to provide for the controlled delivery of an actuation force to an anchor.

For purposes of clarity of description, the novel force-limiting mechanism will hereinafter generally be discussed in the context of applying an actuation force to an anchor 10 by pulling proximally on its thicker proximal suture 105, whereby to cause its thinner distal suture 95 to move a suture knot (e.g., enlargement 100) or a PEEK cylinder (e.g., deployment cylinder 150) proximally, whereby to expand anchor 10 and set it in bone.

Wishbone Mechanism

Looking now at FIGS. 61-68, there is shown a wishbone force delivery mechanism 300 which is force-limiting so as to provide for the controlled delivery of an actuation force to an anchor, e.g., to the thicker proximal suture 105 of anchor 10. Wishbone mechanism 300 is intended to be incorporated into the handle 125 of the inserter 20 discussed above, which may cause handle 125 to take on a modified configuration from that previously shown. In one preferred form of the invention, wishbone mechanism 300 generally comprises a handle 305, a cap 310, a cleat 315, a wishbone 320 and a finger pull 325. Wishbone apparatus 300 also comprises a proximal spring 330, a distal spring 335 and a wishbone spring 340.

Wishbone 320, finger pull 325 and wishbone spring 340 are the critical components that enable the force-limiting aspect of wishbone mechanism 300, and handle 305 and cap 310 act to contain and guide the actuation. Additionally, proximal spring 330 dampens the hard stop at the end of actuation (i.e., when wishbone 320 pops out of finger pull 325, as will hereinafter be discussed) and distal spring 335 maintains tension on the suture (e.g., thicker proximal suture 105) while the apparatus is in its packaging and/or prior to the delivery of an actuation force to finger pull 325, as will hereinafter be discussed.

Wishbone mechanism 300 is integrated into inserter 20 by mounting cap 310 to the proximal end of hollow push tube 110 of inserter 20, with thicker proximal suture 105 of anchor 10 extending up hollow push tube 110 for releasable connection to cleat 315, with handle 305 configured to be grasped by the hand of a user, and with finger pull 325 configured to be grasped by the index finger and middle finger of the user.

Delivery of the suture anchor (e.g., anchor 10) requires a hole in the bone, created by either a drill bit or a punch; the anchor is then inserted into the hole to a specific depth indicated by markings (not shown) provided on the hollow push tube 110. Once the anchor is located at the proper depth, the anchor requires an actuation step in which a suture knot (e.g., enlargement 100) and/or a PEEK cylinder (e.g., deployment cylinder 150) at the distal end of the suture (e.g., the thinner distal suture 95) are pulled proximally through the anchor, causing the anchor to expand in the manner previously described. The proximal advancement of the suture knot (e.g., enlargement 100) and/or the PEEK cylinder (e.g., deployment cylinder 150) within anchor 10, and thereby expansion of the anchor, is controlled by the force-limiting wishbone mechanism 300 which is disposed at, and constitutes, the proximal (i.e., handle) end of the inserter 20, with cap 310 being connected to the hollow push tube 110 of the inserter 20. The force-limiting wishbone mechanism 300 is single-handedly actuated by the user via finger pull 325 which is disposed at the proximal (handle) end of the inserter 20.

To ensure optimal expansion of the anchor and maximum resistance to pullout, the expansion of the anchor is effected by the application of a pre-determined actuation force. The force-limiting wishbone mechanism 300 allows the user to actuate and expand the anchor up to the pre-determined maximum level of force and, upon reaching that pre-determined maximum level of force, the wishbone mechanism automatically disengages and thereby prevents the user from applying any further force to the anchor, but it does not disengage the force delivery mechanism until after that pre-determined maximum level of force has been applied to the anchor. Thus, wishbone mechanism 300 ensures that the correct level of tension is applied to anchor 10 every time (provided, of course, that an adequate level of force is supplied to finger pull 325 during actuation).

Overview of Wishbone Mechanism 300

As discussed above, after anchor 10 has been positioned in a bone hole, it is set by expanding the anchor body, which is effected by pulling the thinner distal suture 95 (and hence suture knot 100 and/or PEEK cylinder 150) proximally. As also discussed above, the thinner distal suture 95 is pulled proximally by pulling the thicker proximal suture 105 (which extends to the handle) proximally. With wishbone mechanism 300, the proximal end of the thicker proximal suture 105 is secured to cleat 315, which is itself releasably connected to finger pull 325 via wishbone 320, as will hereinafter be discussed. From the user's point of view, anchor actuation is effected by pulling finger pull 325 proximally until wishbone apparatus 300 has automatically disengaged (FIG. 68), whereupon any further proximal movement of finger pull 325 is dampened by proximal spring 330. During anchor actuation and prior to finger pull 325 engaging proximal hard stop 345, the wishbone apparatus 300 will make an audible "snap" and, simultaneously, the resistance at finger pull 325 will drop significantly—this signifies that the pre-determined maximum level of force has been reached and that the wishbone apparatus 300 has automatically disengaged (i.e., by virtue of wishbone 320 popping free of finger pull 325, as will hereinafter be discussed). At this point, the anchor has been expanded in the bone, and the proximal end of the thicker proximal suture 105 can be then unwrapped from cleat 315 and the inserter 20 (which includes wishbone mechanism 300) can be removed from the patient, leaving anchor 10 secured to the bone, and suture 105 extending out of the bone.

The Step-By-Step Function of Wishbone Apparatus 300

Figure 62:
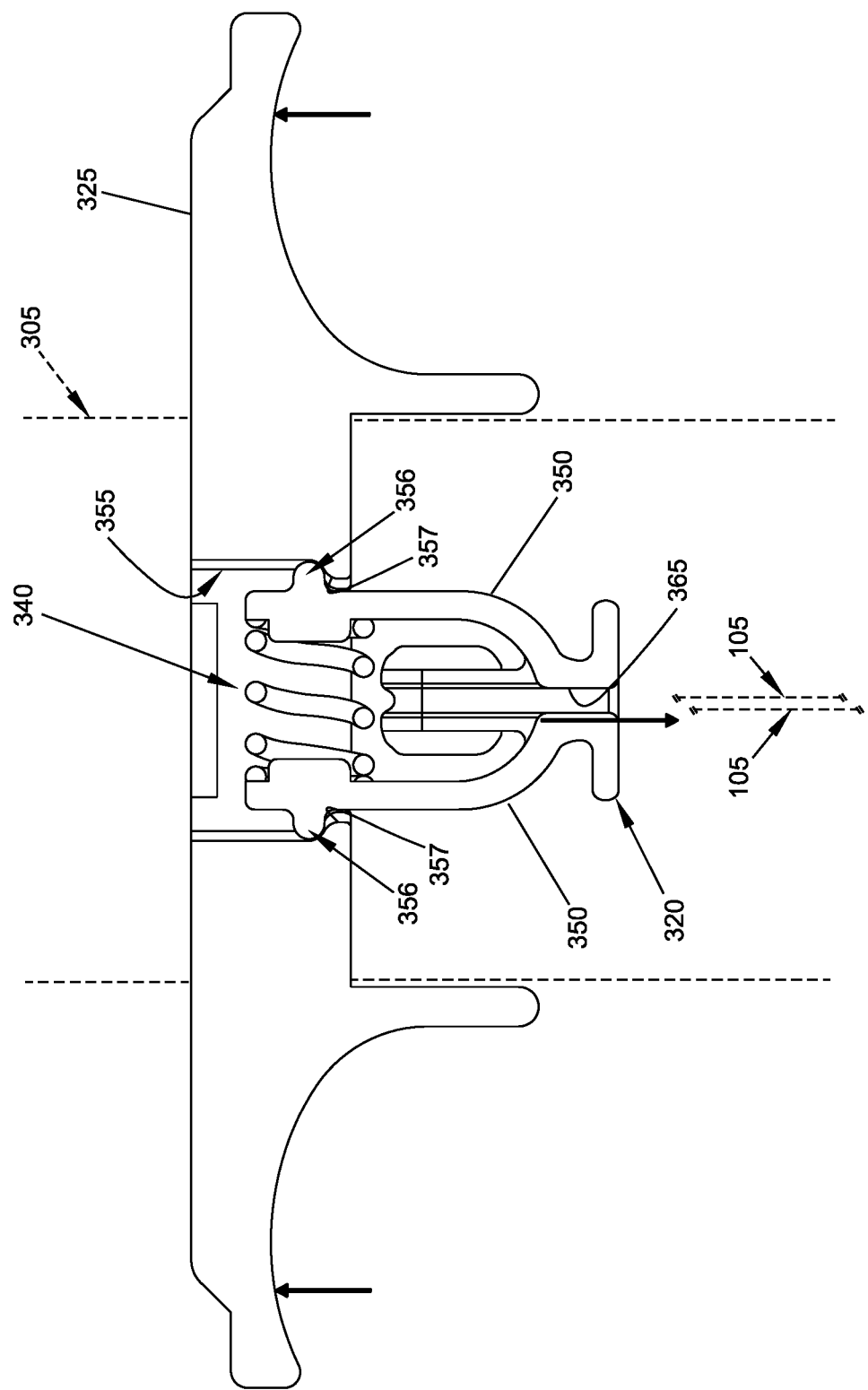
Figure 63:
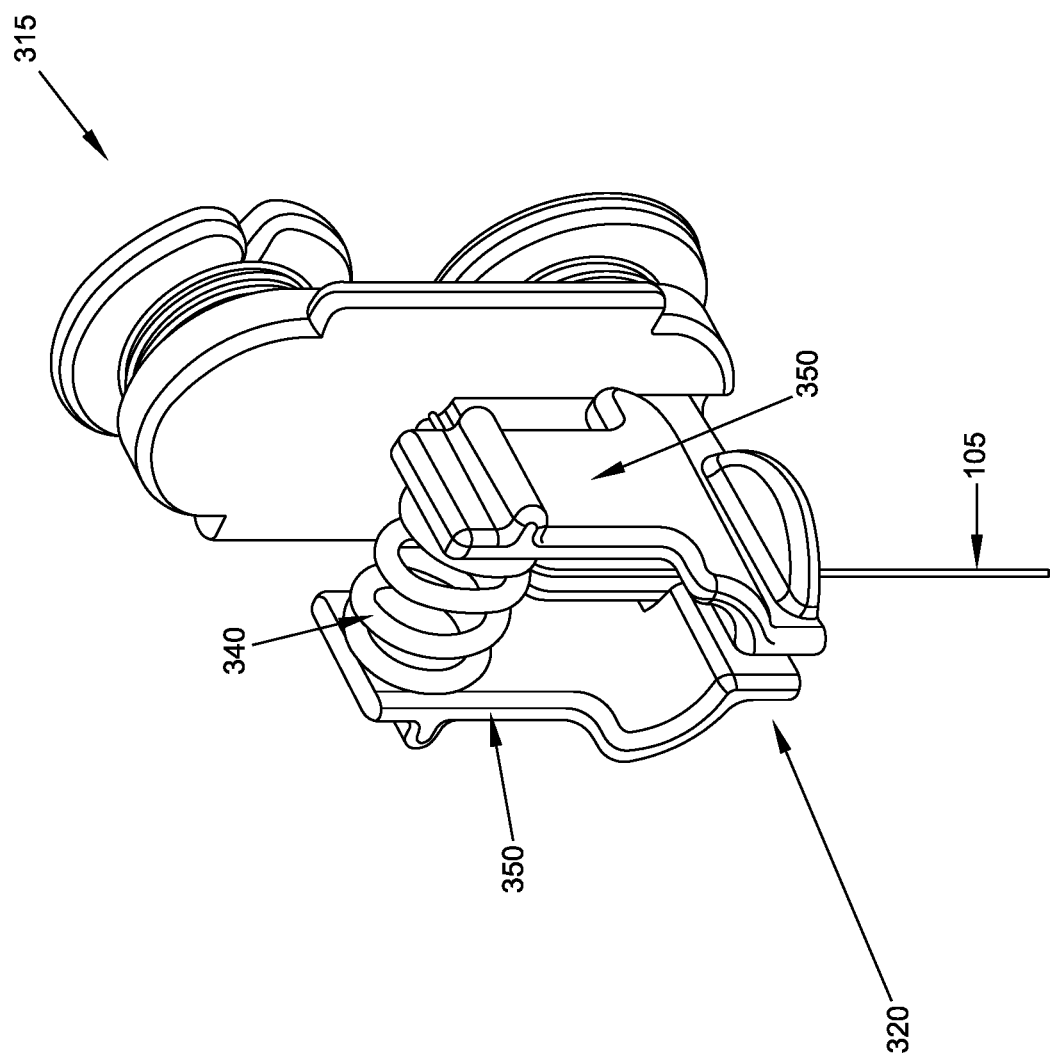
Figure 64:
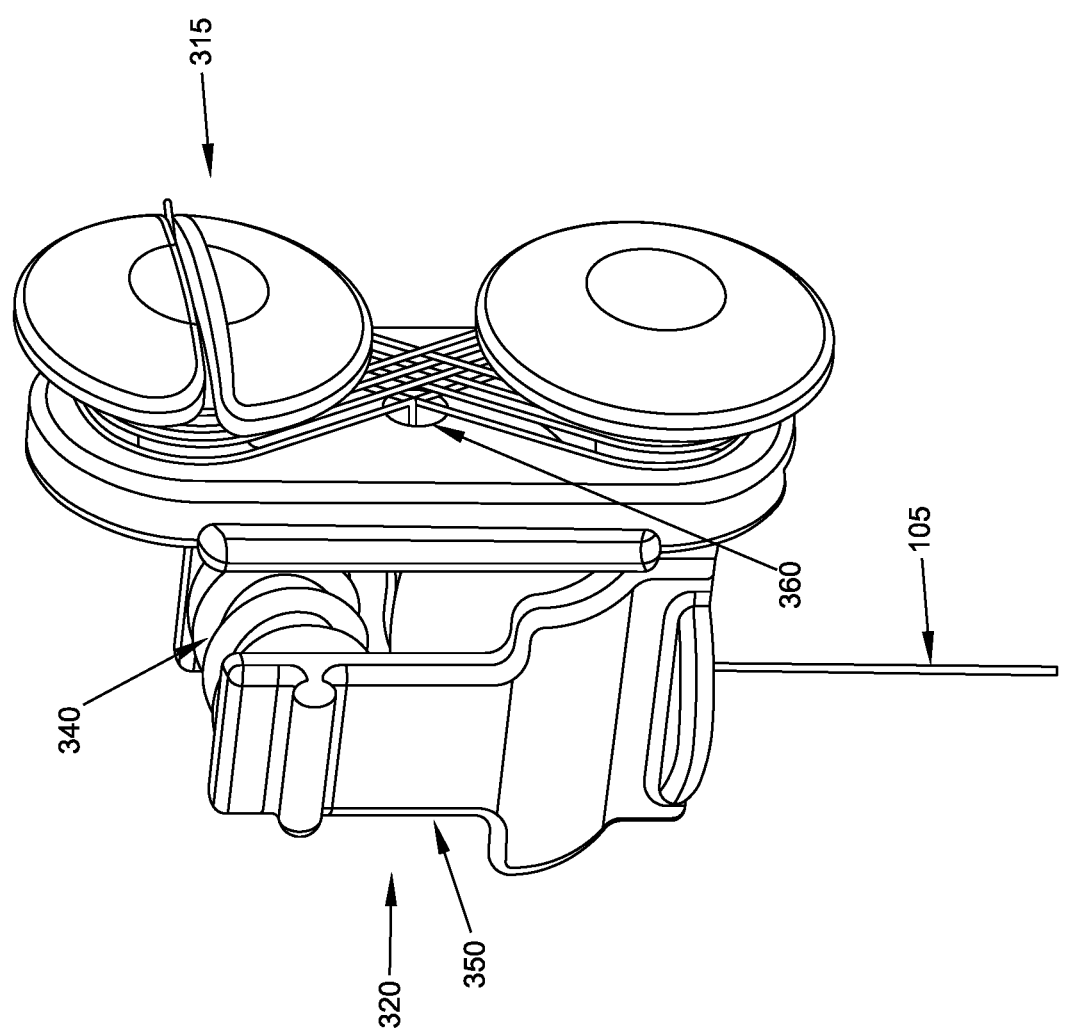
Figure 65:
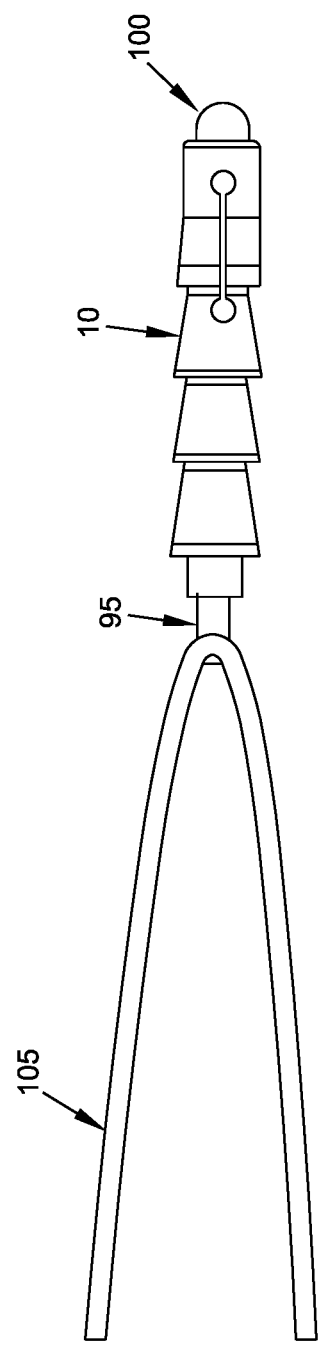
Figure 66:
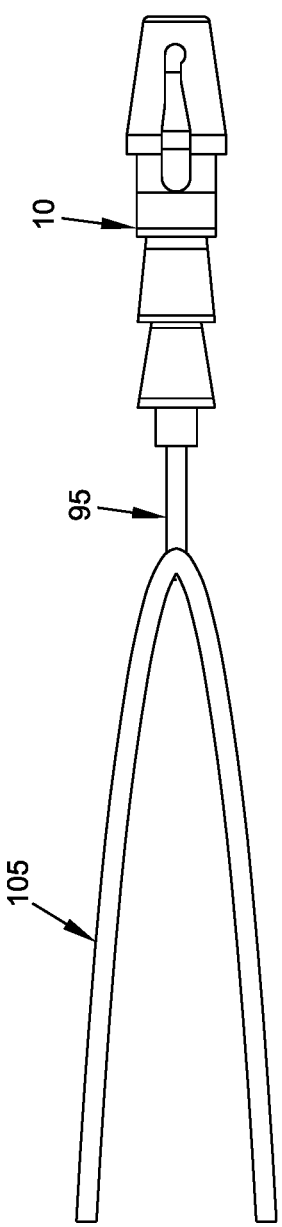
Figure 67:
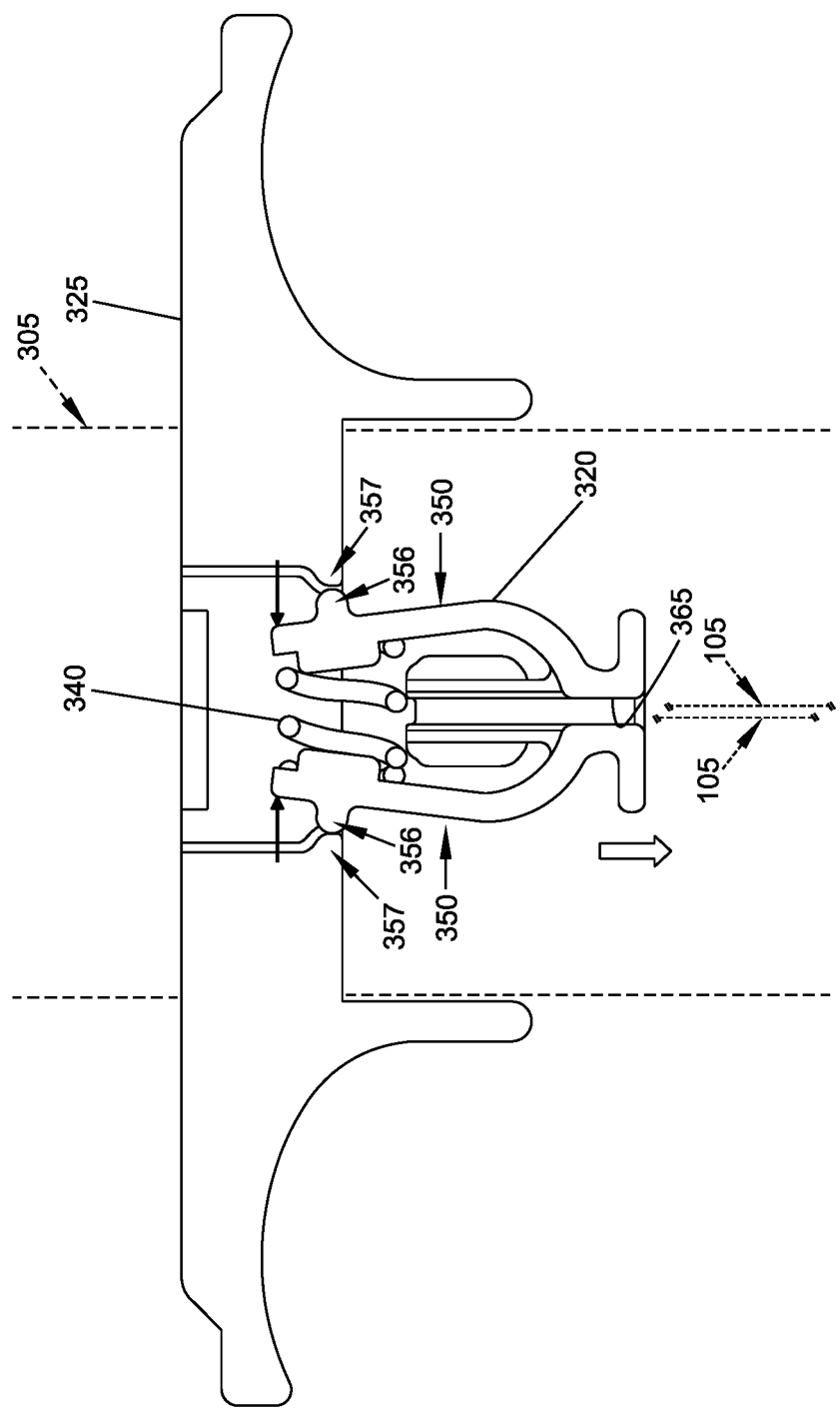
Figure 68:
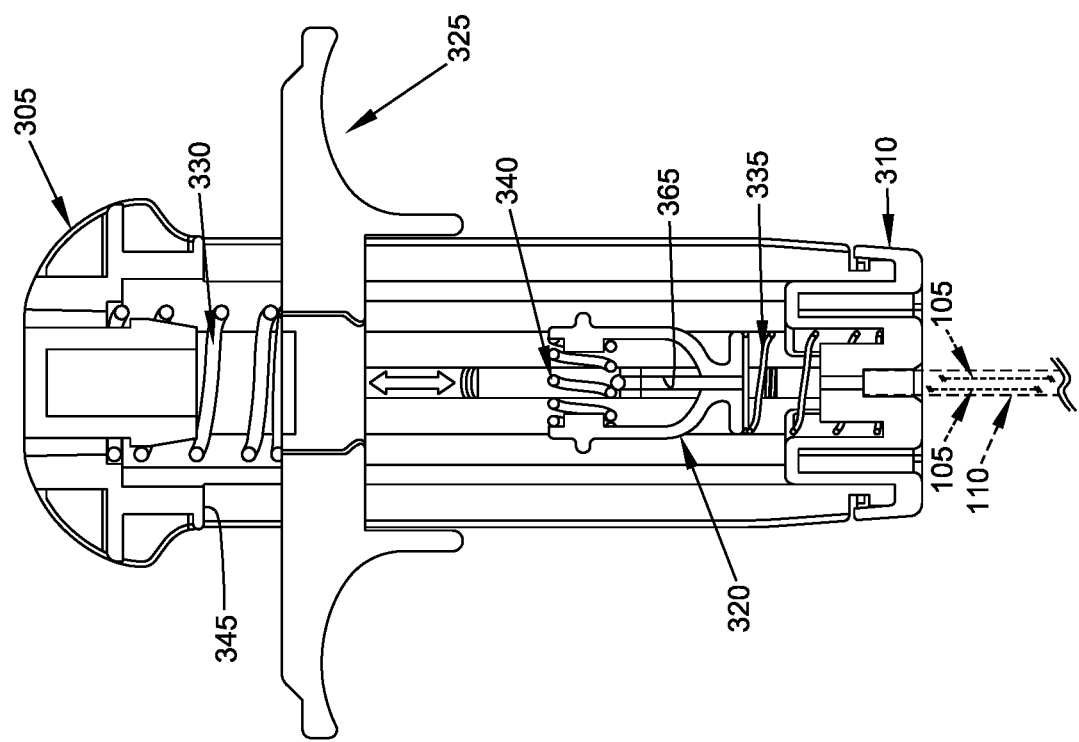

1. The user pulls on finger pull 325 with two fingers. This causes the user-applied force to be transmitted from finger pull 325 to wishbone 320, with the two arms 350 (FIG. 62) of wishbone 320 being pulled in tension. The two arms 350 of wishbone 320 are initially held together via a spring-assisted snap fit in bore 355 (FIG. 62) of finger pull 325. This snap fit is preferably formed by engagement of wishbone projections 356 (FIG. 62) and finger pull narrowings 357 (FIG. 62).

2. Force is then transmitted from wishbone 320 to the thicker proximal suture 105 (i.e., the suture 105 which extends through the hollow push tube 110 of inserter 20 and which is attached to the thinner distal suture 95 extending through anchor 10). More particularly, the proximal end of the thicker proximal suture 105 is wrapped around cleat 315, and cleat 315 is attached to wishbone 320, so that pulling proximally on wishbone 320 pulls proximally on the thicker proximal suture 105. The thicker proximal suture 105 that is wrapped around cleat 315 exits through a hole 360 (FIGS. 63 and 64) formed in the middle of cleat 315 and extends down the center axis of wishbone 320, e.g., via opening (e.g., a groove or hole) 365 (FIG. 62), through cap 310 and then down hollow push tube 110 of inserter 20.

3. The thicker proximal suture 105 that is wrapped around cleat 315 and extends down to and through the thinner distal suture 95 transmits force from finger pull 325 to the thinner distal suture 95, which causes the knotted distal end 100 of the thinner distal suture 95 and/or the PEEK cylinder 150 to move proximally and hence causes anchor expansion. See FIGS. 65 (which shows the anchor 10 in its undeployed configuration) and 66 (which shows the anchor 10 in its deployed configuration).

4. The initial force applied by the user at finger pull 325 is low and primarily accounts for the stretch in the suture; this low force creates very little compression of wishbone 320.

5. After the suture has stretched, the extension force between finger pull 325 and wishbone 320 increases, and arm 350 of wishbone 320 begins to compress inwardly, against the force of wishbone spring 340, as the wishbone projections 356 ride on the finger pull narrowings 357 (FIG. 62) in finger pull 325. See FIG. 67.

6. At a pre-determined maximum level of force (e.g., 10±2 lbf), arms 350 of wishbone 320 compress enough to allow finger pull 325 and wishbone 320 to separate. The force at which wishbone 320 disengages finger pull 325 is dictated by material selection and the geometry of the wishbone 320 and finger pull 325, including the characteristics specific to the wishbone projections 356 and finger pull narrowings 357. Among other things, the force at which disengagement occurs is determined by the amount of overlap (i.e. compression distance) between wishbone projections 356 and finger pull narrowings 357, the angles of the contact surfaces, the surface finishes of the contact surfaces, the power of spring 340, etc. See FIGS. 67 and 68.

7. Once wishbone 320 and finger pull 325 have separated, the user is unable to apply any further force to the suture, and hence is unable to apply any further force to the anchor.

Wishbone Mechanism Variations

In addition to the foregoing, the force-limiting feature of the wishbone mechanism can be provided via the following design alternatives.

Figure 69:
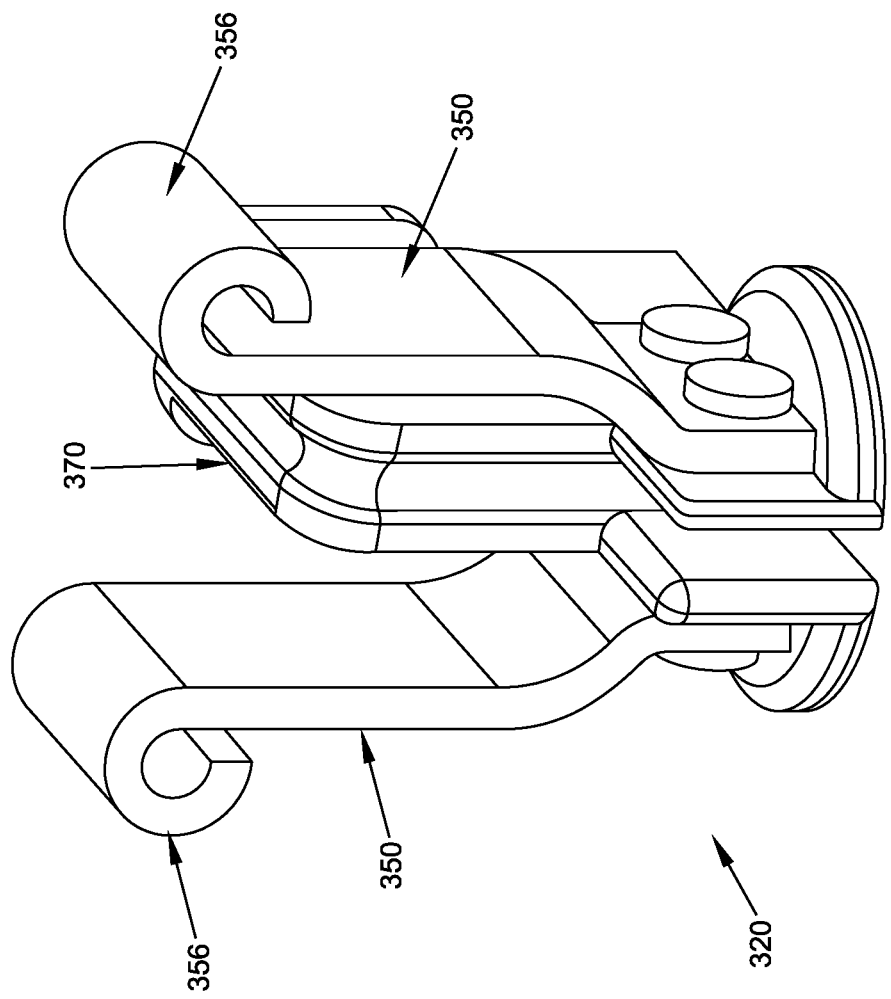
FIGS. 69 and 70 are schematic views showing alternative constructions for the wishbone element of the wishbone force delivery mechanism of FIGS. 61-68.
Figure 70:
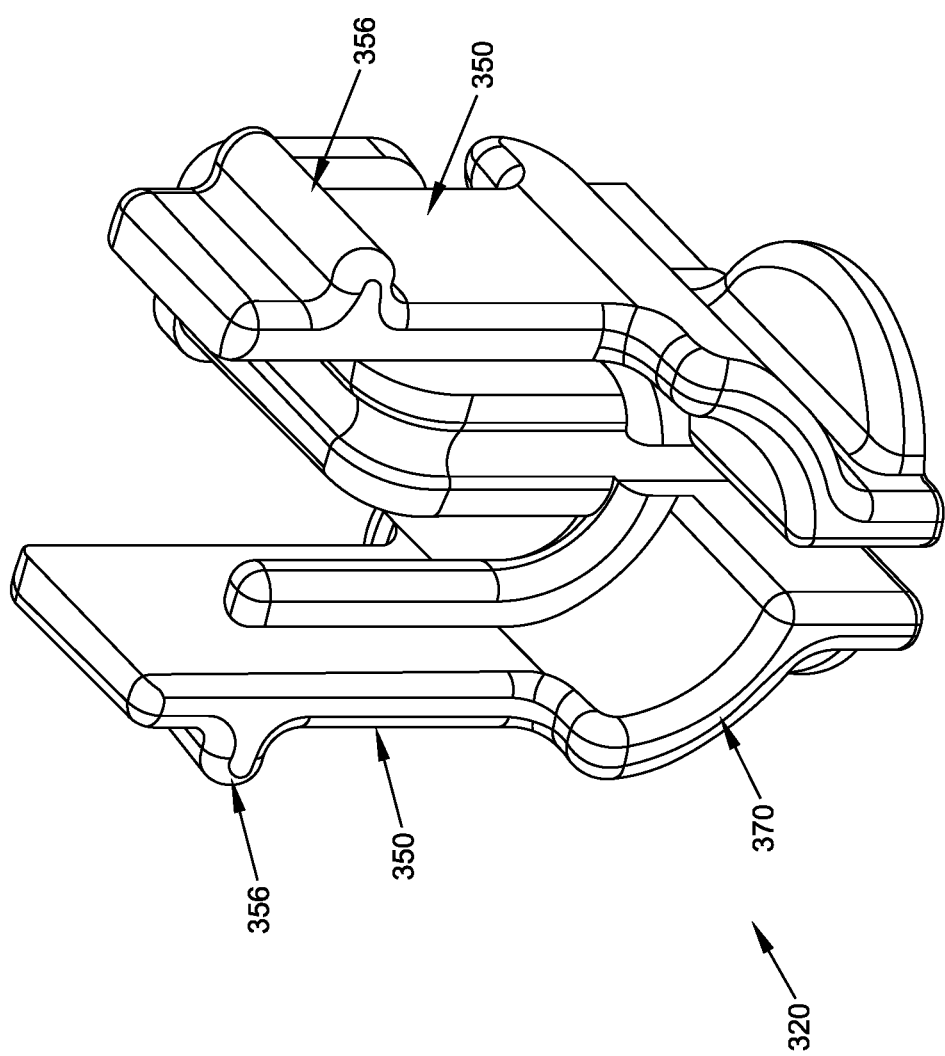

(i) No Wishbone Spring. The compression spring 340 between arms 350 of wishbone 320 can be omitted, and the function of wishbone compression spring 340 can be provided by using the spring characteristics of the material used to form the wishbone, or by using the geometry of the wishbone, or both. More particularly, wishbone 320 can be manufactured from a resilient metal such as spring steel or from a resilient polymer, whereby to provide the required spring characteristics to arms 350 of wishbone 320. Alternatively, wishbone 320 can be manufactured as a steel/polymer hybrid, where arms 350 are formed out of spring steel and body 370 is formed out of polymer (FIG. 69). As will be appreciated by those skilled in the art, the thickness and shape of wishbone 320 can be designed so as to achieve a moment of inertia that has the same effect as the compression spring (FIGS. 69 and 70).

Figure 71:
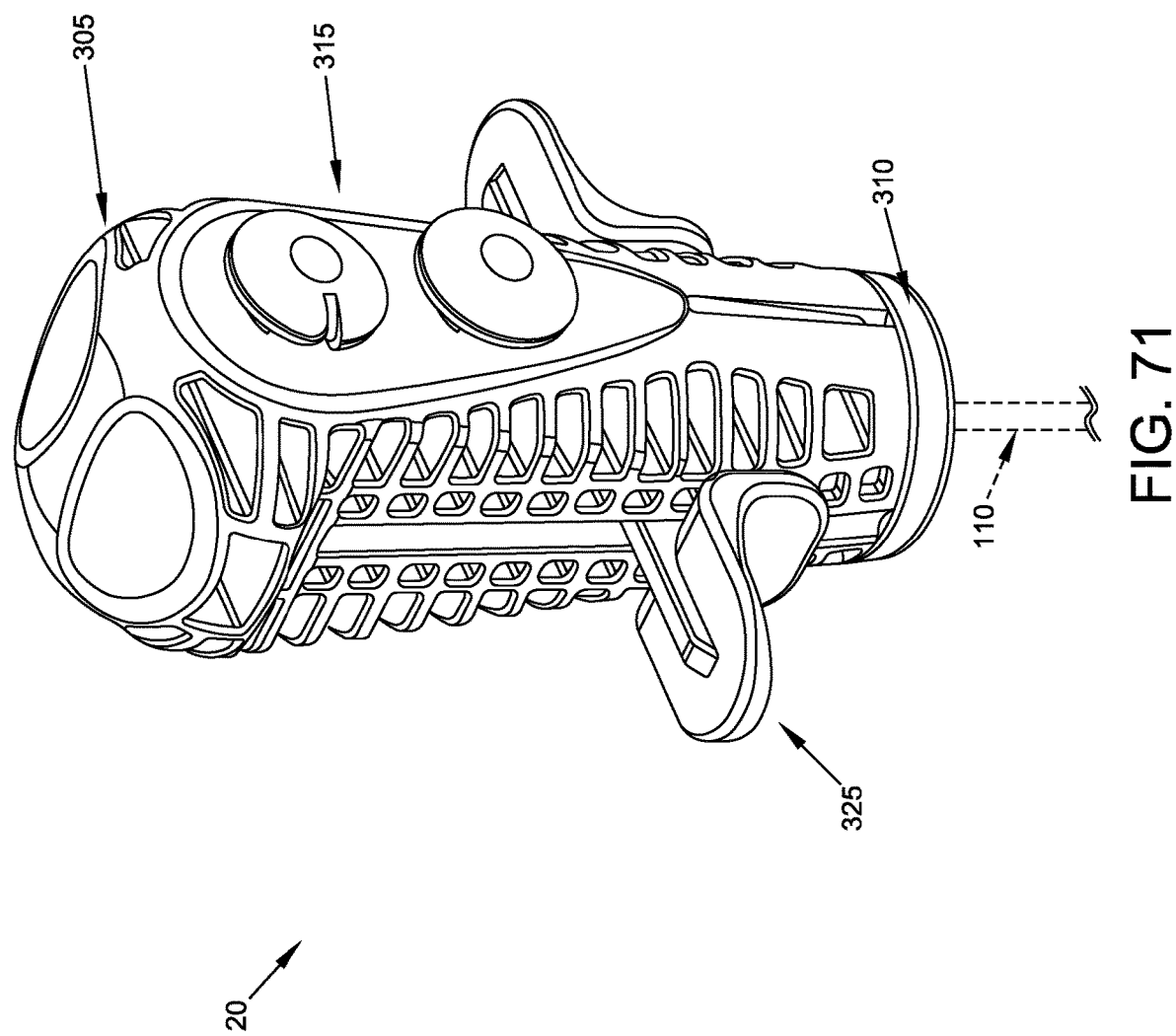
FIGS. 71-74 are schematic views showing design alternatives for the wishbone force delivery mechanism of FIGS. 61-68 (note that in FIG. 72, only one suture strand is shown for clarity of illustration)
Figure 72:
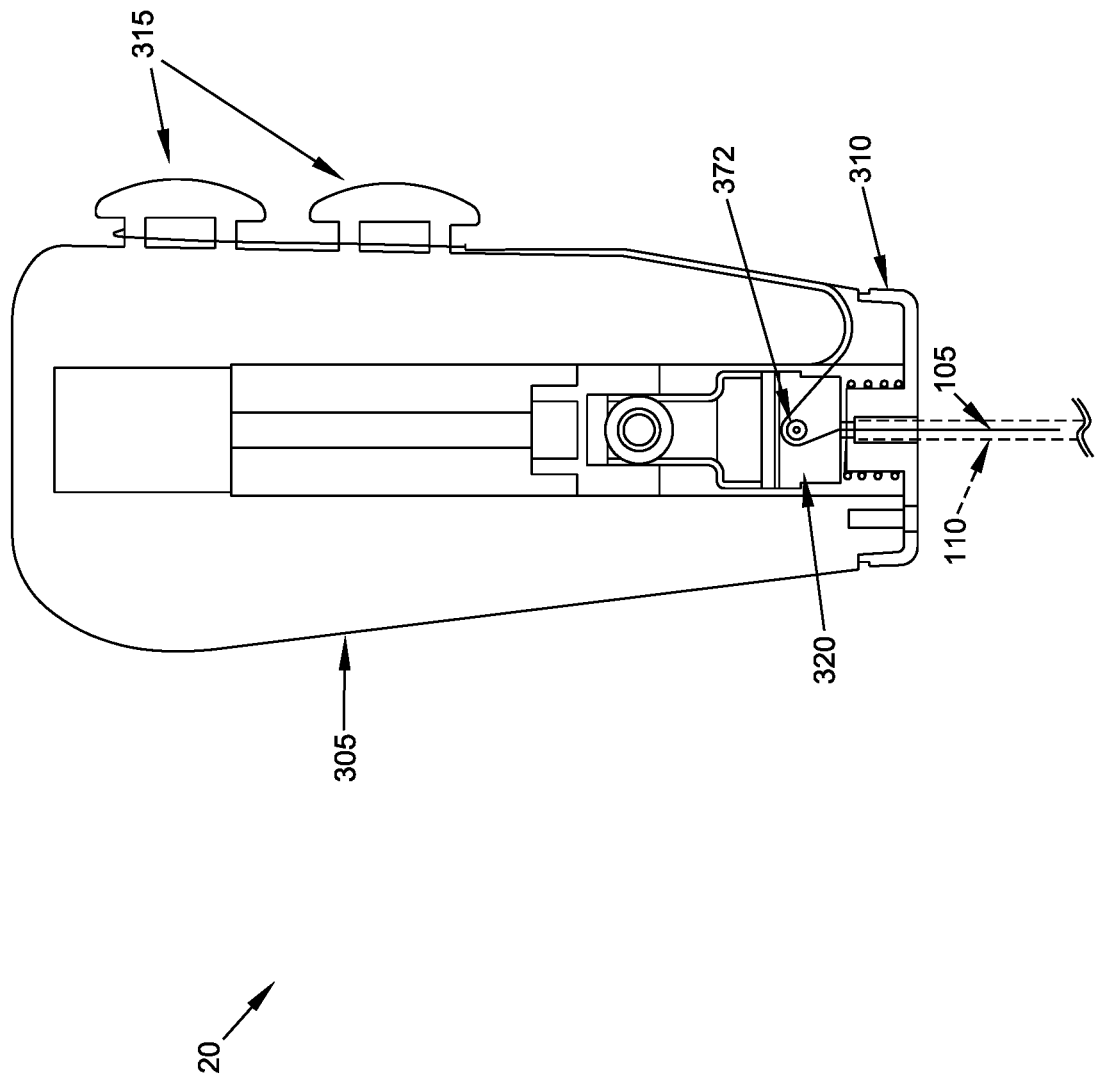

(ii) Stationary Cleat. Cleat 315 can be formed integral with handle 305, i.e., so that cleat 315 is effectively fixed to handle 305 (FIG. 71). In this case, the suture path runs distally from cleat 315, wraps around handle 305 at the junction between handle 305 and cap 310 (e.g., at 371), and wraps around wishbone 320 (e.g., at 372) before going into the interior of hollow push tube 110 of inserter 20 (FIG. 72). With this design, the thicker proximal suture 105 slides relative to the wishbone 320 as the finger pull 325 is moved proximally by the user. And with this design, the actuation force felt by the user at finger pull 325 is approximately twice the force applied at the anchor.

Figure 73:
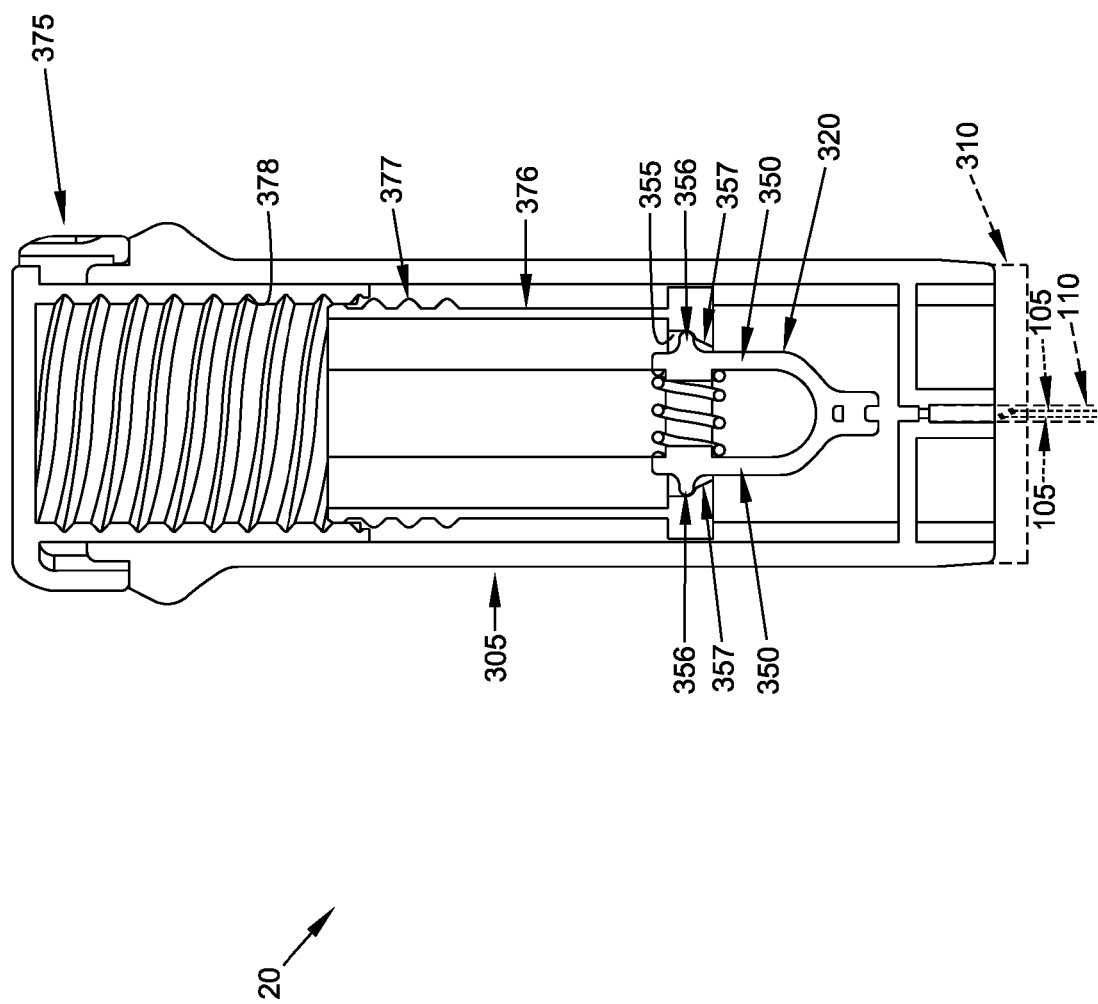
Figure 74:
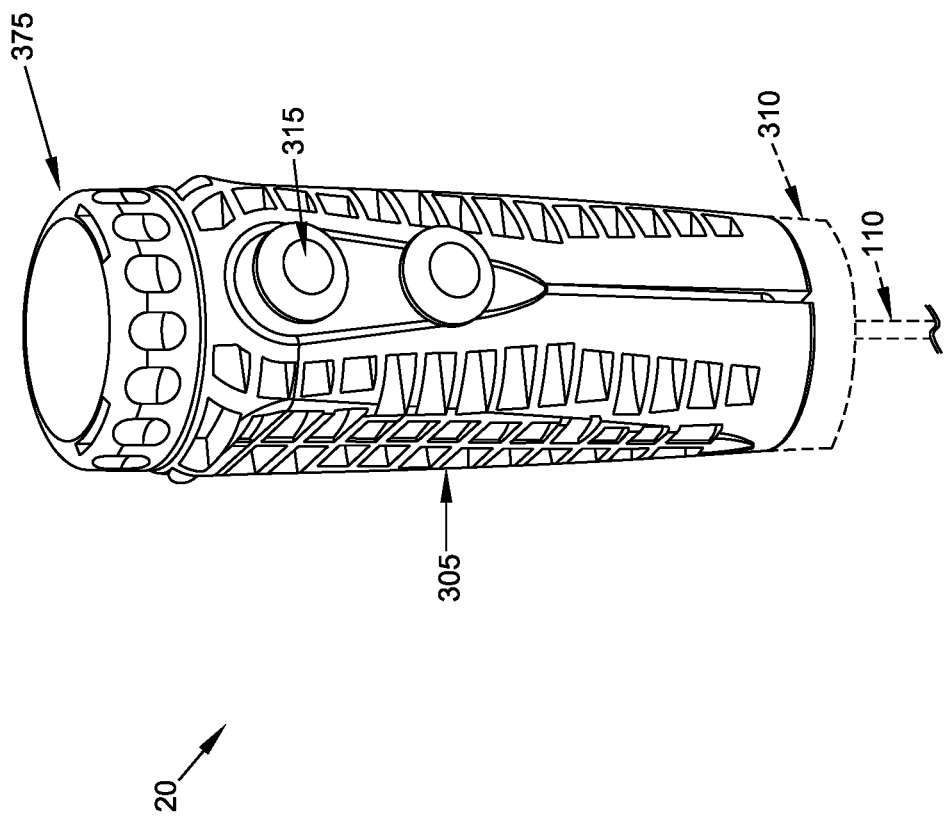
Figure 75:
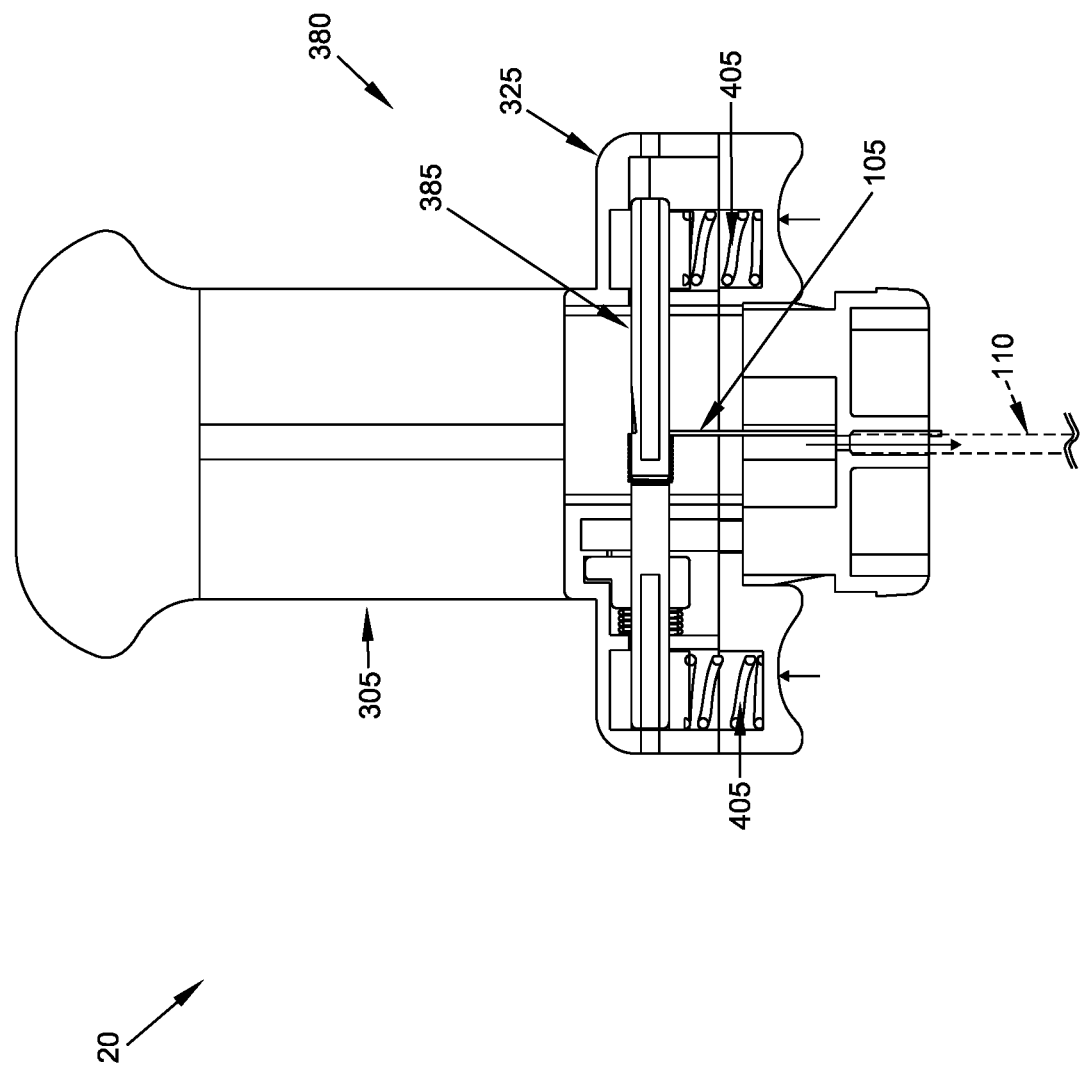
FIGS. 75-79 are schematic views showing another form of the present invention, wherein the force delivery mechanism comprises a spooling force delivery mechanism (note that in FIGS. 75-79, only one suture strand is shown for clarity of illustration)
Figure 76:
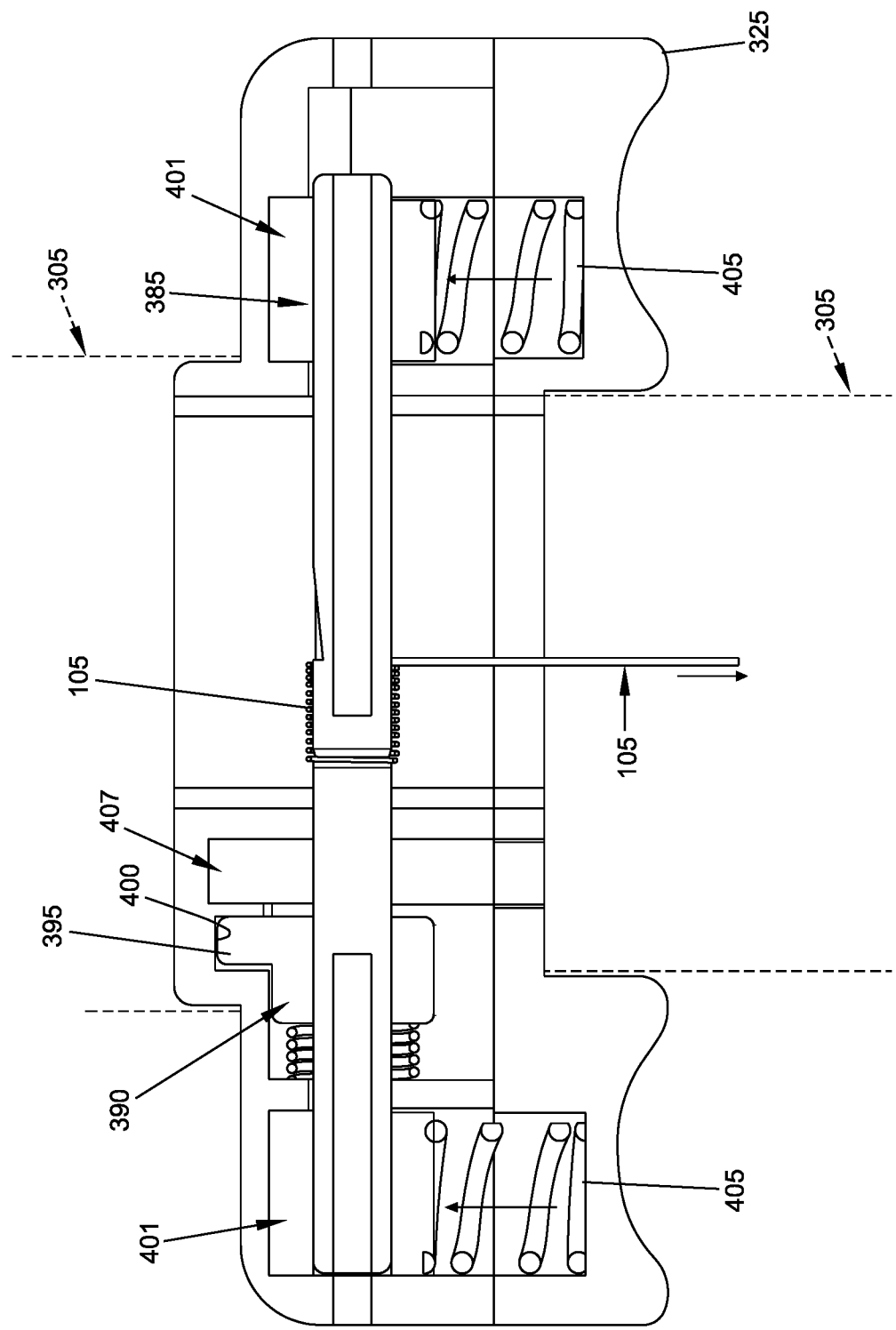
Figure 77:
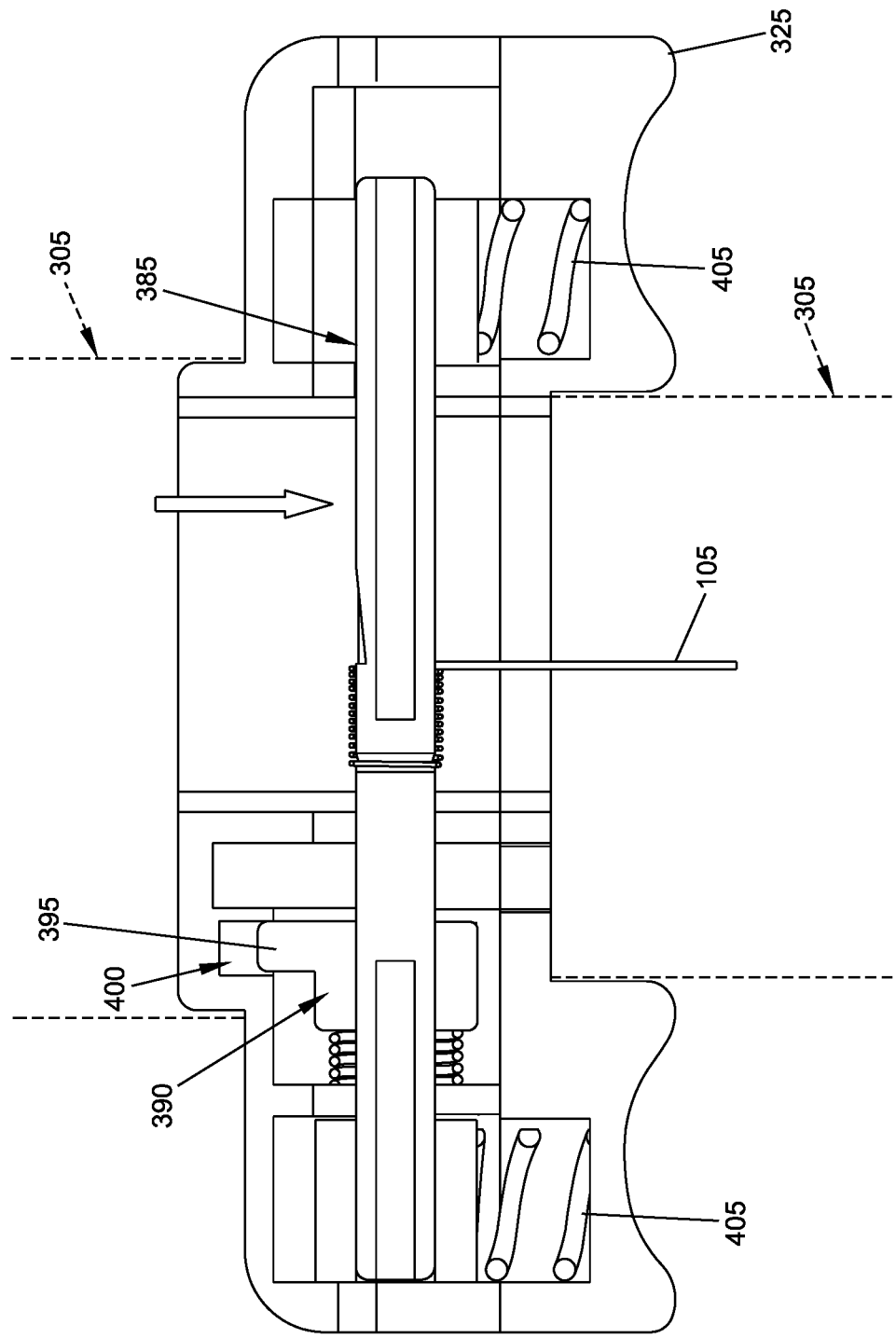
Figure 78:
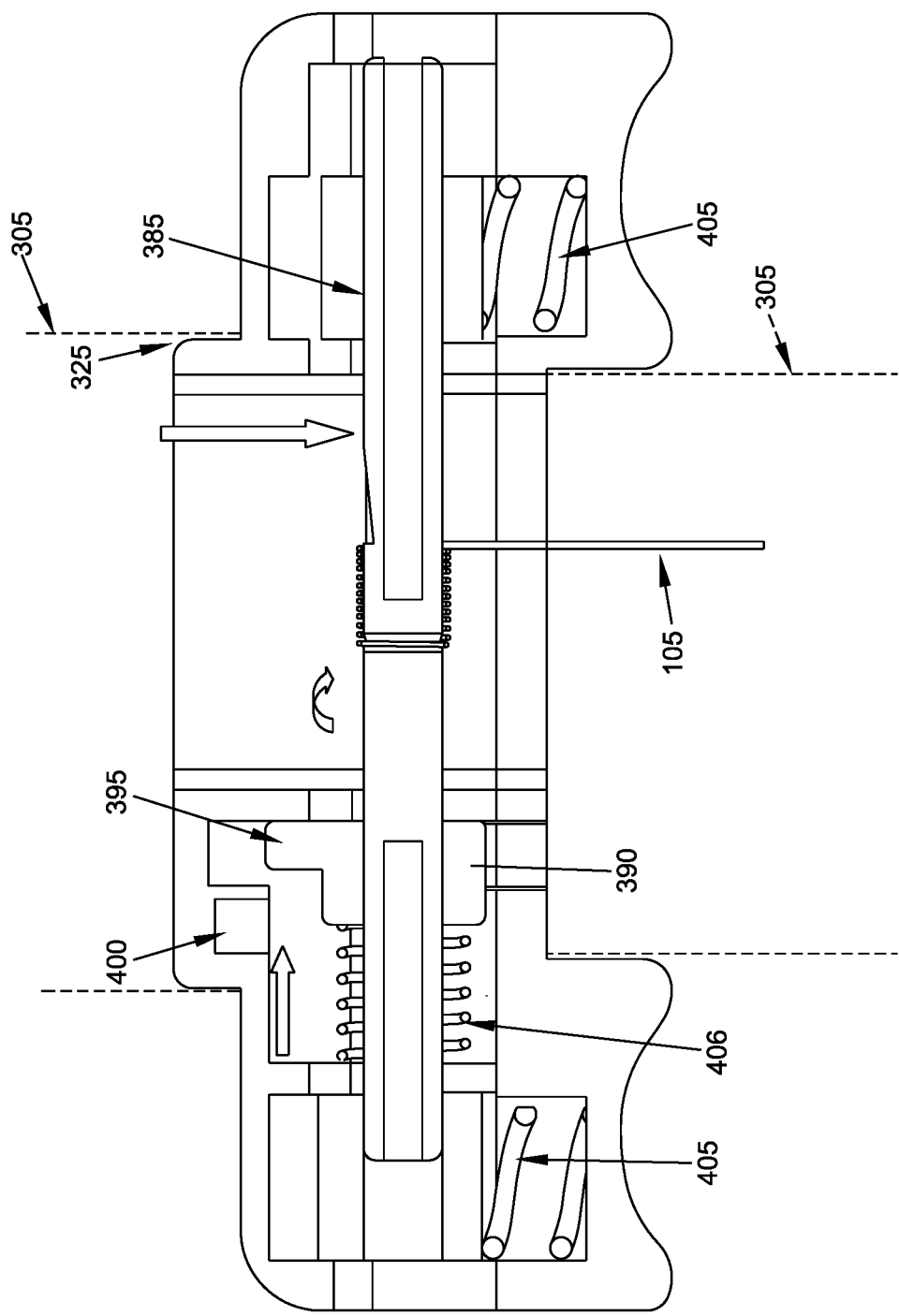
Figure 79:
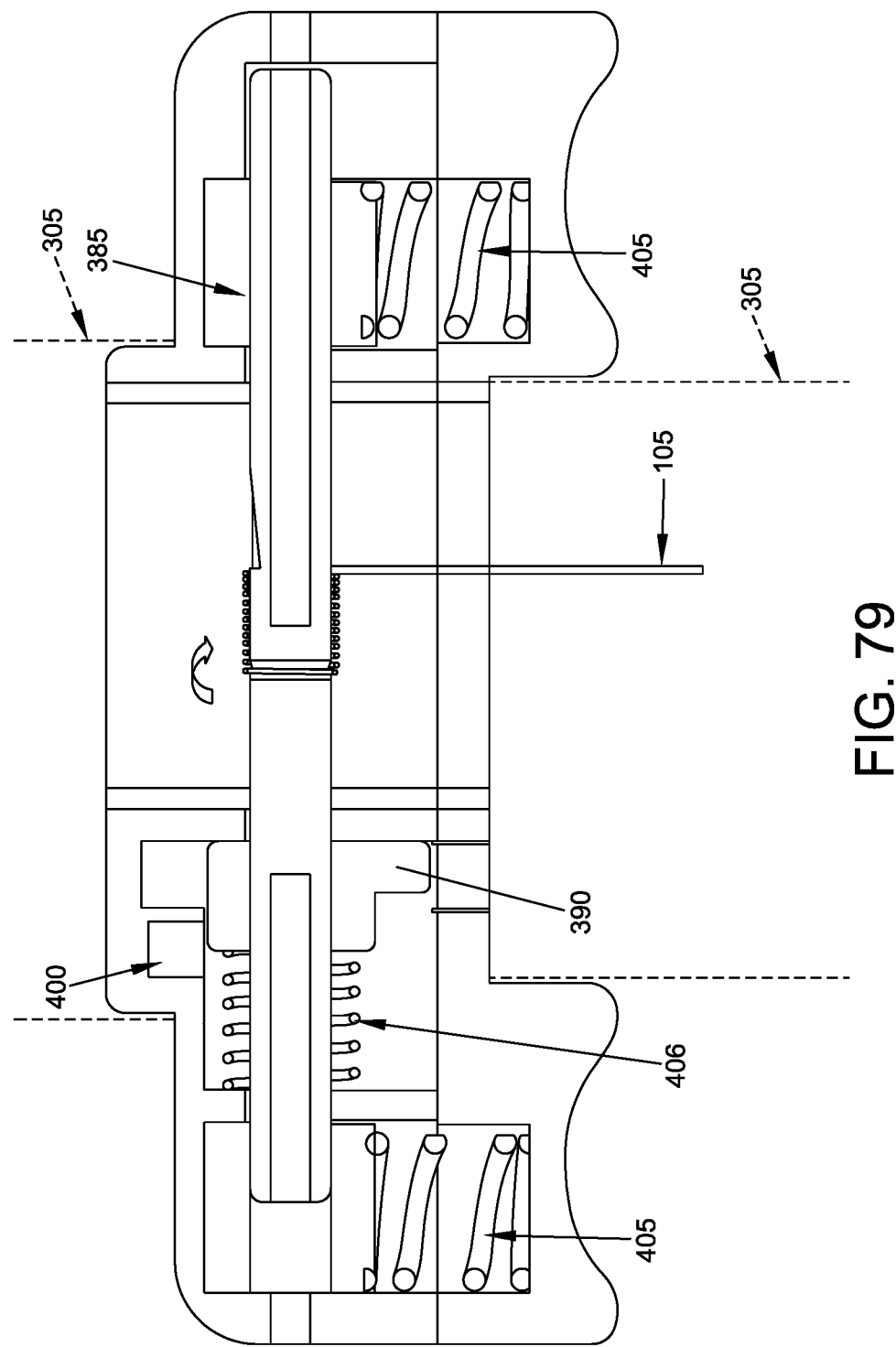

(iii) Rotational Actuation. Instead of the user pulling proximally on finger pull 325 to actuate the anchor, the user can rotate a knob 375 at the proximal end of handle 305 that translates this user-applied rotation into a linear actuation that pulls on wishbone 320 (which is secured to cleat 315) so as to actuate the anchor. See FIG. 73. More particularly, in this form of the invention, rotation of knob 375 causes longitudinal motion of a pull tube 376 within handle 305 by virtue of the engagement of helical thread 377 of pull tube 376 with helical groove 377 of knob 378. The distal end of pull tube 376 has a configuration similar to corresponding portions of finger pull 325, i.e., pull tube 376 includes the bore 355 for receiving the arms 350 of wishbone 320, and narrowings 357 for engagement with projections 356 of wishbone 320. As a result of this construction, when knob 375 is appropriately rotated, pull tube 376 will traverse longitudinally in the proximal direction pulling on wishbone 320, whereby to apply force to the thicker proximal suture 105 attached to cleat 315 (since the cleat 315 is attached to wishbone 320). In an alternative embodiment, and looking now at FIG. 74, cleat 315 is mounted on the handle 305, and the suture is tensioned by passing the suture around a portion of the wishbone (e.g., in a manner analogous to that shown at 372 in FIG. 72) so that proximal movement of the wishbone pulls the suture proximally.

(iv) Furthermore, instead of the user pulling proximally on finger pull 325 to actuate the anchor, or rotating knob 375 to actuate the anchor, other forms of user controls may be provided for actuating the anchor. By way of example but not limitation, the user may actuate the anchor by pulling a lever, squeezing a trigger, pulling a tab, etc. These and other constructions will be apparent to those skilled in the art in view of the present disclosure.

Spooling Mechanism

In another form of the invention, and looking now at FIGS. 75-79, wishbone mechanism 300 may be replaced by a spooling mechanism 380 wherein the force-limiting mechanism is completely contained within finger pull 325. More particularly, in this form of the invention, the thicker proximal suture 105 is wrapped around a shaft 385 which is disposed within finger pull 325 and selectively rotatable. In accordance with this form of the invention, shaft 385 is prevented from rotating until the pre-determined maximum level of force is reached, whereupon shaft 385 is permitted to rotate freely, and thicker proximal suture 105 is unwrapped from the shaft, whereupon to terminate the application of force to thicker proximal suture 105.

The following step-by-step description further describes the structure and function of spooling mechanism 380.

1. The user pulls on finger pull 325 with two fingers—within the finger pull, an equal and opposite force is transmitted to the thicker proximal suture 105 spooled on shaft 385. See FIG. 75.

2. The thicker proximal suture 105 is wrapped around shaft 385 and, as force is applied to thicker proximal suture 105 due to the proximally-directed force applied to finger pull 325, a keyed collar 390, which is fixedly secured to shaft 385 and has a finger 395 that is normally disposed within a slot 400 in finger pull 325, prevents shaft 385 from rotating by virtue of the engagement of finger 395 with the walls of slot 400. See FIG. 76.

3. Additionally, as a retracting force is applied to shaft 385 via finger pull 325, an equal and opposite force is applied from shaft 385 to its two axle mounts 401 which rotatably support shaft 385, and hence to two compression springs 405 which resiliently support the two axle mounts 401 within finger pull 325 (and hence resiliently support shaft 385 within the finger pull 325). Compression springs 405 initially prevent shaft 385 from being pulled distally within finger pull 325 (and hence initially prevent keyed collar 390 from withdrawing its finger 395 from slot 400 in finger pull 325). As a result, the initial application of force to finger pull 325 is transferred to thicker proximal suture 105.

4. As noted above, the initial force applied by the user at finger pull 325 is low, and primarily accounts for the stretch in the suture—this low force creates very little compression of two compression springs 405 supporting shaft 385 in finger pull 325. As a result, finger 395 of keyed collar 390 remains engaged in slot 400 in finger pull 325, shaft 385 remains rotationally locked to finger pull 325, and force applied to finger pull 325 is transferred to thicker proximal suture 105.

5. After the suture has stretched, the force applied to compression springs 405 supporting shaft 385 in finger pull 325 increases, and shaft 385 begins to move distally, against the force of springs 405, relative to finger pull 325. See FIG. 77.

6. At the pre-determined maximum level of force (e.g., 10±2 lbf), springs 405 supporting shaft 385 compress to the point where finger 395 of keyed collar 390 is withdrawn slot 400 in finger pull 325. At this point a spring 406 in finger pull 325 forces shaft 385 and keyed collar 390 laterally, so that finger 395 of keyed collar 390 steps away from slot 400 in finger pull 325 and is aligned with a large cavity 407 formed in the finger pull 325, and so that shaft 385 is now free to rotate within finger pull 325. Shaft 385 will thereupon rotate freely within finger pull 325 and thereby release the tension in the thicker proximal suture 105. See FIG. 78.

7. Upon such shaft rotation, the user is unable to apply any further force to thicker proximal suture 105, and hence the user is unable to apply any further force to anchor 10. See FIG. 79.

8. The user is then able to remove the inserter from the body of the patient without any additional steps needing to be taken with respect to spooling mechanism 380—as the inserter is removed, thicker proximal suture 105 simply unwinds (i.e., unspools) from shaft 385.

Double Wedge Mechanism

Figure 80:
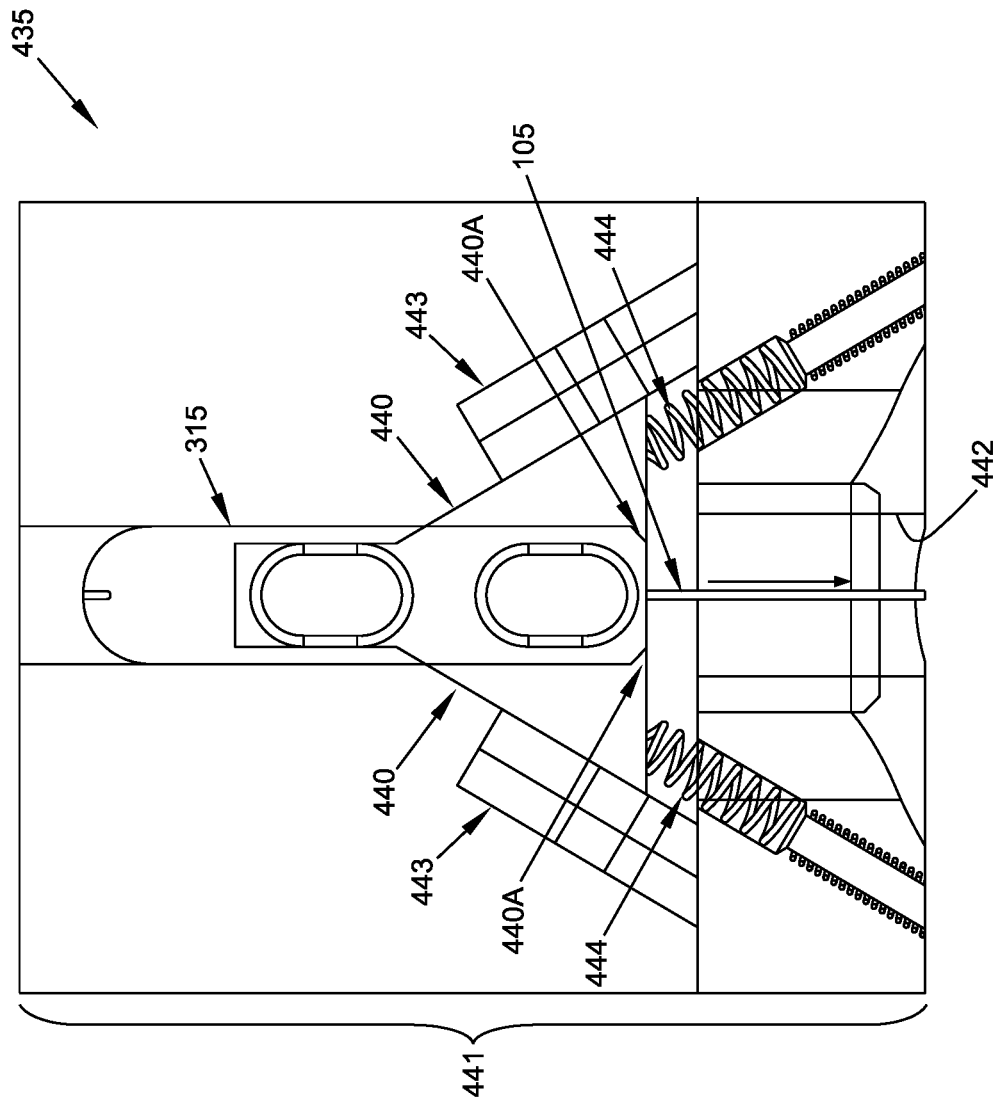
FIGS. 80 and 81 are schematic views showing another form of the present invention, wherein the force delivery mechanism comprises a double wedge force delivery mechanism (note that in FIGS. 80 and 81, only one suture strand is shown for clarity of illustration)
Figure 81:
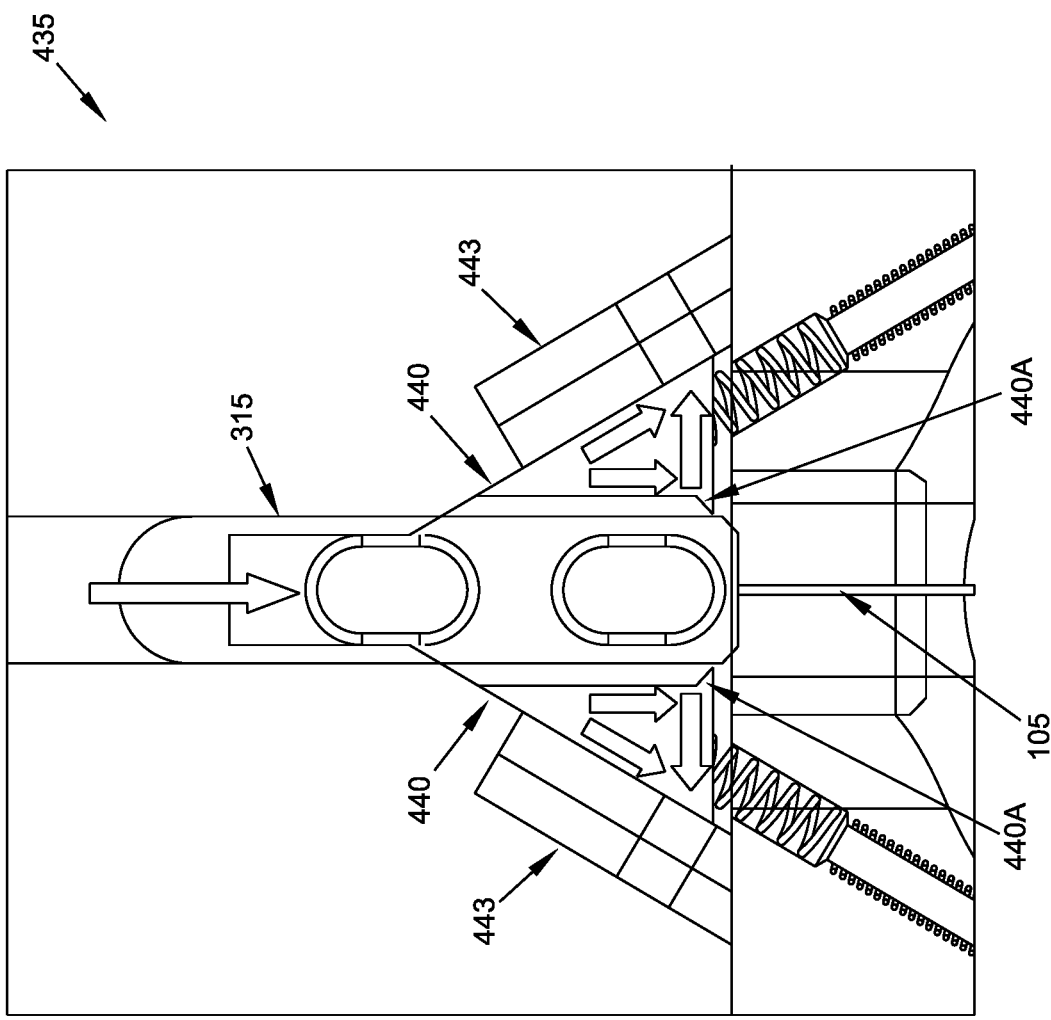

In another form of the invention, the force-limiting (force-controlling) mechanism may comprise the double wedge mechanism 435 shown in FIGS. 80 and 81. This double wedge mechanism uses two spring-loaded wedges 440 to hold cleat 315 to finger pull 325 as force is applied to finger pull 325, whereby to apply force to the thicker proximal suture 105 secured to cleat 315. At the pre-determined maximum level of force, the force applied to spring-loaded wedges 440 by cleat 315 causes the spring-loaded wedges to slide distally and sideways, away from cleat 315, thereby freeing cleat 315 from finger pull 325, and allowing cleat 315 to remain stationary as finger pull 325 moves proximally, whereby to terminate the application of force to thicker proximal suture 105.

More particularly, and looking now at FIGS. 80 and 81, finger pull 325 comprises a plate 441 having an opening 442 extending therethrough, and a pair of opposing inclined guides 443 mounted thereon. Wedges 440 ride along guides 443 so that, as wedges 440 move proximally, the wedges move closer together, and so that, as wedges 440 move distally, the wedges move further part. Springs 444 bias wedges 440 proximally, and hence bias wedges 440 together. Wedges 440 include projections 440A which clamp cleat 315 between the wedges 440 when the wedges are close together (e.g., in the position shown in FIG. 80) but which fail to clamp cleat 315 between the wedges 440 when the wedges are spaced apart (e.g., in the position shown in FIG. 81).

In use, double wedge mechanism 435 starts in the position shown in FIG. 80. Proximal force is applied to finger pull 325, which causes proximal force to be applied to plate 441. As plate 441 begins to move proximally, thicker proximal suture 105 initially stretches, allowing springs 444 to keep wedges 440 proximal and together, but as the finger pull 325 and plate 441 move further proximally, the tension in thicker proximal suture 105 grows. At the pre-determined maximum level of force (e.g., 10±2 lbf), the power of springs 444 is overcome, so that wedges 440 are free to move distally and laterally (FIG. 81), whereby to release cleat 315 from projections 440A, and hence from plate 441 and finger pull 325, and whereby to release the tension on thicker proximal suture 105. Thus it will be seen that with double wedge mechanism 435, force applied to finger pull 325 will be transferred to thicker proximal suture 105 via double wedge mechanism 435 until the level of that force reaches a certain pre-determined level, whereupon the force delivery mechanism is disabled and the application of force to thicker proximal suture 105 is completely terminated.

Suture Cutting Mechanism

Figure 82:
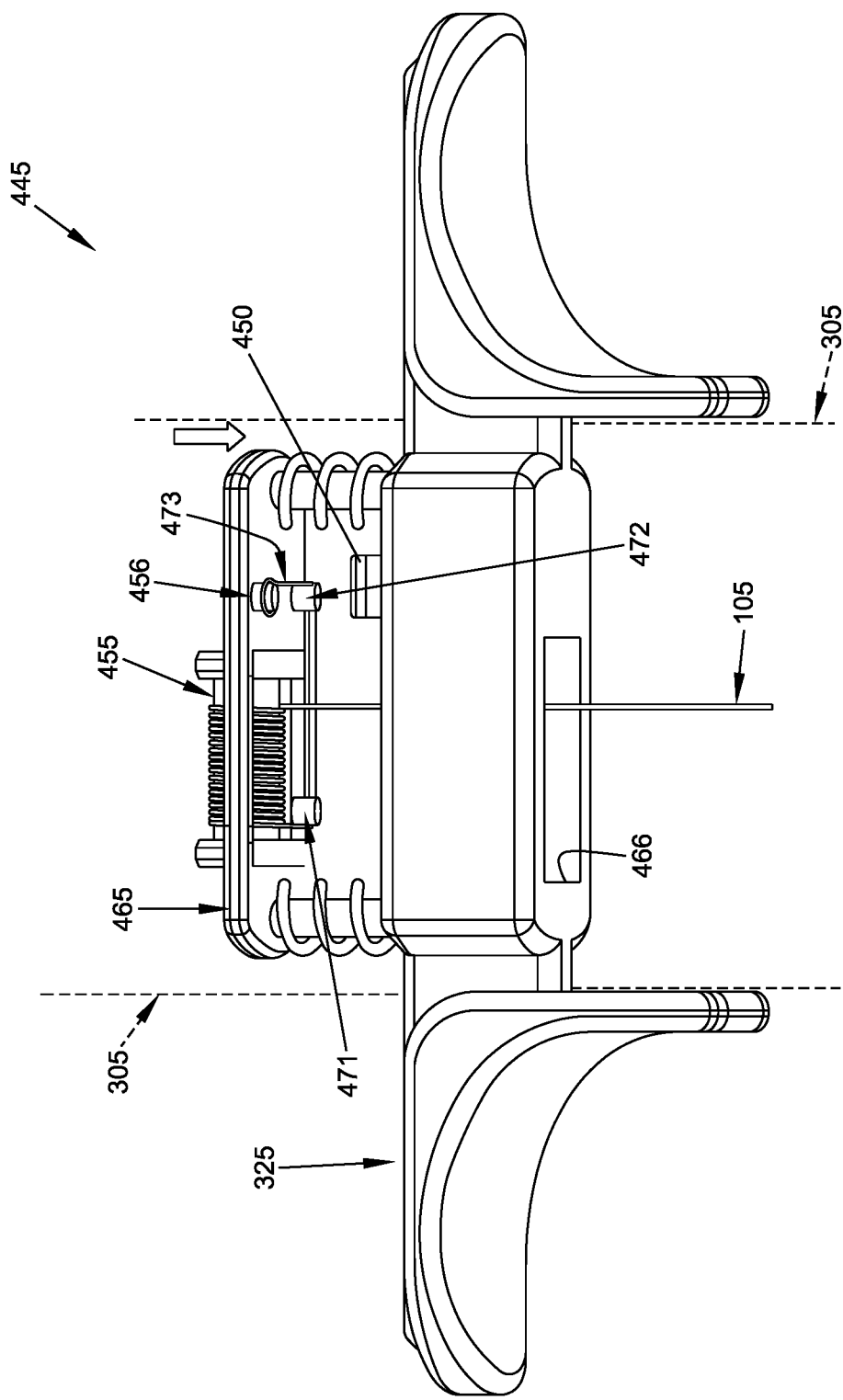
FIGS. 82 and 83 are schematic views showing another form of the present invention, wherein the force delivery mechanism comprises a suture cutting force delivery mechanism (note that in FIGS. 82 and 83, only one suture strand is shown for clarity of illustration)
Figure 83:
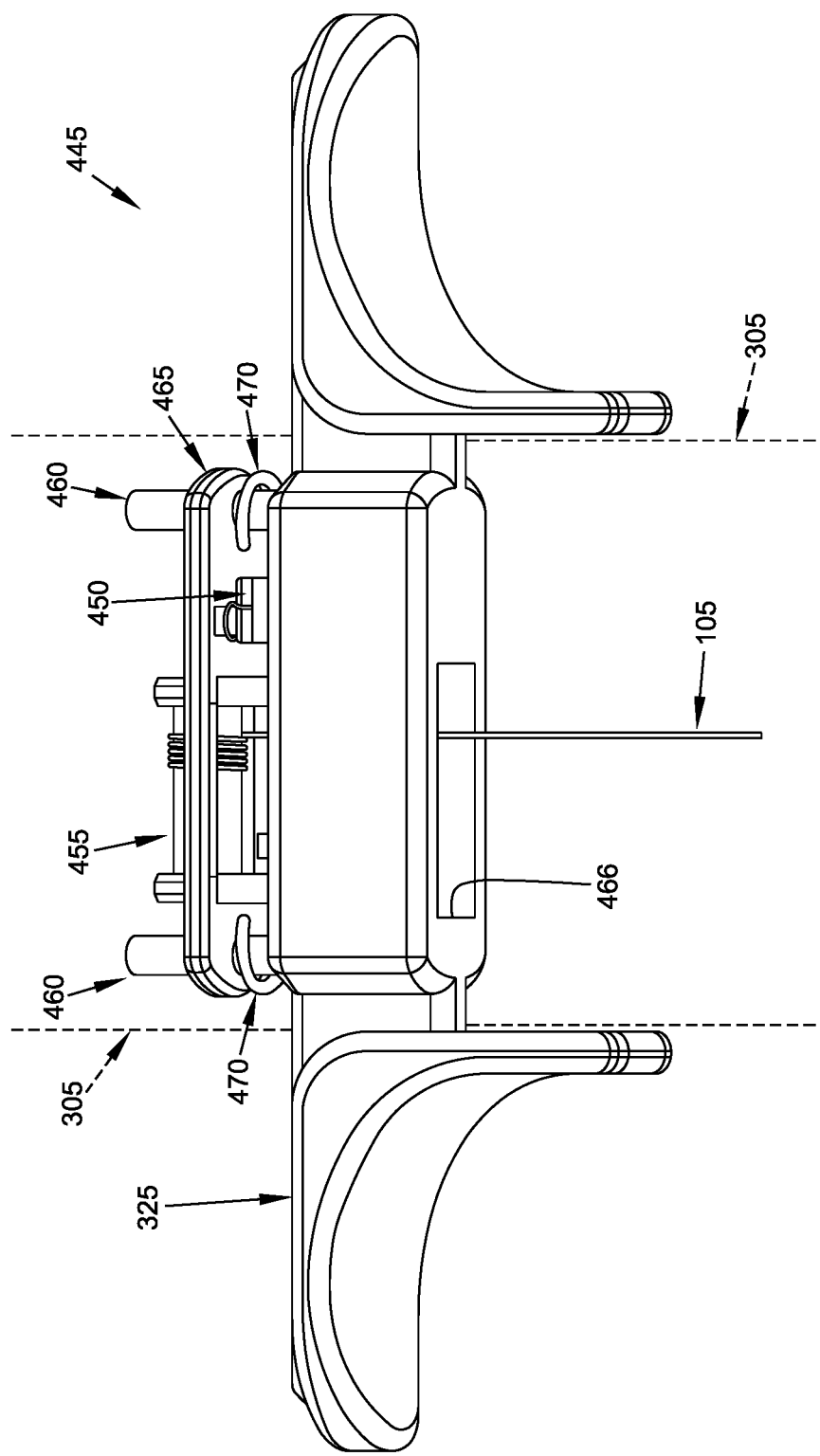

In another form of the invention, the force-limiting mechanism may comprise the suture cutting mechanism 445 shown in FIGS. 82 and 83. This suture cutting mechanism 445 allows the user to apply a force to the thicker proximal suture 105 and then, when the pre-determined maximum level of force is reached, the proximal end of the suture is cut by a blade 450 that is positioned on finger pull 325. Cutting of the thicker proximal suture 105 disables the force delivery mechanism and terminates tension on the suture.

In essence, with suture cutting mechanism 445, the suture extends up hollow push tube 110 of inserter 20, through handle 305 and is attached to finger pull 325 by wrapping the thicker proximal suture 105 around a freely rotating shaft 455 mounted to finger pull 325 and then securing the end of the suture to a mount 456 on finger pull 325. As a result, as long as thicker proximal suture 105 is intact, a proximal force applied to finger pull 325 applies tension to the suture. When a pre-determined maximum level of force is reached, blade 450 cuts the proximal end of thicker proximal suture 105. Once the proximal end of suture 105 has been cut, the tension on the suture 105 is released, since it has been wrapped around the freely rotating shaft 455 mounted to finger pull 325 and is no longer secured to mount 456 on finger pull 325. With the tension on the suture 105 released, the suture 105 is free to unwind off rotating shaft 455 as the user removes the device from the patient. Thus, cutting thicker proximal suture 105 disengages the force delivery mechanism and terminates tension on the suture.

More particularly, in the preferred form of the invention, finger pull 325 comprises a pair of axial rods 460 upon which is movably mounted a platform 465. Blade 450 is fixedly mounted to finger pull 325 so as to face the underside of platform 465, and finger pull 325 comprises an opening 466 for passing thicker proximal suture 105 therethrough. A pair of springs 470 bias platform 465 away from finger pull 325. Platform 465 carries a freely rotating shaft 455 around which is coiled the thicker proximal suture 105. The proximal end of suture 105 comes off freely rotating shaft 455, passes around a post 471 and another post 472, and then terminates at mount 456. Thus, a suture segment 473 extends between post 472 and mount 456. As a result of this construction, a proximal force applied to finger pull 325 causes tension to be applied to thicker proximal suture 105, since the end of thicker proximal suture 105 is secured to mount 456.

When the pulling force applied to finger pull 325 is below the aforementioned pre-determined maximum level of force, springs 470 keep platform 465 biased proximally, away from finger pull 325, and so as to keep suture segment 473 spaced from cutter blade 450. However, when the pulling force applied to finger pull 325 exceeds the aforementioned pre-determined level of force, the power of springs 470 is overcome and the gap between finger pull 325 and platform 465 closes so that cutter blade 450 engages the suture segment 473, whereby to sever the thicker proximal suture 105. As a result, the thicker proximal suture 105 is no longer fixed to mount 456, so that freely rotating shaft 455 can spin, allowing thicker proximal suture 105 to unwind from freely rotating shaft 455 whereby to release the tension on thicker proximal suture 105.

In an alternative embodiment, suture 105 mounts directly to platform 465 (i.e., there is no freely rotating shaft 455). When the pulling force applied to finger pull 325 exceeds the aforementioned pre-determined level of force, the power of springs 470 is overcome and the gap between finger pull 325 and platform 465 closes so that cutter blade 450 engages the suture segment 473, whereby to sever the thicker proximal suture 105. As a result, the thicker proximal suture 105 is no longer fixed to mount 456, allowing thicker proximal suture 105 to be disconnected from platform 465, whereby to release the tension on thicker proximal suture 105.

Alternative Suture Cutting Mechanism

Figure 84:
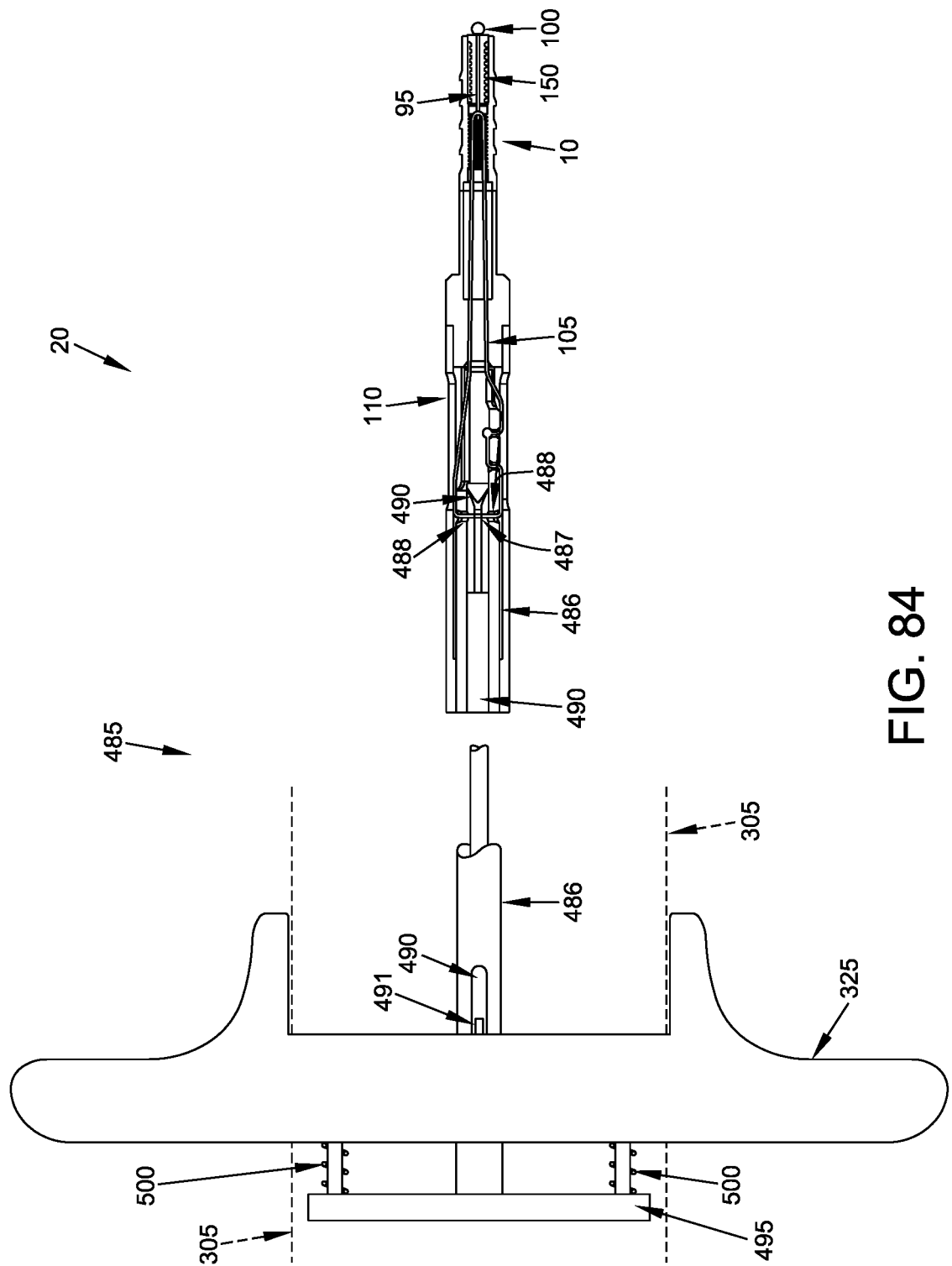
FIGS. 84 and 85 are schematic views showing another form of the present invention, wherein the force delivery mechanism comprises an alternative form of suture cutting force delivery mechanism.
Figure 85:
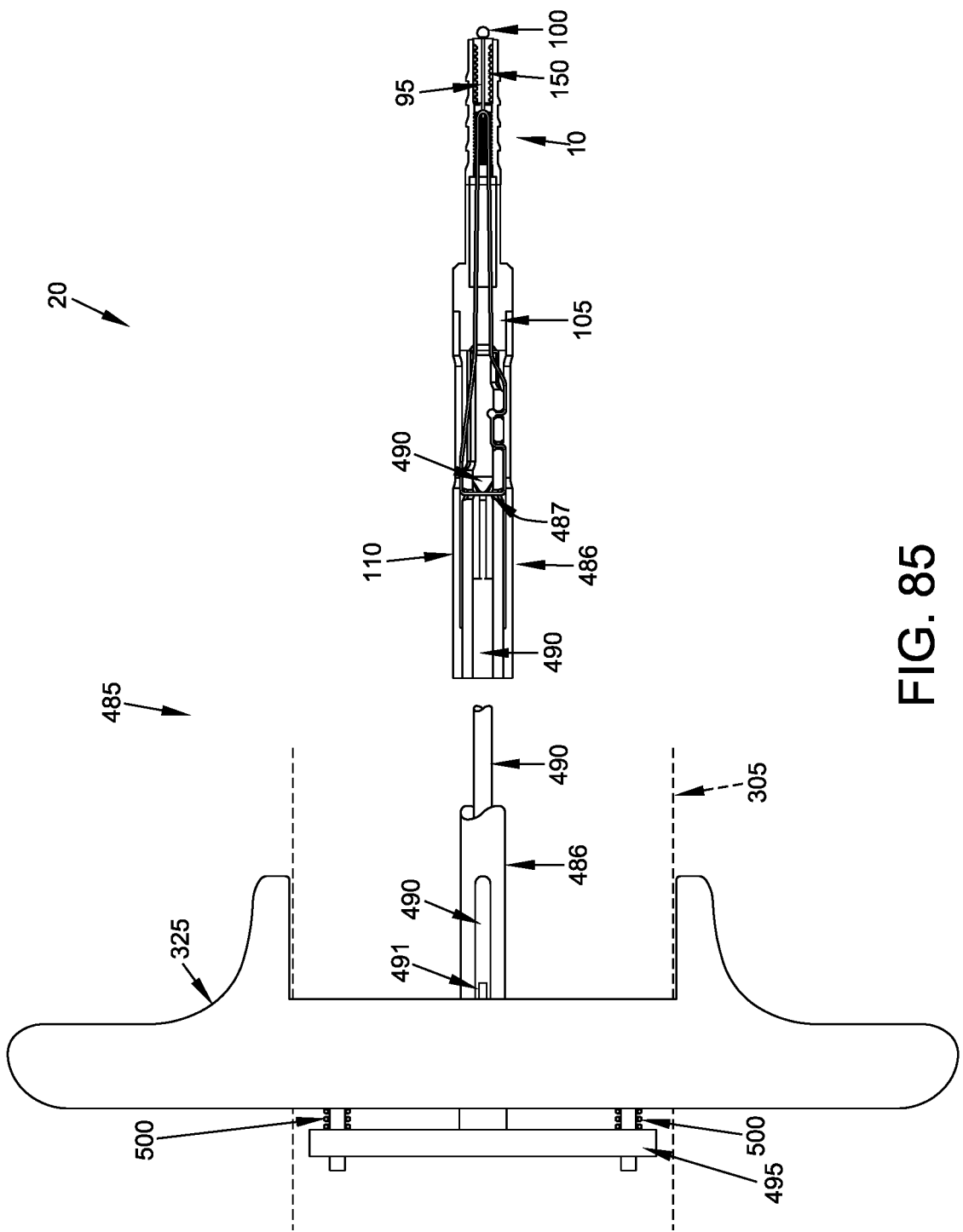

In another form of the invention, the force-limiting mechanism may comprise the alternative suture cutting mechanism 485 shown in FIGS. 84 and 85. In this form of the invention, where anchor 10 comprises the deployment cylinder 150 which is moved by a thinner distal suture 95 having an enlargement 100 at its distal end, and where thinner distal suture 95 is itself moved by a thicker proximal suture 105 extending up into hollow push tube 110 of inserter 20, the thicker proximal suture 105 is coupled to a movable shaft 486 disposed within hollow push tube 110 of inserter 20 (in this embodiment, suture 105 may not serve to secure tissue to bone, rather, another suture, not shown, may be secured to the body of the anchor and used to secure tissue to bone). Thicker proximal suture 105 may comprise a loop having a segment 487 extending through diametrically opposed openings 488 formed in movable shaft 486, with segment 487 extending across the central lumen of the movable shaft 486. The inserter 20 may have a blade 490 which is disposed in the central lumen of the movable shaft 486. In this form of the invention, the blade 490 is secured to the finger pull 325 (e.g., via a connector 491), and the movable shaft 486 is secured to a body 495 which is spring biased away from finger pull 325 by virtue of springs 500. In this form of the invention, as long as the level of force applied to the finger pull 325 is below the aforementioned pre-determined maximum level of force, springs 500 will keep body 495 biased away from finger pull 325, and hence keep blade 490 away from the suture segment 487 formed by thicker proximal suture 105, so that proximal movement of finger pull 325 will apply a proximal force to thicker proximal suture 105, whereby to actuate the anchor. However, as soon as the level of force applied to finger pull 325 reaches the aforementioned pre-determined maximum level of force (e.g., 10±2 lbf), the power of springs 500 will be overcome and finger pull 325 will approach body 495, whereby to bring the cutter blade 490 into engagement with the suture segment 487 formed by thicker proximal suture 105, and whereby to sever thicker proximal suture 105 and terminate the application of an actuation force to the anchor.

In other words, in this form of the invention, as long as the level of force applied to finger pull 325 is below the aforementioned maximum level of force, the force applied to finger pull 325 is transmitted to body 495, and hence to movable shaft 486, and hence to thicker proximal suture 105, whereby to actuate the anchor, with springs 500 keeping body 495 sufficiently separated from finger pull 325 to keep blade 490 separated from segment 487 of thicker proximal suture 105, whereby to maintain the integrity of thicker proximal suture 105. However, as soon as the level of force applied to finger pull 325 reaches the aforementioned maximum level of force, the power of springs 500 is overcome, so that the gap between body 495 and finger pull 325 decreases, whereby to cause blade 490 to engage segment 487 of thicker proximal suture 105 and sever the suture. This disengages the force delivery mechanism and terminates the tension on the suture 105.

Dogbone Mechanism

Figure 86:
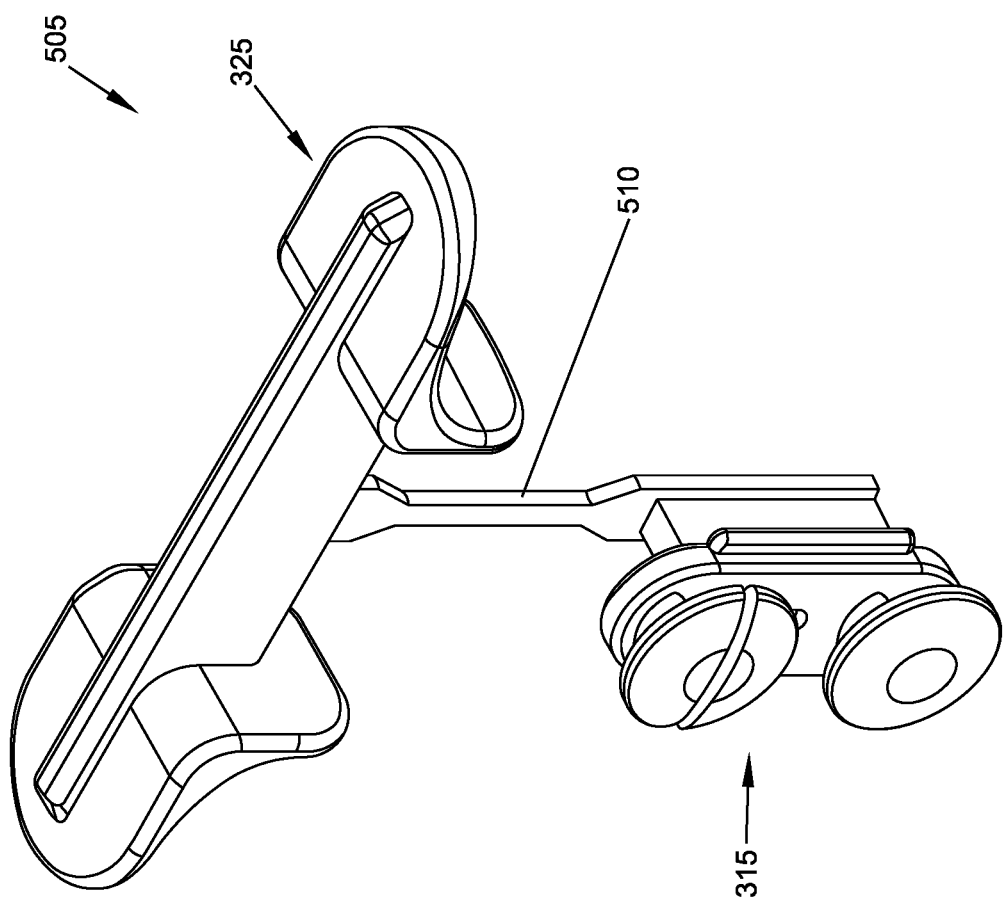
FIG. 86 is a schematic view showing another form of the present invention, wherein the force delivery mechanism comprises a dogbone force delivery mechanism.

In another form of the present invention, the force-limiting mechanism may comprise the dogbone mechanism 505 shown in FIG. 86. Dogbone mechanism 505 allows the user to apply force to the thicker proximal suture 105 which is secured to cleat 315 by pulling proximally on finger pull 325, with dogbone 510 transmitting force between the two parts (i.e., between finger pull 325 and cleat 315). Dogbone 510 is constructed so that at force levels below the aforementioned pre-determined maximum level of force, dogbone 510 will remain intact and will transmit force between finger pull 325 and cleat 315.

However, dogbone 510 is also constructed so that at force levels above the aforementioned pre-determined maximum level of force, dogbone 510 will break and no longer transmit force between finger pull 325 and cleat 315. Thus, in this form of the invention, dogbone 510 effectively acts as a mechanical fuse, in the sense that it terminates force transmission as soon as the force applied to finger pull 325 reaches the aforementioned pre-determined maximum level of force. It will be appreciated that the breaking force of dogbone 510 is dictated by material selection and dogbone geometry.

Additional "Controlled Component Failure" Designs

It will be appreciated that in the dogbone mechanism 505 discussed above, the force-limiting feature of the force delivery mechanism is provided by the "controlled component failure" of the dogbone. In essence, with this design, a component is designed to act as a "mechanical fuse", whereby it will intentionally fail when the applied force exceeds the aforementioned pre-determined maximum level of force, whereby to terminate the application of an actuation force to the anchor assembly. The component which acts as the "mechanical fuse" is selected so that the component failure will not undermine the integrity of the anchor fixation in the bone.

It will be appreciated that numerous other designs can be provided which use the "controlled component failure" scheme of the dogbone mechanism.

Thus, for example, and looking now at FIGS. 87 and 88, in one form of the invention, thicker proximal suture 105 can be engineered to break when the applied force exceeds the aforementioned pre-determined maximum level of force (it should be appreciated that in these figures, and the figures which follow, the inserter is omitted from the drawing in order to improve clarity of understanding). Of course, in this form of the invention, inasmuch as thicker proximal suture 105 is designed to break when the applied force exceeds the aforementioned pre-determined maximum level of force, an additional suture S is provided for securing tissue to bone. In an alternative form of the invention (not shown), the thinner distal suture 95 can be engineered to break when the applied force exceeds the aforementioned pre-determined maximum level of force.

Or, as shown in FIGS. 89 and 90, where a mechanical hook 515 is used in place of thicker proximal suture 105 to apply a proximal force to thinner distal suture 95, mechanical hook 515 can be engineered to fail (e.g., yielding by bending) when the applied force exceeds the aforementioned pre-determined maximum level of force. Of course, in this form of the invention, inasmuch as mechanical hook 515 is designed to fail when the applied force exceeds the aforementioned pre-determined maximum level of force, an additional suture S is provided for securing tissue to bone.

Figure 91:
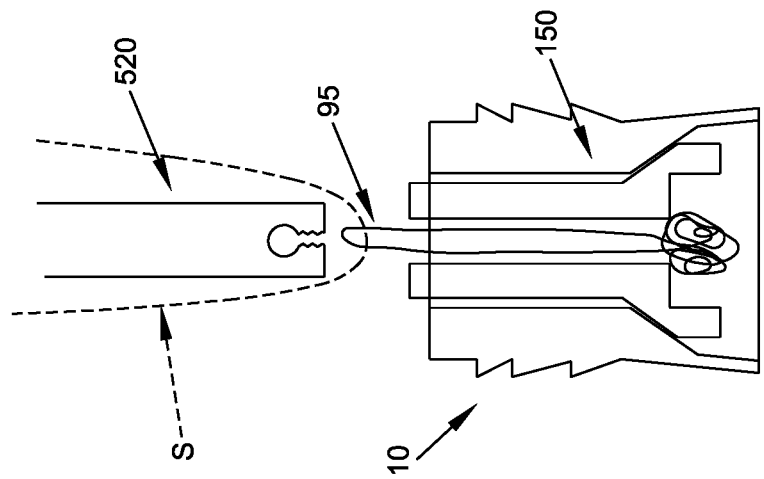
Figure 92:
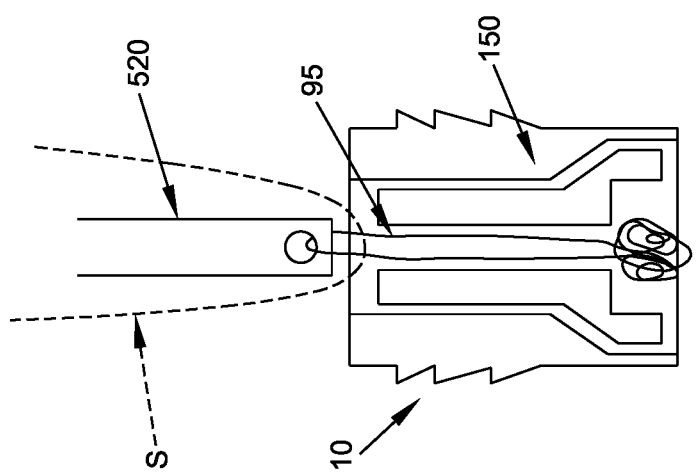

Or, as shown in FIGS. 91 and 92, where a rod 520 is used in place of thicker proximal suture 105 to apply a proximal force to thinner distal suture 95, rod 520 can be engineered to fail (e.g., by the thinner distal suture 95 tearing through a segment 521 of rod 520) when the applied force exceeds the aforementioned pre-determined maximum level of force. It will be appreciated that the force at which thinner distal suture 95 tears through segment 521 of rod 520 is dictated by material selection and geometry of rod 520 and thinner distal suture 95. Of course, in this form of the invention, inasmuch as rod 520 is designed to fail when the applied force exceeds the aforementioned pre-determined maximum level of force, an additional suture S is provided for securing tissue to bone.

Figure 93:
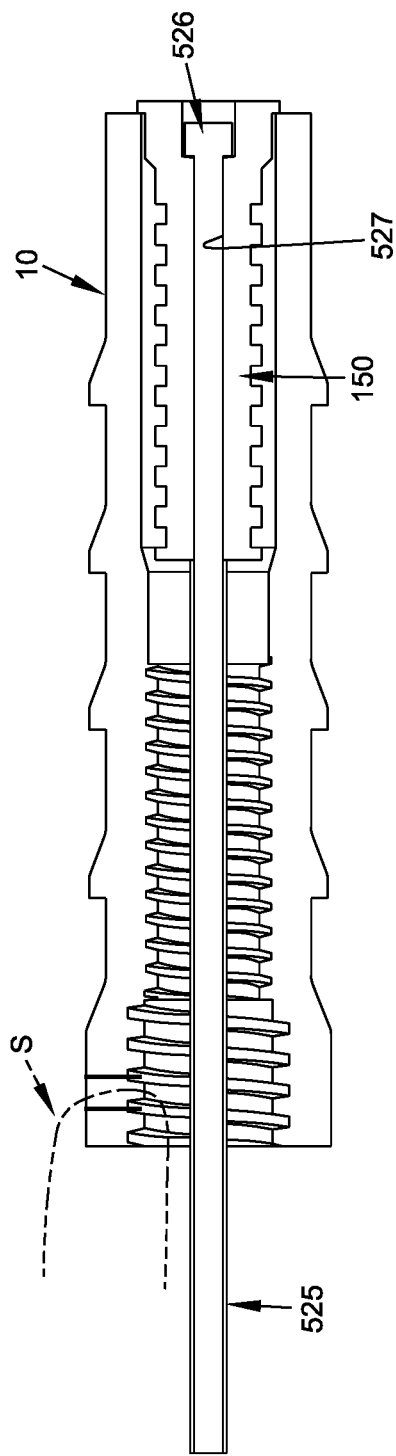
Figure 94:
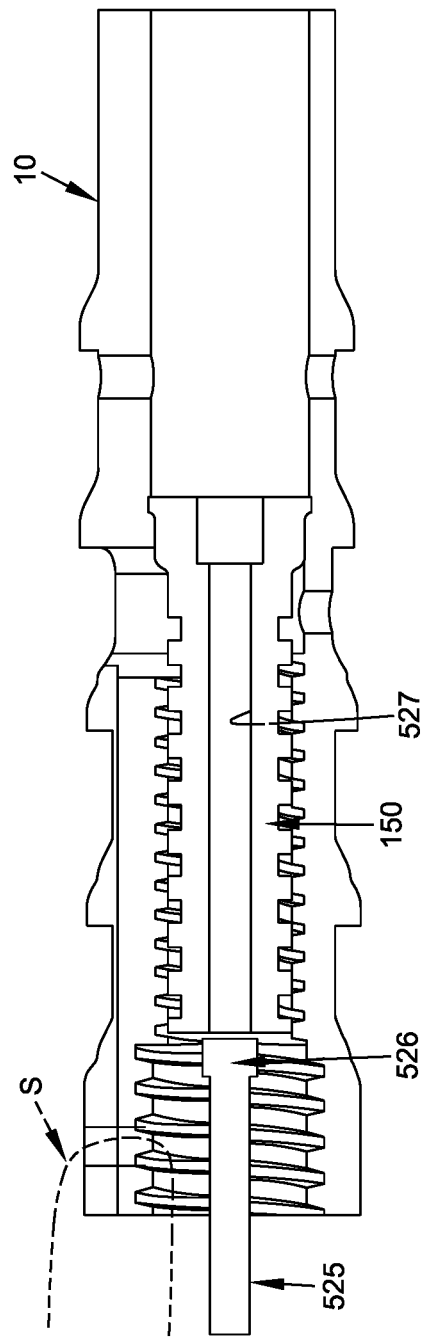

Or, as shown in FIGS. 93 and 94, where a rod 525 is used in place of both thinner distal suture 95 and thicker proximal suture 105 to apply a proximal force to deployment cylinder 150, deployment cylinder 150 can be engineered to fail when the applied force exceeds the aforementioned pre-determined maximum level of force. Specifically, in one form of the invention, rod 525 comprises an enlargement 526 which is positioned distal to a narrowed section 527 of deployment cylinder 150. Enlargement 526 has a profile in at least one dimension which is larger than at least one dimension of narrowed section 527. Enlargement 526 and narrowed section 527 are constructed so that at force levels below the aforementioned pre-determined maximum level of force, enlargement 526 and narrowed section 527 will both remain intact and will transmit force from rod 525 to deployment cylinder 150. However, at force levels above the aforementioned pre-determined maximum level of force, one or the other, or both, of enlargement 526 and narrowed section 527 will deform, so that rod 525 can move proximally relative to deployment cylinder 150, and—once free of narrowed section 527—will no longer transmit force between rod 525 and deployment cylinder 150. It will be appreciated that the breaking force of enlargement 526, narrowed section 527, or both, is dictated by material selection and geometry of both rod 525 and deployment cylinder 150. Of course, in this form of the invention, inasmuch as enlargement 526, narrowed section 527, or both, are designed to fail when the applied force exceeds the aforementioned pre-determined maximum level of force, an additional suture S (threaded through an opening in the anchor) is provided for securing tissue to bone.

Figure 95:
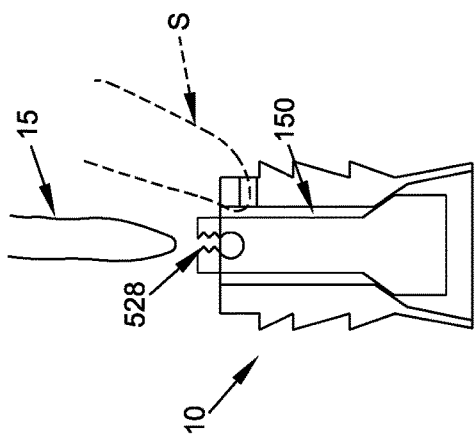
Figure 96:
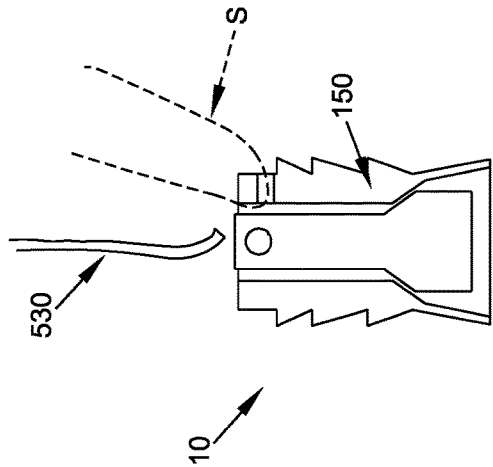

Or, as shown in FIGS. 95 and 96, where a suture 15 (e.g., a thinner distal suture 95 or a thicker proximal suture 105) is used to apply a proximal force to deployment cylinder 150, deployment cylinder 150 can be engineered to fail (e.g., by the suture 15 tearing through a segment 528 of deployment cylinder 150) when the applied force exceeds the aforementioned pre-determined maximum level of force. It will be appreciated that the force at which suture 15 tears through segment 528 of deployment cylinder 150 is dictated by material selection and geometry of deployment cylinder 150 and suture 15. Of course, in this form of the invention, inasmuch as deployment cylinder 150 is designed to fail when the applied force exceeds the aforementioned pre-determined maximum level of force, an additional suture S (threaded through an opening in the anchor) is provided for securing tissue to bone.

Figure 97:
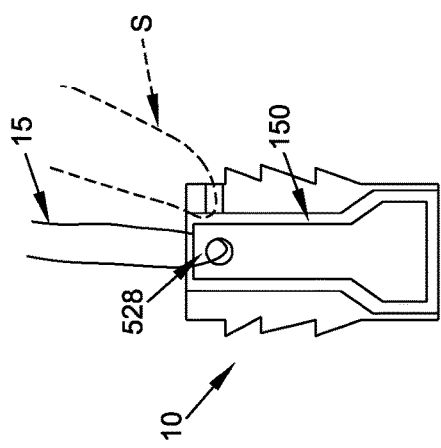
Figure 98:
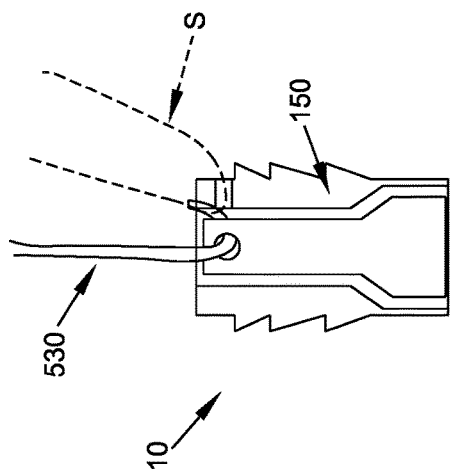

Or, as shown in FIGS. 97 and 98, where a hook 530 is used to apply a proximal force to deployment cylinder 150, hook 530 can be engineered to fail when the applied force exceeds the aforementioned pre-determined maximum level of force. Again, it will be appreciated that the force at which hook 530 fails is dictated by the material selection and geometry of hook 530. Of course, in this form of the invention, inasmuch as hook 530 is designed to fail when the applied force exceeds the aforementioned pre-determined maximum level of force, an additional suture S (threaded through an opening in the anchor) is provided for securing tissue to bone.

Figure 100:
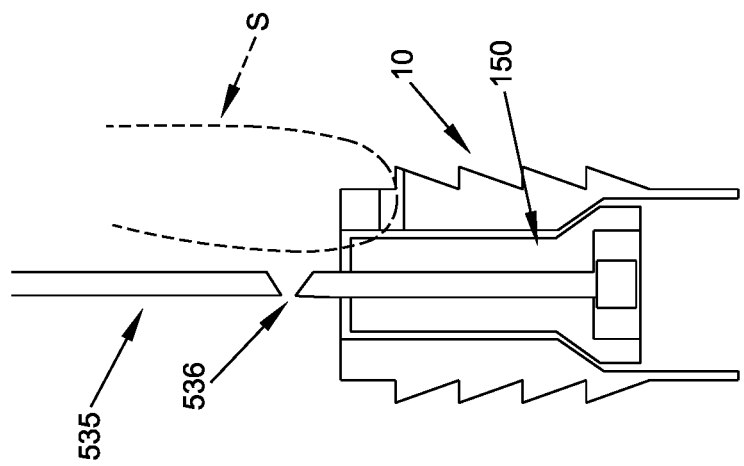
Figure 99:
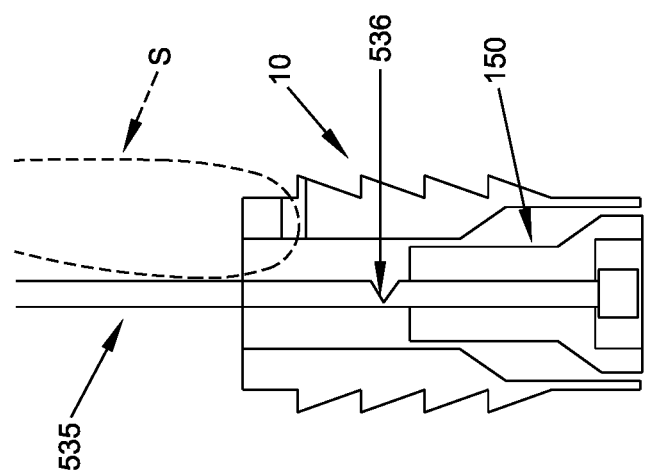

Or, as shown in FIGS. 99 and 100, where a pull rod 535 is used to apply a proximal force to deployment cylinder 150, pull rod 535 can be engineered to fail when the applied force exceeds the aforementioned pre-determined maximum level of force. For example, pull rod 535 can comprise a break section 536. Break section 536 may be a narrowing in the pull rod 535 (i.e. creating a weak point in the pull rod 535) or other feature or geometry which forces the pull rod 535 to break at that location when the level of force applied to pull rod 535 exceeds the aforementioned pre-determined maximum level of force. Of course, in this form of the invention, inasmuch as pull rod 535 is designed to fail when the applied force exceeds the aforementioned pre-determined maximum level of force, an additional suture S (threaded through an opening in the anchor) is provided for securing tissue to bone.

Alternative Construction and Method of Use

In one form of the present invention, anchor 10 of suture anchor system 5 may be delivered trans-labrally, i.e., through the labrum and into the acetabular bone, e.g., such as was described above.

In an alternative embodiment of the present invention, anchor 10 may be placed directly into the acetabular bone, without passing through the labrum first, and then suture 15 may be passed through the labrum. In this form of the invention, the components of suture anchor system 5 may remain the same. Alternatively, in this form of the invention, the distal end of hollow guide 25 need not have a sharp tip/edge 136 for penetrating the labrum as described above, and may instead have engagement features for engaging the acetabular bone. One such feature may be a tooth or a plurality of teeth. In this form of the invention, the distal end of the hollow guide may also include a window for confirming that the anchor is properly placed into the bone.

Curved or Angled Configuration and Method of Use

Suture anchor system 5 may also comprise a curved or angled configuration. More particularly, hollow guide 25 may comprise a curve or angle at its distal end. In this form of the invention, the punch (or drill) 30, inserter 20 and anchor 10 are adapted to pass through the curved or angled hollow guide 25 so as to permit a curved or angled delivery of anchor 10.

Use of the Novel Suture Anchor System for Other Tissue Re-attachment

It should be appreciated that suture anchor system 5 may also be used for re-attaching other soft tissue of the hip joint, or for re-attaching tissue of other joints, or for re-attaching tissue elsewhere in the body. In this respect it should be appreciated that suture anchor system 5 may be used to attach soft tissue to bone or soft tissue to other soft tissue, or for attaching objects (e.g., prostheses) to bone other tissue.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for securing an object to bone, the apparatus comprising:
an anchor comprising a body and a movable element; and
an actuation element extending from the movable element for moving the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to apply a magnitude of tension to the actuation element, whereby to move the movable element proximally within the body of the anchor, wherein when the magnitude of tension applied to the actuation element exceeds a pre-determined limit, no further tension is applied to the movable element;

wherein the force delivery mechanism is spring-biased.

2. Apparatus according to claim 1 wherein moving the movable element proximally causes the movable element to bind a suture to the anchor.

3. Apparatus according to claim 2 wherein moving the movable element proximally causes the movable element to compress the suture, whereby to bind the suture to the anchor.

4. Apparatus according to claim 1 wherein moving the movable element proximally causes the movable element to bind the anchor to the bone.

5. Apparatus according to claim 4 wherein the body of the anchor is expandable, wherein moving the movable element proximally causes the movable element to expand the body of the anchor, whereby to bind the anchor to the bone.

6. Apparatus according to claim 1 wherein the force delivery mechanism disengages from the actuation element when the magnitude of tension applied to the actuation element exceeds the pre-determined limit so that no further tension is applied to the movable element.

7. Apparatus according to claim 1 wherein the actuation element comprises at least one of a suture and a rod.

8. Apparatus according to claim 1 wherein the force delivery mechanism comprises a first portion and a second portion, wherein the first portion is designed to separate from the second portion when the magnitude of tension applied to the actuation element exceeds the pre-determined limit, whereby separation of the first portion from the second portion ceases delivery of tension to the movable element.

9. Apparatus for securing an object to bone, the apparatus comprising:
an anchor comprising a body and a movable element; and
an actuation element extending from the movable element for moving the movable element within the body of the anchor, and further wherein the actuation element comprises a suture; and
an inserter for deploying the anchor in a hole formed in a bone, the inserter comprising:
a shaft for releasably engaging the anchor; and
a force delivery mechanism connected to the shaft and connected to the suture, the force delivery mechanism being configured to apply a magnitude of tension to move the suture proximally, whereby to move the movable element proximally within the body of the anchor, wherein when the magnitude of tension applied to the suture exceeds a pre-determined limit, no further tension is applied to the movable element.

10. Apparatus according to claim 9 wherein moving the movable element proximally causes the movable element to bind a second suture to the anchor.

11. Apparatus according to claim 10 wherein moving the movable element proximally causes the movable element to compress the second suture, whereby to bind the second suture to the anchor.

12. Apparatus according to claim 9 wherein moving the movable element proximally causes the movable element to bind the anchor to the bone.

13. Apparatus according to claim 12 wherein the body of the anchor is expandable, wherein moving the movable element proximally causes the movable element to expand the body of the anchor, whereby to bind the anchor to the bone.

14. Apparatus according to claim 9 wherein the force delivery mechanism is spring-biased.

15. Apparatus according to claim 9 wherein the force delivery mechanism disengages from the suture when the magnitude of tension applied to the suture exceeds the pre-determined limit so that no further tension is applied to the movable element.

16. Apparatus according to claim 9 wherein the force delivery mechanism comprises a first portion and a second portion, wherein the first portion is designed to separate from the second portion when the magnitude of tension applied to the suture exceeds the pre-determined limit, whereby separation of the first portion from the second portion ceases delivery of tension to the movable element.

17. Apparatus for securing an object to bone, the apparatus comprising:
an anchor comprising a body and a movable element; and
an actuation element extending from the movable element, wherein applying a force to the actuation element moves the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to deliver a force to the actuation element to move the movable element within the anchor, wherein the force delivery mechanism is configured to limit the maximum force applied to the actuation element, wherein the force delivered to the actuation element moves the actuation element proximally, and further wherein the distance that the movable element moves within the anchor is determined by the force applied to the actuation element and not by the distance that the force delivery mechanism moves;

wherein the force delivery mechanism is spring-biased.

18. Apparatus according to claim 17 wherein moving the actuation element proximally causes the movable element to bind a suture to the anchor.

19. Apparatus according to claim 17 wherein moving the actuation element proximally causes the movable element to bind the anchor to the bone.

20. Apparatus according to claim 17 wherein the force delivery mechanism disengages from the actuation element when the magnitude of force applied to the actuation element exceeds a pre-determined limit so that no further force is applied to the movable element.

21. Apparatus according to claim 17 wherein the actuation element comprises at least one of a suture and a rod.

22. Apparatus according to claim 17 wherein the force delivery mechanism comprises a first portion and a second portion, wherein the first portion is designed to separate from the second portion when the magnitude of force applied to the actuation element exceeds a pre-determined limit, whereby separation of the first portion from the second portion ceases delivery of force to the movable element.

23. Apparatus for securing an object to bone, the apparatus comprising:
an anchor comprising a body and a movable element; and
an actuation element extending from the movable element, wherein applying a force to the actuation element moves the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to deliver a force to the actuation element to move the movable element within the anchor, wherein the force delivered to the actuation element is terminated if the force delivered to the actuation element reaches a pre-selected force regardless of the distance moved by the movable element;
wherein moving the actuation element causes the movable element to bind the anchor to the bone;
wherein the actuation element is moved distally to bind the anchor to the bone.

24. Apparatus for securing an object to bone, the apparatus comprising:
an anchor comprising a body and a movable element; and
an actuation element extending from the movable element, wherein applying a force to the actuation element moves the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to deliver a force to the actuation element to move the movable element within the anchor, wherein the force delivered to the actuation element is terminated if the force delivered to the actuation element reaches a pre-selected force regardless of the distance moved by the movable element;
wherein moving the actuation element causes the movable element to bind the anchor to the bone;
wherein the actuation element is rotated to bind the anchor to the bone.

25. Apparatus according to claim 24 wherein moving the movable element proximally causes the movable element to bind a suture to the anchor.

26. Apparatus according to claim 24 wherein moving the movable element proximally causes the movable element to bind the anchor to the bone.

27. Apparatus according to claim 24 wherein the force delivery mechanism is spring-biased.

28. Apparatus according to claim 24 wherein the force delivery mechanism disengages from the actuation element when the magnitude of force applied to the actuation element exceeds the pre-selected force so that no further force is applied to the movable element.

29. Apparatus according to claim 24 wherein the actuation element comprises at least one of a suture and a rod.

30. Apparatus according to claim 24 wherein the force delivery mechanism comprises a first portion and a second portion, wherein the first portion is designed to separate from the second portion when the magnitude of force applied to the actuation element exceeds the pre-selected force, whereby separation of the first portion from the second portion ceases delivery of force to the movable element.

31. Apparatus for securing an object to bone, the apparatus comprising:
an anchor comprising a body and a movable element; and
an actuation element extending from the movable element, wherein applying a force to the actuation element moves the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to deliver a force to the actuation element to move the movable element within the anchor, wherein the force delivered to the actuation element is terminated if the force delivered to the actuation element reaches a pre-selected force regardless of the distance moved by the movable element;
wherein the force delivery mechanism is spring-biased.

32. Apparatus according to claim 31 wherein moving the movable element proximally causes the movable element to bind a suture to the anchor.

33. Apparatus according to claim 31 wherein moving the movable element proximally causes the movable element to bind the anchor to the bone.

34. Apparatus according to claim 31 wherein the force delivery mechanism disengages from the actuation element when the magnitude of force applied to the actuation element exceeds the pre-selected force so that no further force is applied to the movable element.

35. Apparatus according to claim 31 wherein the actuation element comprises at least one of a suture and a rod.

36. Apparatus according to claim 31 wherein the force delivery mechanism comprises a first portion and a second portion, wherein the first portion is designed to separate from the second portion when the magnitude of force applied to the actuation element exceeds the pre-selected force, whereby separation of the first portion from the second portion ceases delivery of force to the movable element.

37. Apparatus for securing an object to bone, the apparatus comprising:
an anchor comprising a body and a movable element; and
an actuation element extending from the movable element, wherein applying a force to the actuation element moves the movable element within the body of the anchor; and
an inserter for deploying the anchor in a hole formed in a bone, the inserter comprising:
a shaft for releasably engaging the anchor; and
a force delivery mechanism connected to the shaft and connected to the actuation element, the force delivery mechanism being configured to deliver a force to the actuation element to move the movable element within the anchor, wherein the force is delivered to the actuation element by moving the force delivery mechanism, wherein the force delivered to the actuation element is terminated if the force delivered to the actuation element reaches a pre-selected force regardless of the distance moved by the force delivery mechanism;
wherein moving the actuation element causes the movable element to bind the anchor to the bone;

wherein the actuation element is moved distally to bind the anchor to the bone.

38. Apparatus for securing an object to bone, the apparatus comprising:

an anchor comprising a body and a movable element; and an actuation element extending from the movable element, wherein applying a force to the actuation element moves the movable element within the body of the anchor; and an inserter for deploying the anchor in a hole formed in a bone, the inserter comprising:

a shaft for releasably engaging the anchor; and a force delivery mechanism connected to the shaft and connected to the actuation element, the force delivery mechanism being configured to deliver a force to the actuation element to move the movable element within the anchor, wherein the force is delivered to the actuation element by moving the force delivery mechanism, wherein the force delivered to the actuation element is terminated if the force delivered to the actuation element reaches a pre-selected force regardless of the distance moved by the force delivery mechanism;

wherein moving the actuation element causes the movable element to bind the anchor to the bone;

wherein the actuation element is rotated to bind the anchor to the bone.

39. Apparatus according to claim 38 wherein moving the movable element proximally causes the movable element to bind a suture to the anchor.

40. Apparatus according to claim 38 wherein moving the movable element proximally causes the movable element to bind the anchor to the bone.

41. Apparatus according to claim 38 wherein the force delivery mechanism is spring-biased.

42. Apparatus according to claim 38 wherein the force delivery mechanism disengages from the actuation element when the magnitude of force applied to the actuation element exceeds the pre-selected force so that no further force is applied to the movable element.

43. Apparatus according to claim 38 wherein the actuation element comprises at least one of a suture and a rod.

44. Apparatus according to claim 38 wherein the force delivery mechanism comprises a first portion and a second portion, wherein the first portion is designed to separate from the second portion when the magnitude of force applied to the actuation element exceeds the pre-selected force, whereby separation of the first portion from the second portion ceases delivery of force to the movable element.

45. Apparatus for securing an object to bone, the apparatus comprising:

an anchor comprising a body and a movable element; and an actuation element extending from the movable element, wherein applying a force to the actuation element moves the movable element within the body of the anchor; and an inserter for deploying the anchor in a hole formed in a bone, the inserter comprising:

a shaft for releasably engaging the anchor; and a force delivery mechanism connected to the shaft and connected to the actuation element, the force delivery mechanism being configured to deliver a force to the actuation element to move the movable element within the anchor, wherein the force is delivered to the actuation element by moving the force delivery mechanism, wherein the force delivered to the actuation element is terminated if the force delivered to the actuation element reaches a pre-selected force regardless of the distance moved by the force delivery mechanism;

wherein the force delivery mechanism is spring-biased.

46. Apparatus according to claim 45 wherein moving the movable element proximally causes the movable element to bind a suture to the anchor.

47. Apparatus according to claim 45 wherein moving the movable element proximally causes the movable element to bind the anchor to the bone.

48. Apparatus according to claim 45 wherein the force delivery mechanism disengages from the actuation element when the magnitude of force applied to the actuation element exceeds the pre-selected force so that no further force is applied to the movable element.

49. Apparatus according to claim 45 wherein the actuation element comprises at least one of a suture and a rod.

50. Apparatus according to claim 45 wherein the force delivery mechanism comprises a first portion and a second portion, wherein the first portion is designed to separate from the second portion when the magnitude of force applied to the actuation element exceeds the pre-selected force, whereby separation of the first portion from the second portion ceases delivery of force to the movable element.

\* \* \* \* \*